_United States Patent_ [19] [11] Patent Number: 6,159,936

Lehrer et al. [45] Date of Patent: *Dec. 12, 2000

[54] COMPOSITIONS AND METHODS FOR TREATING AND PREVENTING MICROBIAL AND VIRAL INFECTIONS

[75] Inventors: Robert I. Lehrer, Santa Monica; Sylvia S. L. Harwig, Woodland Hills, both of Calif.; Vladimir N. Kokryakov, St. Petersburg, Russian Federation

[73] Assignee: The Regents of the University of California, Oakland, Calif.

[*] Notice: This patent is subject to a terminal disclaimer.

[21] Appl. No.: 09/128,345

[22] Filed: Aug. 3, 1998

Related U.S. Application Data

[62] Continuation of application No. 08/499,523, Jul. 7, 1995, Pat. No. 5,804,558, which is a continuation-in-part of application No. 08/451,832, filed as application No. PCT/US94/08305, Jul. 20, 1994, abandoned, and a continuation-in-part of application No. 08/243,879, May 17, 1994, Pat. No. 5,708,145, and a continuation-in-part of application No. 08/182,483, Jan. 13, 1994, Pat. No. 5,693,486, and a continuation-in-part of application No. 08/095,769, Jul. 26, 1993, Pat. No. 5,464,823, and a continuation-in-part of application No. 08/093,926, Jul. 20, 1993, abandoned.

[51] Int. Cl.[7] ............ A61K 38/04; C07K 7/00; C12N 15/12; C12P 21/02; C12P 21/04

[52] U.S. Cl. ............ 514/13; 514/12; 424/405; 435/69.1; 435/252.3; 435/320.1; 530/236; 536/23.5

[58] Field of Search ............ 514/12, 13; 424/405; 530/326; 435/69.1, 252.3, 320.1; 536/23.5

[56] References Cited

U.S. PATENT DOCUMENTS

| | | | |
|---|---|---|---|
| 4,543,252 | 9/1985 | Lehrer et al. | 514/12 |
| 4,652,639 | 3/1987 | Stabinsky | 435/91.52 |
| 4,659,692 | 4/1987 | Lehrer et al. | 514/12 |
| 4,705,777 | 11/1987 | Lehrer et al. | 514/12 |
| 5,087,569 | 2/1992 | Gabay et al. | 435/212 |
| 5,126,257 | 6/1992 | Gabay et al. | 435/212 |
| 5,171,739 | 12/1992 | Scott et al. | 514/12 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,338,724 | 8/1994 | Gabay et al. | 514/12 |
| 5,422,424 | 6/1995 | Selsted et al. | 530/324 |
| 5,432,270 | 7/1995 | Zasloff et al. | 536/23.5 |
| 5,447,914 | 9/1995 | Travis et al. | 514/16 |
| 5,458,874 | 10/1995 | Pereira et al. | 424/85.1 |
| 5,459,235 | 10/1995 | Selsted et al. | 530/300 |
| 5,464,823 | 11/1995 | Lehrer et al. | 514/13 |
| 5,484,885 | 1/1996 | Pereira et al. | 530/326 |
| 5,693,486 | 12/1997 | Lehrer et al. | 435/69.1 |
| 5,708,145 | 1/1998 | Lehrer et al. | 530/387.1 |
| 5,804,558 | 9/1998 | Lehrer et al. | 514/13 |
| 5,994,306 | 11/1999 | Chang et al. | 514/13 |

FOREIGN PATENT DOCUMENTS

| | | |
|---|---|---|
| 545730 | 6/1993 | European Pat. Off. . |
| WO 91/00907 | 1/1991 | WIPO . |
| WO 94/02589 | 2/1994 | WIPO . |
| WO 94/28921 | 12/1994 | WIPO . |
| WO 95/03325 | 2/1995 | WIPO . |
| WO 95/26747 | 10/1995 | WIPO . |
| WO 96/04373 | 2/1996 | WIPO . |

_Primary Examiner_—Ponnathapu Achutamurthy
_Assistant Examiner_—William W. Moore
_Attorney, Agent, or Firm_—Pennie & Edmonds LLP

[57] ABSTRACT

Peptide-based compounds containing four invariant cysteine residues which have been optionally oxidized to contain two intramolecular disulfide bonds, or modified forms where the cysteines are replaced are useful as preservatives and in preventing, treating, or ameliorating viral or microbial infection in animals and plants, and in inactivating endotoxin. These compounds, in one embodiment, are of the formula:

$$A_1-A_2-A_3-A_4-A_5-A_6-A_7-A_8-A_9-A_{10}-A_{11}-A_{12}-A_{13}-A_{14}-A_{15}-A_{16}-(A_{17}-A_{18}) \quad (1)$$

and the N-terminal acylated and/or C-terminal amidated or esterified forms thereof, which is either in the optionally —SH stablizied linear or in a cystine-bridged form wherein each of $A_1$ and $A_9$ is independently a basic amino acid;

each of $A_2$ and $A_3$ is independently a small amino acid;

each of $A_5$, $A_7$, $A_{12}$, $A_{14}$ and $A_{16}$ is independently a hydrophobic amino acid;

$A_4$ is a basic or a small amino acid;

$A_{10}$ is a basic or a small amino acid or is proline;

$A_{11}$ is a basic or hydrophobic amino acid;

$A_{17}$ is not present or, if present, is a small amino acid;

$A_{18}$ is not present or, if present, is a basic amino acid; or a modified form of formula (1) and the N-terminal acylated and/or C-terminal amidated or esterified forms thereof wherein each of 1–4 cysteines is independently replaced by a hydrophobic amino acid or a small amino acid.

15 Claims, 27 Drawing Sheets

○ E. COLI
● L. MONOCYTOGENES
△ C. ALBICANS

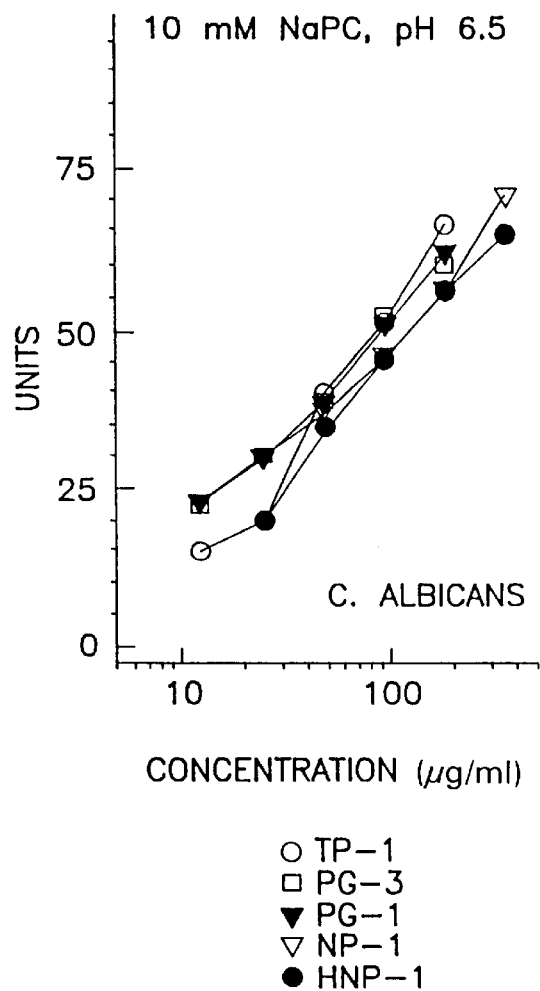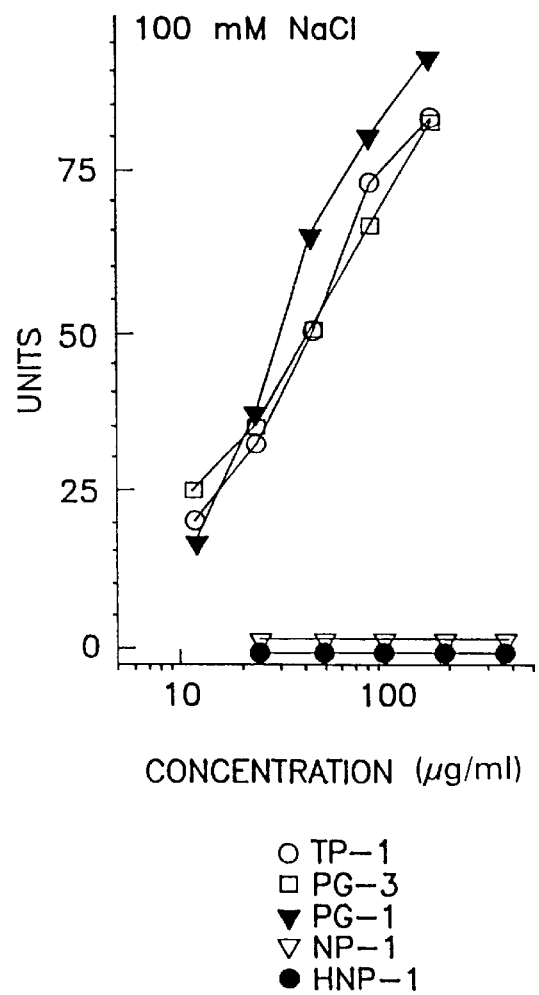
FIG. 5a-1  FIG. 5a-2

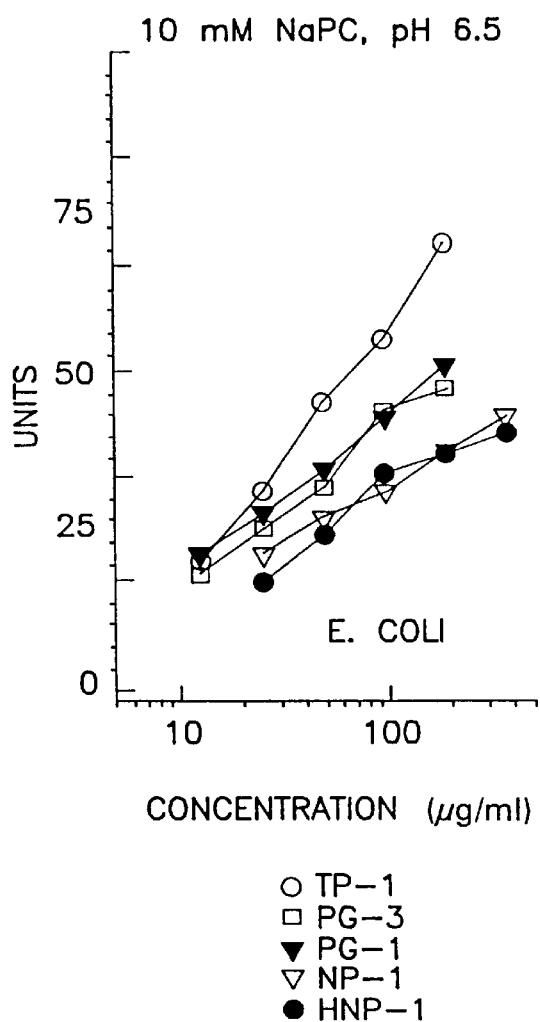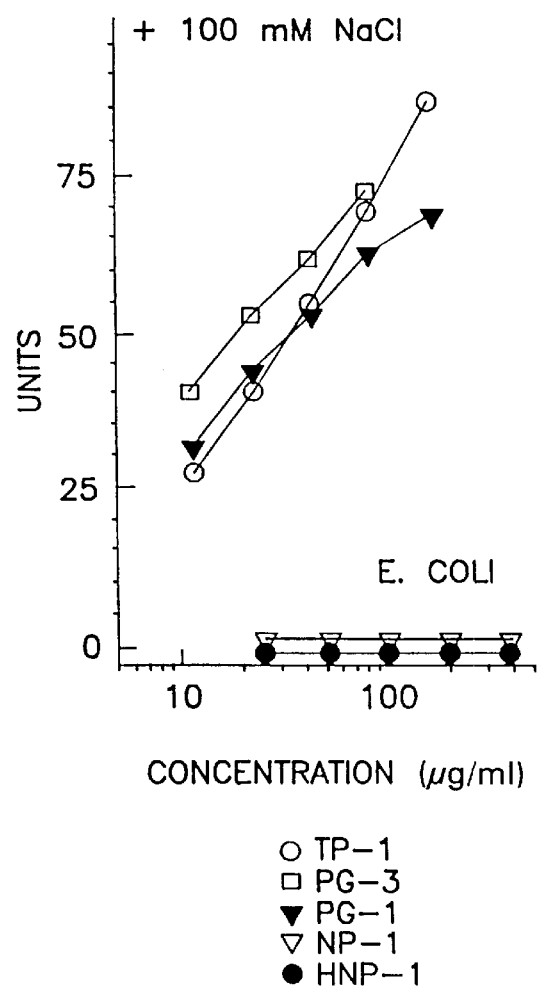
FIG. 5b-1   FIG. 5b-2

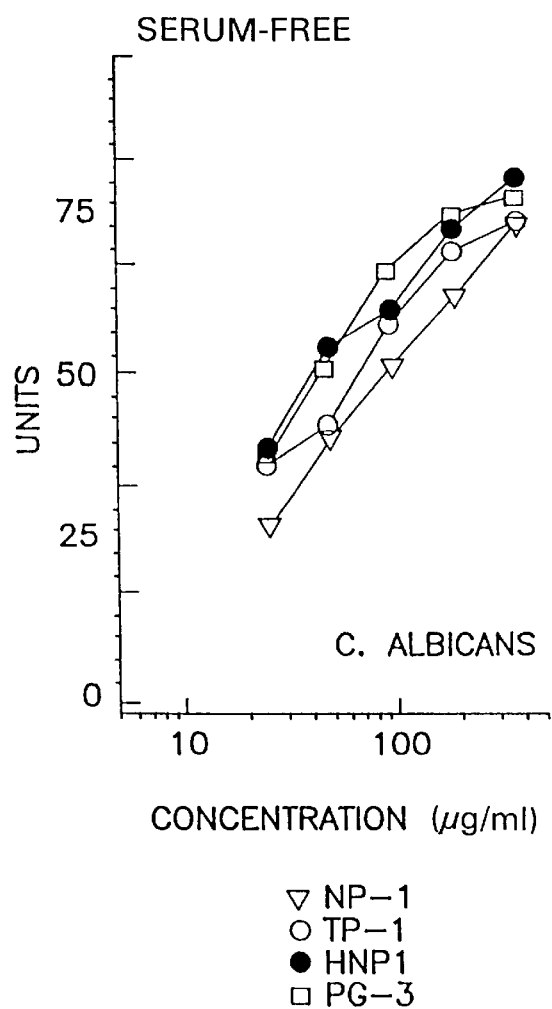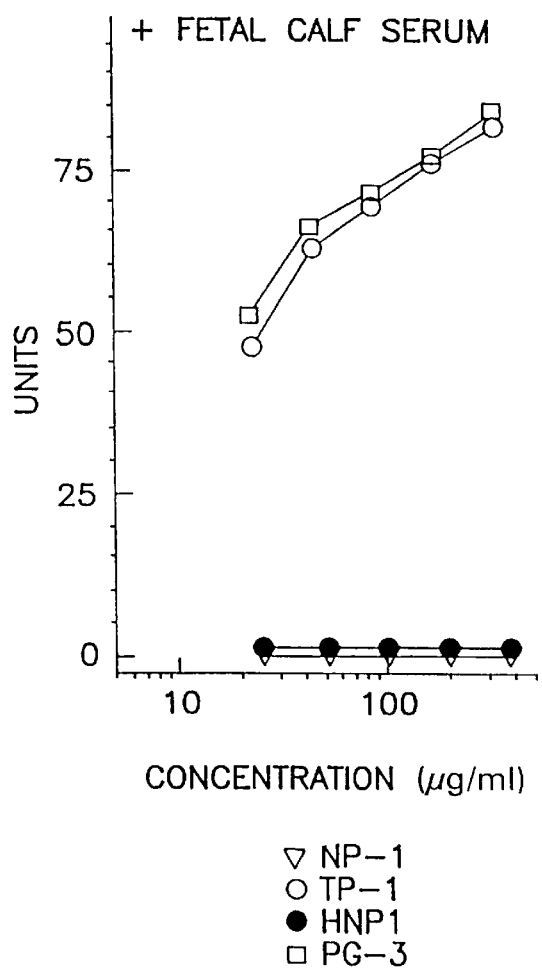
FIG. 5c-1  FIG. 5c-2

```
                10         20         30         40         50
      ATGGAGACCGAGAGAGCCAGCCTGTGCCTGGGGCGCTGGTCACTGTGGCTTCTGCTGCTG    60
      MetGluThrGlnArgAlaSerLeuCysLeuGlyArgTrpSerLeuTrpLeuLeuLeuLeu    20
      GCACTCGTGGTGCCCTCGGCCAGCGCCCAGGCCCTCAGCTACAGGGAGGCCGTGCTTCGT   120
      AlaLeuValValProSerAlaSerAlaGlnAlaLeuSerTyrArgGluAlaValLeuArg    40
      GCTGTGGATCGCCTCAACGAGCAGTCCTCGGAAGCTAATCTCTACCGCCTCCTGGAGCTG   180
      AlaValAspArgLeuAsnGluGlnSerSerGluAlaAsnLeuTyrArgLeuLeuGluLeu    60
      GACCAGCCGCCCAAGGCCGACGAGGACCCGGGCACCCCGAAACCTGTGAGCTTCACGGTG   240
      AspGlnProProLysAlaAspGluAspProGlyThrProLysProValSerPheThrVal    80
      AAGGAGACTGTGTGTCCCAGGCCGACCCGGCAGCCCCCGGAGCTGTGTGACTTCAAGGAG   300
      LysGluThrValCysProArgProThrArgGlnProProGluLeuCysAspPheLysGlu   100
      AACGGGCGGGTGAAACAGTGTGTGGGGACAGTCACCCTGGATCAGATCAAGGACCCGCTC   360
      AsnGlyArgValLysGlnCysValGlyThrValThrLeuAspGlnIleLysAspProLeu   120
                                                G3                G4
      GACATCACCTGCAATGAGGTTCAAGGTGTCAGGGGAGGTCGCCTGTGCTATTGTAGGCGT   420
      AspIleThrCysAsnGluValGlnGlyValArgGlyGlyArgLeuCysTyrCysArgArg   140
                                                Gly3          Gly4

A2
      T4 A4  T4      T2
      AGGTTCTGCGTCTGTGTCGGACGAGGATGACGGTTGCGACGGCAGGCTTTCCCTCCCCCA   480
      ArgPheCysValCysValGlyArgGly---                                149
      Trp4Ile4 Phe4        ---2
               Ile2

ATTTTCCCGGGGCCAGGTTTCCGTCCCCCAATTTTTCCGCCTCCACCTTTCCGGCCCGCA   540
                                A2 G2
      CCATTCGGTCCACCAAGGTTCCCTGGTAGACGGTGAAGGATTTGCAGGCAACTCACCCAG   600
            C4
      AAGGCCTTTCGGTACATTAAAATCCCAGCAAGGAGACCTAAGCATCTGCTTTGCCCAGGC   660
      CCGCATCTGTCAAATAAATTCTTGTGAAACC                                691
```

FIG. 7

```
ATGGAGACCCAGAGAGCCAGCCTGTGCCTGGGGCGCTGGTCACTGTGGCTTCTGCTGCTG    60
 M  E  T  Q  R  A  S  L  C  L  G  R  W  S  L  W  L  L  L  L
 G5
GCACTCGTGGTGCCCTCGGCCAGCGCCCAGGCCCTCAGCTACAGGGAGGCCGTGCTTCGT   120
 A  L  V  V  P  S  A  S  A  Q  A  L  S  Y  R  E  A  V  L  R
 G5
GCTGTGGATCGCCTCAACGAGCAGTCCTCGGAAGCTAATCTCTACCGCCTCCTGGAGCTG   180
 A  V  D  R  L  N  E  Q  S  S  E  A  N  L  Y  R  L  L  E  L
GACCAGCCGCCCAAGGCCgtgagtcgggcagggctcaggaggggctggggggcgggggc    240
 D  Q  P  P  K  A
tgtccccaccccgccccggggctccctgtccctcccctgctcaggctgtccctcctgcc    300
aggaaggcacttgtccctctaaggggggaccccctctgccaggaaaccttcccagagctgg  360
gtgccctgcccgcgtgagagcttcccgccttagcctctgggctgtgggctcagggccctg   420
cacagcctgtgaggcaggagcgggctctgtcccctcccctgtgcacccagcaccaagccc...480
agggccaggctcccagcaggggctgcagaggctgctgtctaggtgggggcggggagggg    540
tgacagatccgagggggaagcctgagcccgagtcccatctccccactttgatccttgacc   600
                 A5
agGACGAGGACCCGGGCACCCCGAAACCTGTGAGCTTCACGGTGAAGGAGACTGTGTGTC   660
   D  E  D  P  G  T  P  K  P  V  S  F  T  V  K  E  T  V  C
CCAGGCCGACCCGGCAGCCCCGGAGCTGTGTGACTTCAAGGAGAACGGGgtgaggctgg    720
 P  R  P  T  R  Q  P  P  E  L  C  D  F  K  E  N  G
gggctggggcgctggcggatgcttcccaaggagctgaacaggagagcctgctggggaag   780
atgtccaggccctggggtgaggctgggagctcatggatggaggagggggggtcccagttt   840
                t3
gaccttgagtctccccttccagCGGGTGAAACAGTGTGTGGGGACAGTCACCCTGGATCA   900
                       R  V  K  Q  C  V  G  T  V  T  L  D  Q
GATCAAGGACCCGCTCGACATCACCTGCAATGAGgtgagtggccccttattggtgtcaag   960
  I  K  D  P  L  D  I  T  C  N  E
ttgctaatgggttggtgtggggaactccttgggagtgttacccgctgccccatccagggc  1020
gtggaaaggccctcctaccccggcccttccctcacctcggccccagggctccaggtctgg  1080
ctctgtcatccttagggccgcggttccctcaatggggtcccccctcgtatttgtcagaa   1140
                                                     g3,5
aggcacatttcaggccccaccccgaccctctgaatcacactcttgggtggagcccagcct  1200
tgtctcttctcccaagatcccagcgggttcttcctgtgctgtcggctgagaggcagtgac  1260
cggactaatggacttgcaggccctgctcctggccagcttttgcggggctgggtttgggacc  1320
ctggcaaggccccagccatctctgggcctgagtccacttatgtgtctgtggggattcaa  1381
                                  g3,5
                                   t5
ccacgtgctccaaaggtcacagccagaggtggaccagggccccaagcctcttactgtttc  1440
```

FIG. 8a

```
cccattcagggattttttctagtctggagggagggttcttgtcttgacccttggccagacc  1500
                         G3
ccacccgaaacctgtttctcttggtcacagGTTCAAGGTGTCAGGGGAGGTCGCCTGTGC   1560
                                F  Q  G  V  R  G  G  R  L  C
                                                  G3
          C5                T5
TATTGTAGGCGTAGGTTCTGCGTCTGTGTCGGACGAGGATGACGGTTGCGACGGCAGGCT   1620
   Y  C  R  R  R  F  C  V  C  V  G  R  G ***
           P5
TTCCCTCCCCCAATTTTCCCGGGGCCAGGTTTCCGTCCCCCAATTTTTCCGCCTCCACCT   1680
TTCCGGCCCGCACCATTCGGTCCACCAAGGTTCCCTGGTAGACGGTGAAGGATTTGCAGG   1740
              C3,5
CAACTCACCCAGAAGGCCTTTCGGTACATTAAAATCCCAGCAAGGAGACCTAAGCATCTG   1800
CTTTGCCCAGGCCCGCATCTGTCAAATAAATTCTTGTGAAACC                    1843
```

FIG. 8b

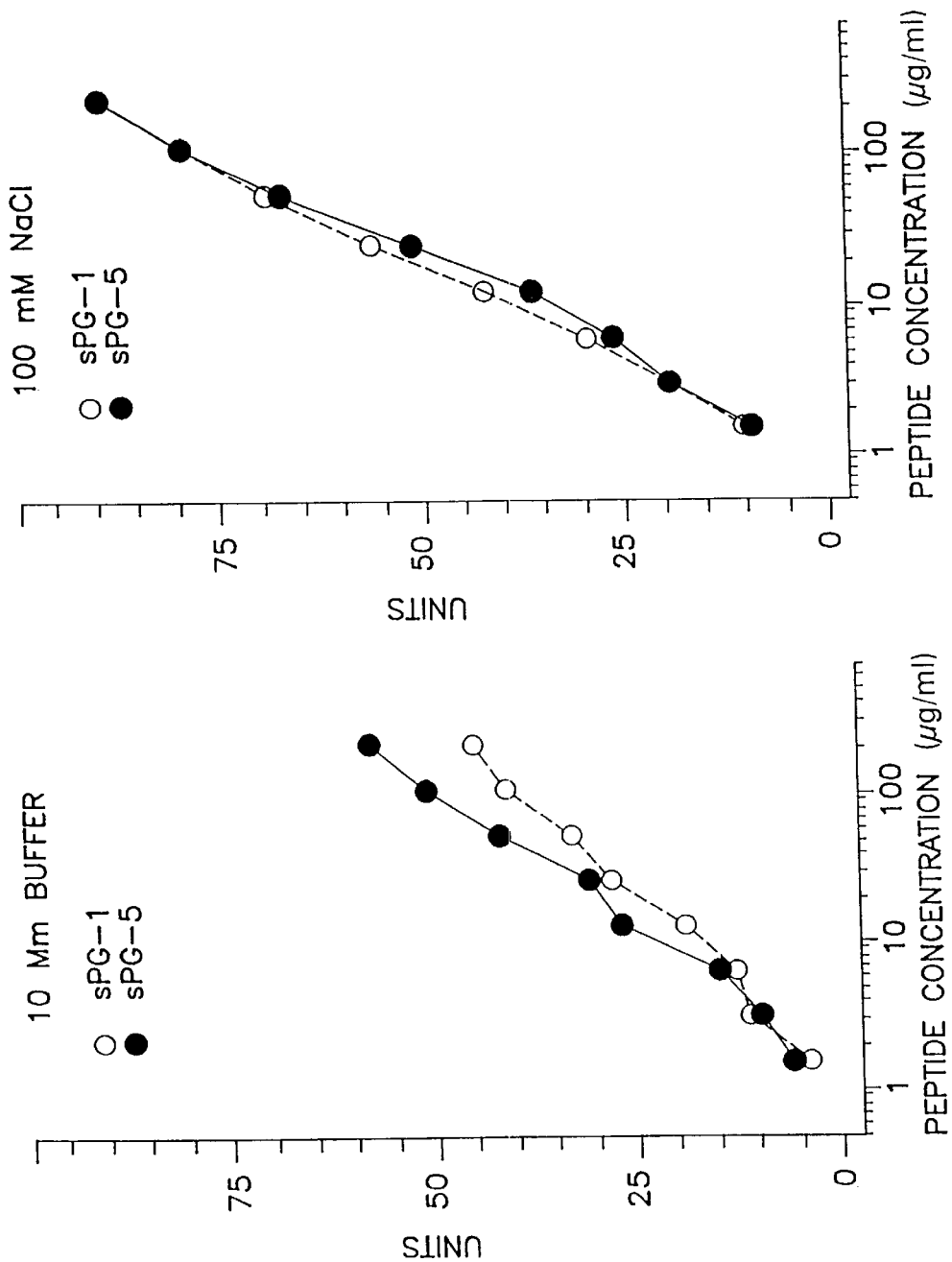
FIG. IIa-2
FIG. IIa-1

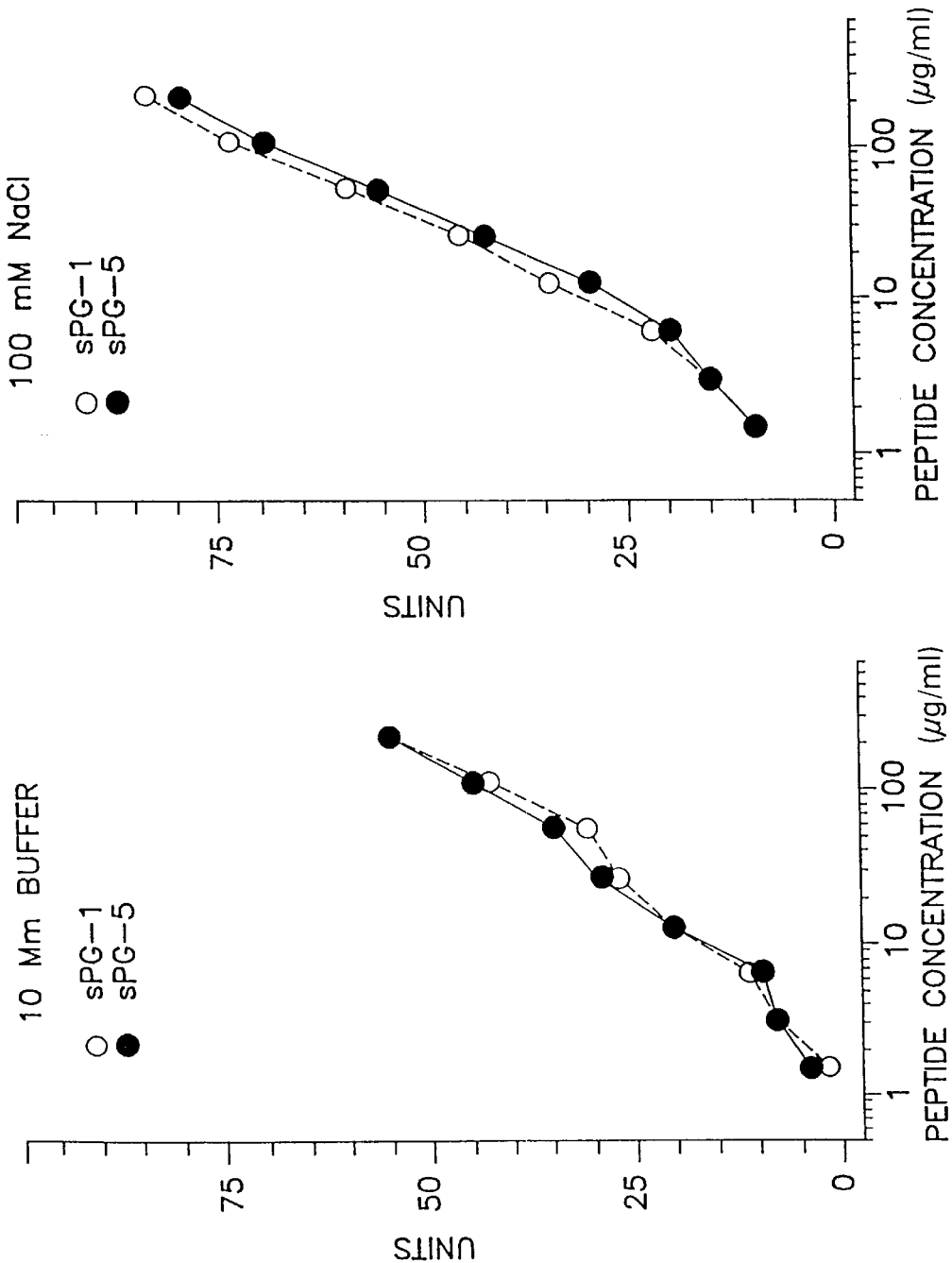
FIG. IIb-2
FIG. IIb-1

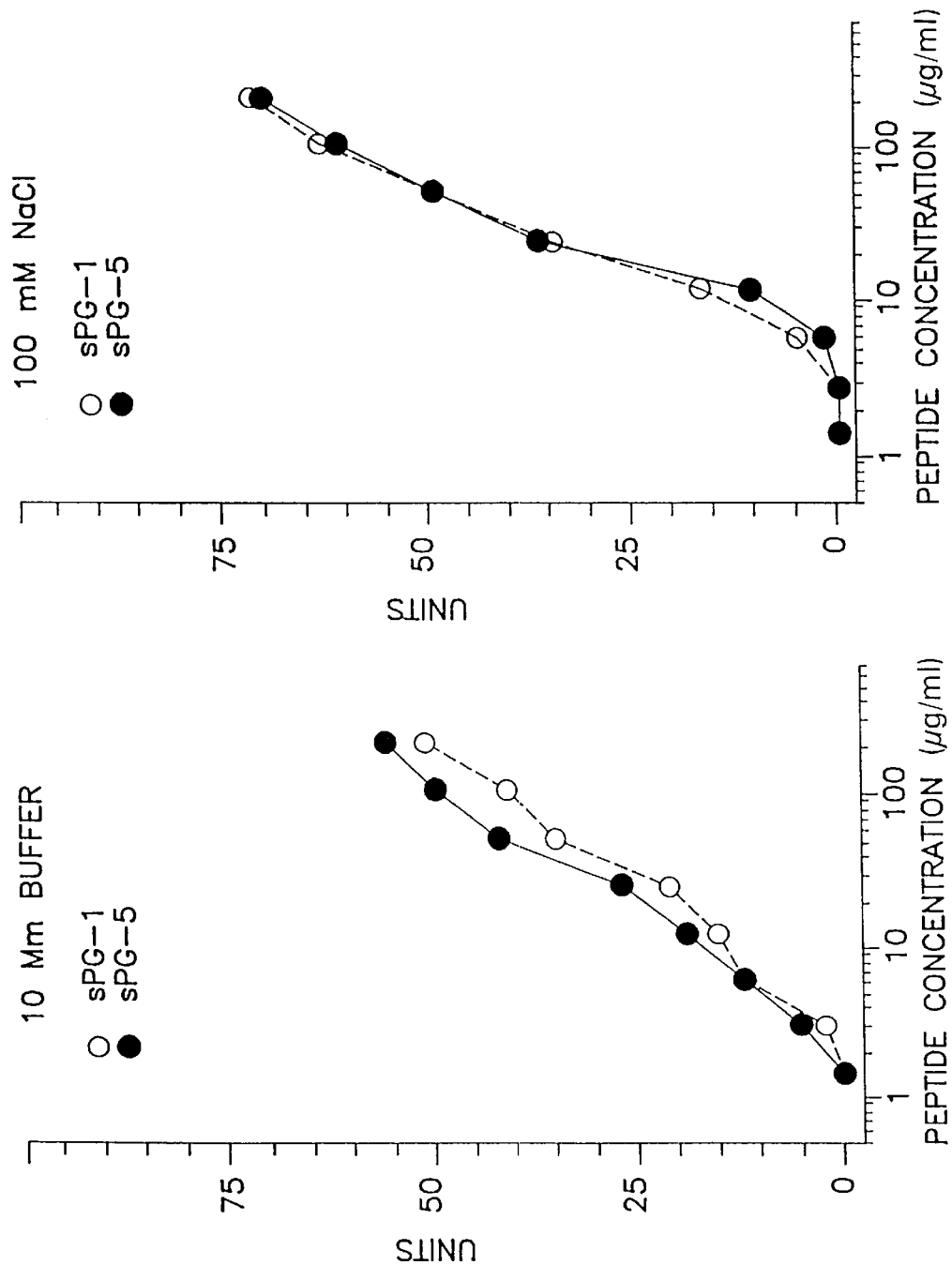
FIG. IIc-2
FIG. IIc-1

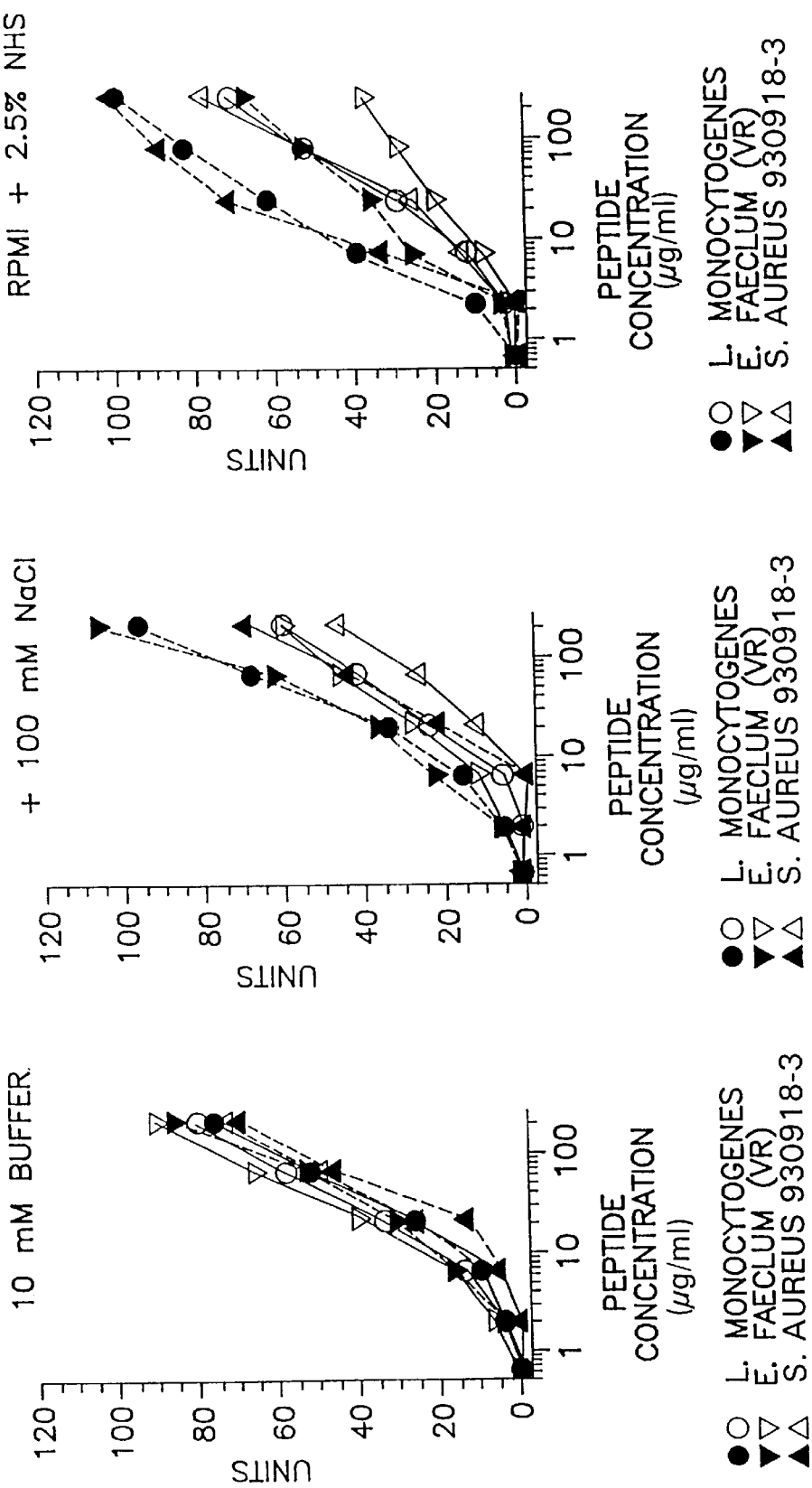

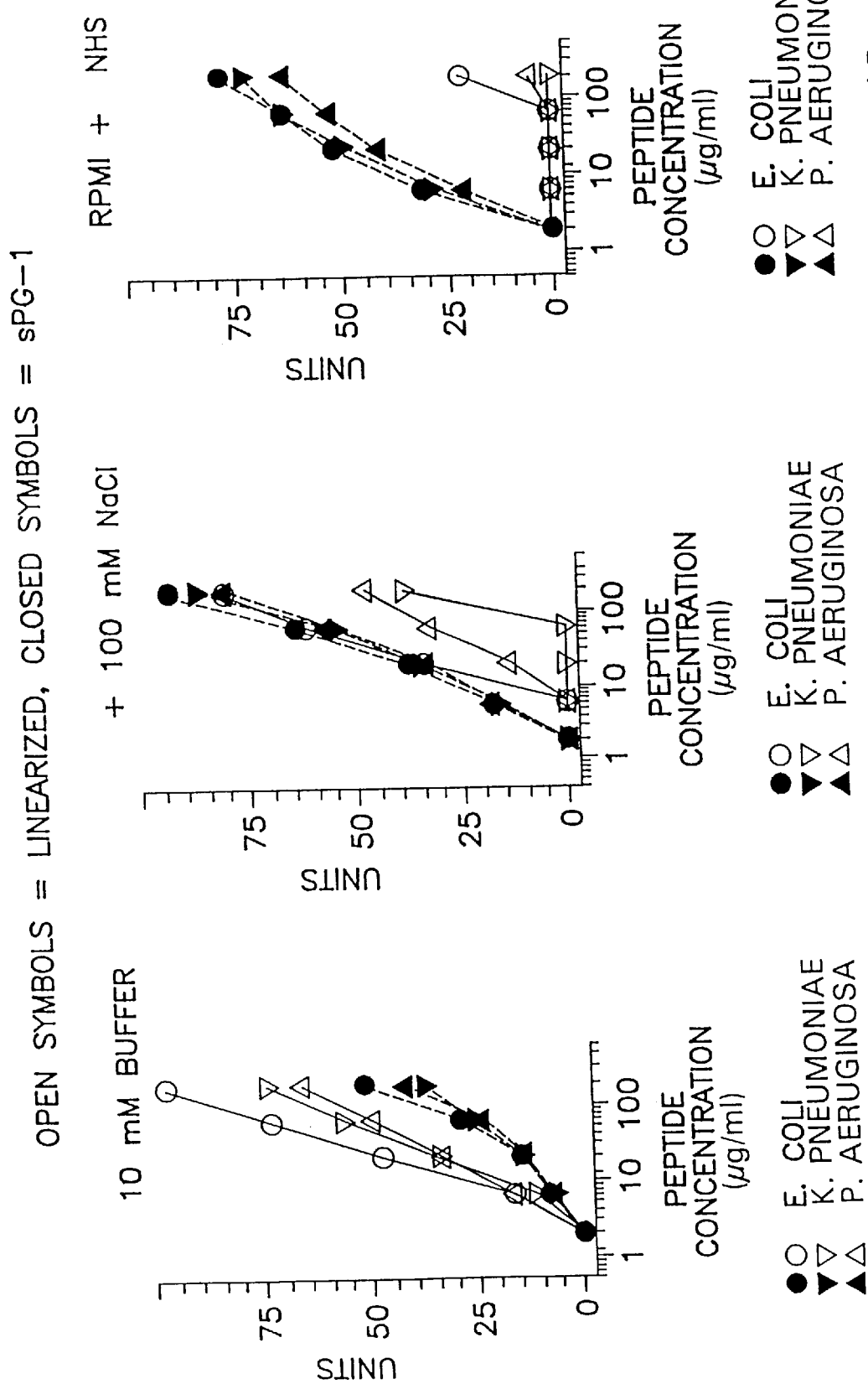

SEQUENCE LISTING (1) GENERAL INFORMATION:

(iii) NUMBER OF SEQUENCES: 76

(2) INFORMATION FOR SEQ ID NO:1:

(i) SEQUENCE CHARACTERISTICS:
      (A) LENGTH: 691 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 1..450

(xi) SEQUENCE DESCRIPTION: SEQ ID NO:1:

```
ATG GAG ACC CAG AGA GCC AGC CTG TGC CTG GGG CGC TGG TCA CTG TGG        48
Met Glu Thr Gln Arg Ala Ser Leu Cys Leu Gly Arg Trp Ser Leu Trp
 1               5                  10                  15

CTT CTG CTG CTG GCA CTC GTG GTG CCC TCG GCC AGC GCC CAG GCC CTC        96
Leu Leu Leu Leu Ala Leu Val Val Pro Ser Ala Ser Ala Gln Ala Leu
             20                  25                  30

AGC TAC AGG GAG GCC GTG CTT CGT GCT GTG GAT CGC CTC AAC GAG CAG       144
Ser Tyr Arg Glu Ala Val Leu Arg Ala Val Asp Arg Leu Asn Glu Gln
         35                  40                  45

TCC TCG GAA GCT AAT CTC TAC CGC CTC CTG GAG CTG GAC CAG CCG CCC       192
Ser Ser Glu Ala Asn Leu Tyr Arg Leu Leu Glu Leu Asp Gln Pro Pro
     50                  55                  60

AAG GCC GAC GAG GAC CCG GGC ACC CCG AAA CCT GTG AGC TTC ACG GTG       240
Lys Ala Asp Glu Asp Pro Gly Thr Pro Lys Pro Val Ser Phe Thr Val
 65                  70                  75                  80

AAG GAG ACT GTG TGT CCC AGG CCG ACC CGG CAG CCC CCG GAG CTG TGT       288
Lys Glu Thr Val Cys Pro Arg Pro Thr Arg Gln Pro Pro Glu Leu Cys
                 85                  90                  95

GAC TTC AAG GAG AAC GGG CGG GTG AAA CAG TGT GTG GGG ACA GTC ACC       336
Asp Phe Lys Glu Asn Gly Arg Val Lys Gln Cys Val Gly Thr Val Thr
            100                 105                 110

CTG GAT CAG ATC AAG GAC CCG CTC GAC ATC ACC TGC AAT GAG GTT CAA       384
Leu Asp Gln Ile Lys Asp Pro Leu Asp Ile Thr Cys Asn Glu Val Gln
        115                 120                 125

GGT GTC AGG GGA GGT CGC CTG TGC TAT TGT AGG CGT AGG TTC TGC GTC       432
Gly Val Arg Gly Gly Arg Leu Cys Tyr Cys Arg Arg Arg Phe Cys Val
    130                 135                 140

TGT GTC GGA CGA GGA TGA CGGTTGCGAC GGCAGGCTTT CCCTCCCCCA               480
Cys Val Gly Arg Gly *
145             150

ATTTTCCCGG GGCCAGGTTT CCGTCCCCCA ATTTTTCCGC CTCCACCTTT CCGGCCCGCA      540

CCATTCGGTC CACCAAGGTT CCCTGGTAGA CGGTGAAGGA TTTGCAGGCA ACTCACCCAG      600

AAGGCCTTTC GGTACATTAA AATCCCAGCA AGGAGACCTA AGCATCTGCT TGCCCAGGC       660

CCGCATCTGT CAAATAAATT CTTGTGAAAC C                                     691
```

(2) INFORMATION FOR SEQ ID NO:2:

(i) SEQUENCE CHARACTERISTICS:
      (A) LENGTH: 149 amino acids
      (B) TYPE: amino acid
      (D) TOPOLOGY: linear (ii) MOLECULE TYPE: protein (xi) SEQUENCE DESCRIPTION: SEQ ID NO:2:

```
Met Glu Thr Gln Arg Ala Ser Leu Cys Leu Gly Arg Trp Ser Leu Trp
 1               5                  10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
        115                 120                 125

Gly Val Arg Gly Gly Arg Leu Cys Tyr Cys Arg Arg Arg Phe Cys Val
    130                 135                 140

Cys Val Gly Arg Gly
145                 150
```

(2) INFORMATION FOR SEQ ID NO:3:

(i) SEQUENCE CHARACTERISTICS:
        (A) LENGTH: 691 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..444

(xi) SEQUENCE DESCRIPTION: SEQ ID NO:3:

```
ATG GAG ACC CAG AGA GCC AGC CTG TGC CTG GGG CGC TGG TCA CTG TGG        48
Met Glu Thr Gln Arg Ala Ser Leu Cys Leu Gly Arg Trp Ser Leu Trp
                155                 160                 165

CTT CTG CTG CTG GCA CTC GTG GTG CCC TCG GCC AGC GCC CAG GCC CTC        96
Leu Leu Leu Leu Ala Leu Val Val Pro Ser Ala Ser Ala Gln Ala Leu
            170                 175                 180

AGC TAC AGG GAG GCC GTG CTT CGT GCT GTG GAT CGC CTC AAC GAG CAG       144
Ser Tyr Arg Glu Ala Val Leu Arg Ala Val Asp Arg Leu Asn Glu Gln
        185                 190                 195

TCC TCG GAA GCT AAT CTC TAC CGC CTC CTG GAG CTG GAC CAG CCG CCC       192
Ser Ser Glu Ala Asn Leu Tyr Arg Leu Leu Glu Leu Asp Gln Pro Pro
    200                 205                 210

AAG GCC GAC GAG GAC CCG GGC ACC CCG AAA CCT GTG AGC TTC ACG GTG       240
Lys Ala Asp Glu Asp Pro Gly Thr Pro Lys Pro Val Ser Phe Thr Val
215                 220                 225                 230

AAG GAG ACT GTG TGT CCC AGG CCG ACC CGG CAG CCC CCG GAG CTG TGT       288
Lys Glu Thr Val Cys Pro Arg Pro Thr Arg Gln Pro Pro Glu Leu Cys
                235                 240                 245

GAC TTC AAG GAG AAC GGG CGG GTG AAA CAG TGT GTG GGG ACA GTC ACC       336
Asp Phe Lys Glu Asn Gly Arg Val Lys Gln Cys Val Gly Thr Val Thr
            250                 255                 260

CTG GAT CAG ATC AAG GAC CCG CTC GAC ATC ACC TGC AAT GAG GTT CAA       384
Leu Asp Gln Ile Lys Asp Pro Leu Asp Ile Thr Cys Asn Glu Val Gln
        265                 270                 275
```

```
GGT GTC AGG GGA GGT CGC CTG TGC TAT TGT AGG CGT AGG TTC TGC ATC      432
Gly Val Arg Gly Gly Arg Leu Cys Tyr Cys Arg Arg Arg Phe Cys Ile
        280                 285                 290

TGT GTC GGA TGA GGATGACGGT TGCGACGGCA GGCTTTCCCT CCCCCAATTT          484
Cys Val Gly *
295

TCCCGGGGCC AGGTTTCCGT CCCCCAATTT TTCCGCCTCC ACCTTTCCGG CCCGCACCAT    544

TCGGTCCACC AAGGTTCCCT GGTAGACGGA GAGGGATTTG CAGGCAACTC ACCCAGAAGG    604

CCTTTCGGTA CATTAAAATC CCAGCAAGGA GACCTAAGCA TCTGCTTTGC CCAGGCCCGC    664

ATCTGTCAAA TAAATTCTTG TGAAACC                                       691

(2) INFORMATION FOR SEQ ID NO:4:

(i) SEQUENCE CHARACTERISTICS:
        (A) LENGTH: 147 amino acids
        (B) TYPE: amino acid
        (D) TOPOLOGY: linear (ii) MOLECULE TYPE: protein (xi) SEQUENCE DESCRIPTION: SEQ ID NO:4:

Met Glu Thr Gln Arg Ala Ser Leu Cys Leu Gly Arg Trp Ser Leu Trp
 1               5                  10                  15

Leu Leu Leu Leu Ala Leu Val Val Pro Ser Ala Ser Ala Gln Ala Leu
            20                  25                  30

Ser Tyr Arg Glu Ala Val Leu Arg Ala Val Asp Arg Leu Asn Glu Gln
        35                  40                  45

Ser Ser Glu Ala Asn Leu Tyr Arg Leu Leu Glu Leu Asp Gln Pro Pro
    50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
        115                 120                 125

Gly Val Arg Gly Gly Arg Leu Cys Tyr Cys Arg Arg Arg Phe Cys Ile
    130                 135                 140

Cys Val Gly
145

(2) INFORMATION FOR SEQ ID NO:5:

(i) SEQUENCE CHARACTERISTICS:
        (A) LENGTH: 691 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..450

(xi) SEQUENCE DESCRIPTION: SEQ ID NO:5:

ATG GAG ACC CAG AGA GCC AGC CTG TGC CTG GGG CGC TGG TCA CTG TGG      48
Met Glu Thr Gln Arg Ala Ser Leu Cys Leu Gly Arg Trp Ser Leu Trp
150                 155                 160

CTT CTG CTG CTG GCA CTC GTG GTG CCC TCG GCC AGC GCC CAG GCC CTC      96
```

```
Leu Leu Leu Leu Ala Leu Val Val Pro Ser Ala Ser Ala Gln Ala Leu
165                 170                 175                 180

AGC TAC AGG GAG GCC GTG CTT CGT GCT GTG GAT CGC CTC AAC GAG CAG         144
Ser Tyr Arg Glu Ala Val Leu Arg Ala Val Asp Arg Leu Asn Glu Gln
                        185                 190                 195

TCC TCG GAA GCT AAT CTC TAC CGC CTC CTG GAG CTG GAC CAG CCG CCC         192
Ser Ser Glu Ala Asn Leu Tyr Arg Leu Leu Glu Leu Asp Gln Pro Pro
                200                 205                 210

AAG GCC GAC GAG GAC CCG GGC ACC CCG AAA CCT GTG AGC TTC ACG GTG         240
Lys Ala Asp Glu Asp Pro Gly Thr Pro Lys Pro Val Ser Phe Thr Val
            215                 220                 225

AAG GAG ACT GTG TGT CCC AGG CCG ACC CGG CAG CCC CCG GAG CTG TGT         288
Lys Glu Thr Val Cys Pro Arg Pro Thr Arg Gln Pro Pro Glu Leu Cys
        230                 235                 240

GAC TTC AAG GAG AAC GGG CGG GTG AAA CAG TGT GTG GGG ACA GTC ACC         336
Asp Phe Lys Glu Asn Gly Arg Val Lys Gln Cys Val Gly Thr Val Thr
245                 250                 255                 260

CTG GAT CAG ATC AAG GAC CCG CTC GAC ATC ACC TGC AAT GAG GTT CAA         384
Leu Asp Gln Ile Lys Asp Pro Leu Asp Ile Thr Cys Asn Glu Val Gln
                        265                 270                 275

GGT GTC AGG GGA GGT GGC CTG TGC TAT TGT AGG CGT AGG TTC TGC GTC         432
Gly Val Arg Gly Gly Gly Leu Cys Tyr Cys Arg Arg Arg Phe Cys Val
                280                 285                 290

TGT GTC GGA CGA GGA TGA CGGTTGCGAC GGCAGGCTTT CCCTCCCCCA                480
Cys Val Gly Arg Gly *
            295

ATTTTCCCGG GGCCAGGTTT CCGTCCCCCA ATTTTTCCGC CTCCACCTTT CCGGCCCGCA       540

CCATTCGGTC CACCAAGGTT CCCTGGTAGA CGGTGAAGGA TTTGCAGGCA ACTCACCCAG       600

AAGGCCTTTC GGTACATTAA AATCCCAGCA AGGAGACCTA AGCATCTGCT TTGCCCAGGC       660

CCGCATCTGT CAAATAAATT CTTGTGAAAC C                                      691

(2) INFORMATION FOR SEQ ID NO:6:

(i) SEQUENCE CHARACTERISTICS:
        (A) LENGTH:  149 amino acids
        (B) TYPE: amino acid
        (D) TOPOLOGY: linear (ii) MOLECULE TYPE: protein (xi) SEQUENCE DESCRIPTION: SEQ ID NO:6:

Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
                20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
        50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asp Gln Ile Lys Asp Pro Leu Asp Ile Thr Cys Asn Glu Val Gln
        115                 120                 125
```

```
Gly Val Arg Gly Gly Leu Cys Tyr Cys Arg Arg Phe Cys Val
    130                 135                 140

Cys Val Gly Arg Gly
145             150

(2) INFORMATION FOR SEQ ID NO:7:

(i) SEQUENCE CHARACTERISTICS:
        (A) LENGTH: 691 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..450

(xi) SEQUENCE DESCRIPTION: SEQ ID NO:7:

ATG GAG ACC CAG AGA GCC AGC CTG TGC CTG GGG CGC TGG TCA CTG TGG        48
Met Glu Thr Gln Arg Ala Ser Leu Cys Leu Gly Arg Trp Ser Leu Trp
                155                 160                 165

CTT CTG CTG CTG GCA CTC GTG GTG CCC TCG GCC AGC GCC CAG GCC CTC        96
Leu Leu Leu Leu Ala Leu Val Val Pro Ser Ala Ser Ala Gln Ala Leu
            170                 175                 180

AGC TAC AGG GAG GCC GTG CTT CGT GCT GTG GAT CGC CTC AAC GAG CAG       144
Ser Tyr Arg Glu Ala Val Leu Arg Ala Val Asp Arg Leu Asn Glu Gln
        185                 190                 195

TCC TCG GAA GCT AAT CTC TAC CGC CTC CTG GAG CTG GAC CAG CCG CCC       192
Ser Ser Glu Ala Asn Leu Tyr Arg Leu Leu Glu Leu Asp Gln Pro Pro
    200                 205                 210

AAG GCC GAC GAG GAC CCG GGC ACC CCG AAA CCT GTG AGC TTC ACG GTG       240
Lys Ala Asp Glu Asp Pro Gly Thr Pro Lys Pro Val Ser Phe Thr Val
215                 220                 225                 230

AAG GAG ACT GTG TGT CCC AGG CCG ACC CGG CAG CCC CCG GAG CTG TGT       288
Lys Glu Thr Val Cys Pro Arg Pro Thr Arg Gln Pro Pro Glu Leu Cys
                235                 240                 245

GAC TTC AAG GAG AAC GGG CGG GTG AAA CAG TGT GTG GGG ACA GTC ACC       336
Asp Phe Lys Glu Asn Gly Arg Val Lys Gln Cys Val Gly Thr Val Thr
            250                 255                 260

CTG GAT CAG ATC AAG GAC CCG CTC GAC ATC ACC TGC AAT GAG GTT CAA       384
Leu Asp Gln Ile Lys Asp Pro Leu Asp Ile Thr Cys Asn Glu Val Gln
        265                 270                 275

GGT GTC AGG GGA GGT CGC CTG TGC TAT TGT AGG GGT TGG ATC TGC TTC       432
Gly Val Arg Gly Gly Arg Leu Cys Tyr Cys Arg Gly Trp Ile Cys Phe
    280                 285                 290

TGT GTC GGA CGA GGA TGA CGGTTGCGAC GGCAGGCTTT CCCTCCCCCA              480
Cys Val Gly Arg Gly *
295                 300

ATTTTCCCGG GGCCAGGTTT CCGTCCCCCA ATTTTTCCGC CTCCACCTTT CCGGCCCGCA     540

CCATTCGGTC CACCAAGGTT CCCTGGTAGA CGGTGAAGGA TTTGCAGGCA ACTCACCCAG     600

AAGGCCTTTC GGCACATTAA AATCCCAGCA AGGAGACCTA AGCATCTGCT TTGCCCAGGC     660

CCGCATCTGT CAAATAAATT CTTGTGAAAC C                                    691

(2) INFORMATION FOR SEQ ID NO:8:

(i) SEQUENCE CHARACTERISTICS:
        (A) LENGTH: 149 amino acids
        (B) TYPE: amino acid
        (D) TOPOLOGY: linear (ii) MOLECULE TYPE: protein
```

(xi) SEQUENCE DESCRIPTION: SEQ ID NO:8:

```
Met Glu Thr Gln Arg Ala Ser Leu Cys Leu Gly Arg Trp Ser Leu Trp
1               5                   10                  15

Leu Leu Leu Leu Ala Leu Val Val Pro Ser Ala Ser Ala Gln Ala Leu
                20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
        50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
                100                 105                 110

Leu Asp Gln Ile Lys Asp Pro Leu Asp Ile Thr Cys Asn Glu Val Gln
            115                 120                 125

Gly Val Arg Gly Arg Leu Cys Tyr Cys Arg Gly Trp Ile Cys Phe
        130                 135                 140

Cys Val Gly Arg Gly
145             150
```

(2) INFORMATION FOR SEQ ID NO:9:

(i) SEQUENCE CHARACTERISTICS:
        (A) LENGTH: 1843 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: join(1..198, 603..710, 863..934, 1531..1602)

(xi) SEQUENCE DESCRIPTION: SEQ ID NO:9:

```
ATG GAG ACC CAG AGA GCC AGC CTG TGC CTG GGG CGC TGG TCA CTG TGG        48
Met Glu Thr Gln Arg Ala Ser Leu Cys Leu Gly Arg Trp Ser Leu Trp
1               5                   10                  15

CTT CTG CTG CTG GCA CTC GTG GTG CCC TCG GCC AGC GCC CAG GCC CTC        96
Leu Leu Leu Leu Ala Leu Val Val Pro Ser Ala Ser Ala Gln Ala Leu
                20                  25                  30

AGC TAC AGG GAG GCC GTG CTT CGT GCT GTG GAT CGC CTC AAC GAG CAG       144
Ser Tyr Arg Glu Ala Val Leu Arg Ala Val Asp Arg Leu Asn Glu Gln
            35                  40                  45

TCC TCG GAA GCT AAT CTC TAC CGC CTC CTG GAG CTG GAC CAG CCG CCC       192
Ser Ser Glu Ala Asn Leu Tyr Arg Leu Leu Glu Leu Asp Gln Pro Pro
        50                  55                  60

AAG GCC GTGAGTCGGG CAGGGGCTCA GGAGGGGCTG GGGGGCGGGG GCTGTCCCCC       248
Lys Ala
65

ACCCGCCCCG GGGCTCCCTG TCCCTCCCCC TGCTCAGGCT GTCCCTCCTG CCAGGAAGGC     308

ACTTGTCCCT CTAAGGGGGA CCCCCTCTGC CAGGAAACCT TCCCAGAGCT GGGTGCCCTG     368

CCCGCGTGAG AGCTTCCCGC CTTAGCCTCT GGGCTGTGGG CTCAGGGCCC TGCACAGCCT     428

GTGAGGCAGG AGCGGGCTCT GTCCCCTCCC CTGTGCACCC AGCACCAAGC CCAGGGCCAG     488

GCTCCCAGCA GGGGCTGCAG AGGCTGCTGT CTAGGTGGGG GCGGGGAGGG GGTGACAGAT     548
```

```
CCGAGGGGGA AGCCTGAGCC CGAGTCCCAT CTCCCCACTT TGATCCTTGA CCAG GAC      605
                                                            Asp

GAG GAC CCG GGC ACC CCG AAA CCT GTG AGC TTC ACG GTG AAG GAG ACT      653
Glu Asp Pro Gly Thr Pro Lys Pro Val Ser Phe Thr Val Lys Glu Thr
        70                  75                  80

GTG TGT CCC AGG CCG ACC CGG CAG CCC CCG GAG CTG TGT GAC TTC AAG      701
Val Cys Pro Arg Pro Thr Arg Gln Pro Pro Glu Leu Cys Asp Phe Lys
    85                  90                  95

GAG AAC GGG GTGAGGCTGG GGGCTGGGGG CGCTGGCGGA TGCTTCCCAA              750
Glu Asn Gly
100

GGAGCTGAAC AGGAGAGCCT GCTGGGGAAG ATGTCCAGGC CCTGGGGTGA GGCTGGGAGC    810

TCATGGATGG AGGAGGGGGG GTCCCAGTTT GACCTTGAGT CTCCCCTTCC AG CGG        865
                                                         Arg

GTG AAA CAG TGT GTG GGG ACA GTC ACC CTG GAT CAG ATC AAG GAC CCG      913
Val Lys Gln Cys Val Gly Thr Val Thr Leu Asp Gln Ile Lys Asp Pro
        105                 110                 115

CTC GAC ATC ACC TGC AAT GAG GTGAGTGGCC CCTTATTGGT GTCAAGTTGC         964
Leu Asp Ile Thr Cys Asn Glu
120             125

TAATGGGTTG GTGTGGGGAA CTCCTTGGGA GTGTTACCCG CTGCCCCATC CAGGGCGTGG    1024

AAAGGCCCTC CTACCCCGGC CCTTCCCTCA CCTCGGCCCC AGGGCTCCAG GTCTGGCTCT    1084

GTCATCCTTA GGGCCGCGGT TCCCTCAATG GGGTCCCCCC CTCGTATTTG TCAGAAAGGC    1144

ACATTTCAGG CCCCACCCCG ACCCTCTGAA TCACACTCTT GGGTGGAGCC CAGCCTTGTC    1204

TCTTCTCCCA AGATCCCAGC GGGTTCTTCC TGTGCTGTCG GCTGAGAGGC AGTGACCGGA    1264

CTAATGGACT TGCAGGCCCT GCTCCTGGCC AGCTTTGCGG GGCTGGGTTT GGGACCCTGG    1324

CAAGGCCCCA GCCATCTCTG GGCCTGAGTC CACTTATGTG TCTGTGGGGG ATTCCACCAC    1384

GTGCTCCAAA GGTCACAGCC AGAGGTGGAC CAGGGCCCCA AGCCTCTTAC TGTTTCCCCA    1444

TTCAGGGATT TTTCTAGTCT GGAGGGAGGG TTCTTGTCTT GACCCTTGGC CAGACCCCAC    1504

CCGAAACCTG TTTCTCTTGG TCACAG GTT CAA GGT GTC AGG GGA GGT CGC CTG    1557
                           Val Gln Gly Val Arg Gly Gly Arg Leu
                                           130                 135

TGC TAT TGT AGG CGT AGG TTC TGC GTC TGT GTC GGA CGA GGA TGA         1602
Cys Tyr Cys Arg Arg Arg Phe Cys Val Cys Val Gly Arg Gly *
        140                 145                 150

CGGTTGCGAC GGCAGGCTTT CCCTCCCCCA ATTTTCCCGG GGCCAGGTTT CCGTCCCCCA    1662

ATTTTTCCGC CTCCACCTTT CCGGCCCGCA CCATTCGGTC CACCAAGGTT CCCTGGTAGA    1722

CGGTGAAGGA TTTGCAGGCA ACTCACCCAG AAGGCCTTTC GGTACATTAA AATCCCAGCA    1782

AGGAGACCTA AGCATCTGCT TGCCCAGGC CCGCATCTGT CAAATAAATT CTTGTGAAAC     1842

C                                                                    1843

(2) INFORMATION FOR SEQ ID NO:10:

(i) SEQUENCE CHARACTERISTICS:
        (A) LENGTH: 149 amino acids
        (B) TYPE: amino acid
        (D) TOPOLOGY: linear (ii) MOLECULE TYPE: protein (xi) SEQUENCE DESCRIPTION: SEQ ID NO:10:

Met Glu Thr Gln Arg Ala Ser Leu Cys Leu Gly Arg Trp Ser Leu Trp
 1               5                  10                  15
```

```
Leu Leu Leu Leu Ala Leu Val Val Pro Ser Ala Ser Ala Gln Ala Leu
             20                  25                  30

Ser Tyr Arg Glu Ala Val Leu Arg Ala Val Asp Arg Leu Asn Glu Gln
         35                  40                  45

Ser Ser Glu Ala Asn Leu Tyr Arg Leu Leu Glu Leu Asp Gln Pro Pro
     50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                 85                  90                  95

Asp Phe Lys Glu Asn Gly Arg Val Lys Gln Cys Val Gly Thr Val Thr
             100                 105                 110

Leu Asp Gln Ile Lys Asp Pro Leu Asp Ile Thr Cys Asn Glu Val Gln
             115                 120                 125

Gly Val Arg Gly Gly Arg Leu Cys Tyr Cys Arg Arg Phe Cys Val
         130                 135                 140

Cys Val Gly Arg Gly
145             150

(2) INFORMATION FOR SEQ ID NO:11:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
         (A) NAME/KEY: Disulfide-bond
         (B) LOCATION: 4..13

(ix) FEATURE:
         (A) NAME/KEY: Disulfide-bond
         (B) LOCATION: 6..11

(xi) SEQUENCE DESCRIPTION: SEQ ID NO:11:

Arg Gly Gly Arg Leu Cys Tyr Cys Arg Arg Phe Cys Val Cys Val
1               5                   10                  15

Gly Arg (2) INFORMATION FOR SEQ ID NO:12:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:12:

Arg Gly Gly Arg Leu Cys Tyr Cys Arg Arg Phe Cys Ile Cys Val
1               5                   10                  15

(2) INFORMATION FOR SEQ ID NO:13:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:13:

Arg Gly Gly Gly Leu Cys Tyr Cys Arg Arg Phe Cys Val Cys Val
1               5                   10                  15
```

Gly Arg (2) INFORMATION FOR SEQ ID NO:14:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:14:

```
Arg Gly Gly Arg Leu Cys Tyr Cys Arg Gly Trp Ile Cys Phe Cys Val
1               5                   10                  15
Gly Arg
```

(2) INFORMATION FOR SEQ ID NO:15:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:15:

```
Arg Phe Phe Arg Leu Cys Tyr Cys Arg Pro Arg Phe Cys Val Cys Val
1               5                   10                  15
Gly Arg
```

(2) INFORMATION FOR SEQ ID NO:16:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:16:

```
Arg Gly Gly Arg Leu Cys Tyr Cys Arg Arg Arg Phe Cys Val Cys Val
1               5                   10                  15
Gly Arg
```

(2) INFORMATION FOR SEQ ID NO:17:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:17:

```
Arg Gly Gly Arg Leu Cys Tyr Cys Arg Arg Arg Phe Cys Ile Cys Val
1               5                   10                  15
```

(2) INFORMATION FOR SEQ ID NO:18:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:18:

```
Arg Gly Gly Gly Leu Cys Tyr Cys Arg Arg Arg Phe Cys Val Cys Val
1               5                   10                  15
Gly Arg
```

(2) INFORMATION FOR SEQ ID NO:19:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:19:

```
Arg Gly Gly Arg Leu Cys Tyr Cys Arg Gly Trp Ile Cys Phe Cys Val
1               5                   10                  15
Gly Arg
```

(2) INFORMATION FOR SEQ ID NO:20:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:20:

```
Arg Gly Gly Arg Leu Cys Tyr Cys Arg Pro Arg Phe Cys Val Cys Val
1               5                   10                  15
Gly Arg
```

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:21:

```
Arg Gly Gly Arg Leu Cys Tyr Cys Arg Arg Arg Phe Cys Val Cys Val
1               5                   10                  15
```

(2) INFORMATION FOR SEQ ID NO:22:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:22:

```
Lys Gly Gly Arg Leu Cys Tyr Cys Arg Arg Arg Phe Cys Val Cys Val
1               5                   10                  15
```

(2) INFORMATION FOR SEQ ID NO:23:

(i) SEQUENCE CHARACTERISTICS:
        (A) LENGTH: 16 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 4
        (D) OTHER INFORMATION: /product= "homoarginine(Har)"

(xi) SEQUENCE DESCRIPTION: SEQ ID NO:23:

```
Arg Gly Gly Xaa Leu Cys Tyr Cys Arg Arg Arg Phe Cys Val Cys Val
1               5                   10                  15
```

(2) INFORMATION FOR SEQ ID NO:24:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(4, 9)
        (D) OTHER INFORMATION: /product= "homoarginine(Har)"

(xi) SEQUENCE DESCRIPTION: SEQ ID NO:24:

```
Arg Gly Gly Xaa Leu Cys Tyr Cys Xaa Arg Arg Phe Cys Val Cys Val
1               5                   10                  15
Gly Arg
```

(2) INFORMATION FOR SEQ ID NO:25:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"

(xi) SEQUENCE DESCRIPTION: SEQ ID NO:25:

```
Arg Gly Gly Arg Val Cys Tyr Cys Arg Xaa Arg Phe Cys Val Cys Val
1               5                   10                  15
Gly Arg
```

(2) INFORMATION FOR SEQ ID NO:26:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:26:

```
Arg Gly Gly Arg Leu Cys Tyr Cys Arg Lys Lys Trp Cys Val Cys Val
1               5                   10                  15
Gly Arg
```

(2) INFORMATION FOR SEQ ID NO:27:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"

(xi) SEQUENCE DESCRIPTION: SEQ ID NO:27:

```
Arg Gly Gly Arg Leu Cys Tyr Cys Arg Xaa Arg Tyr Cys Val Cys Val
1               5                   10                  15
Gly Arg
```

(2) INFORMATION FOR SEQ ID NO:28:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:28:

```
Arg Gly Ser Gly Leu Cys Tyr Cys Arg Arg Lys Trp Cys Val Cys Val
1               5                   10                  15

Gly Arg
```

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:29:

```
Arg Ala Thr Arg Ile Cys Phe Cys Arg Arg Phe Cys Val Cys Val
1               5                   10                  15

Gly Arg
```

(2) INFORMATION FOR SEQ ID NO:30:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"

(xi) SEQUENCE DESCRIPTION: SEQ ID NO:30:

```
Arg Gly Gly Lys Val Cys Tyr Cys Arg Xaa Arg Phe Cys Val Cys Val
1               5                   10                  15

Gly Arg
```

(2) INFORMATION FOR SEQ ID NO:31:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 9
        (D) OTHER INFORMATION: /note= "D-form of amino acid"

(ix) FEATURE:
        (A) NAME/KEY: Modified-site
        (B) LOCATION: 18
        (D) OTHER INFORMATION: /note= "D form of amino acid"

(xi) SEQUENCE DESCRIPTION: SEQ ID NO:31:

```
Arg Ala Thr Arg Ile Cys Phe Cys Arg Arg Phe Cys Val Cys Val
1               5                   10                  15

Gly Arg
```

(2) INFORMATION FOR SEQ ID NO:32:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"
            /note= "D form of amino acid"

(xi) SEQUENCE DESCRIPTION: SEQ ID NO:32:

```
Arg Gly Gly Lys Val Cys Tyr Cys Arg Xaa Arg Phe Cys Val Cys Val
1               5                   10                  15

Gly Arg
```

(2) INFORMATION FOR SEQ ID NO:33:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..18
        (D) OTHER INFORMATION: /note= "All D-form amino acids"

(xi) SEQUENCE DESCRIPTION: SEQ ID NO:33:

```
Arg Gly Gly Arg Leu Cys Tyr Cys Arg Arg Arg Phe Cys Val Cys Val
1               5                   10                  15

Gly Arg
```

(2) INFORMATION FOR SEQ ID NO:34:

(i) SEQUENCE CHARACTERISTICS:
        (A) LENGTH: 16 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..16
        (D) OTHER INFORMATION: /note= "All D-form amino acids"

(xi) SEQUENCE DESCRIPTION: SEQ ID NO:34:

```
Arg Gly Gly Arg Leu Cys Tyr Cys Arg Arg Arg Phe Cys Ile Cys Val
1               5                   10                  15
```

(2) INFORMATION FOR SEQ ID NO:35:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..18
        (D) OTHER INFORMATION: /note= "All D-form amino acids"

(xi) SEQUENCE DESCRIPTION: SEQ ID NO:35:

```
Arg Gly Gly Gly Leu Cys Tyr Cys Arg Arg Phe Cys Val Cys Val
1               5                   10                  15

Gly Arg
```

(2) INFORMATION FOR SEQ ID NO:36:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..18
        (D) OTHER INFORMATION: /note= "All D-form amino acids"

(xi) SEQUENCE DESCRIPTION: SEQ ID NO:36:

```
Arg Gly Gly Arg Leu Cys Tyr Cys Arg Gly Trp Ile Cys Phe Cys Val
1               5                   10                  15

Gly Arg
```

(2) INFORMATION FOR SEQ ID NO:37:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:37:

```
Arg Gly Gly Arg Leu Val Tyr Cys Arg Arg Phe Cys Val Cys Val
1               5                   10                  15

Gly Arg
```

(2) INFORMATION FOR SEQ ID NO:38:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:38:

```
Arg Gly Gly Arg Leu Gly Tyr Cys Arg Arg Phe Cys Ile Cys Val
1               5                   10                  15
```

(2) INFORMATION FOR SEQ ID NO:39:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:39:

```
Arg Gly Gly Gly Leu Cys Tyr Gly Arg Arg Phe Cys Val Cys Val
1               5                   10                  15

Gly Arg
```

(2) INFORMATION FOR SEQ ID NO:40:

(i) SEQUENCE CHARACTERISTICS:
        (A) LENGTH: 16 amino acids
        (B) TYPE: amino acid
        (C) STRANDEDNESS: single (D) TOPOLOGY: linear (xi) SEQUENCE DESCRIPTION: SEQ ID NO:40:

Arg Gly Gly Arg Leu Gly Tyr Gly Arg Arg Phe Gly Val Cys Val
1               5                   10                  15

(2) INFORMATION FOR SEQ ID NO:41:

(i) SEQUENCE CHARACTERISTICS:
            (A) LENGTH: 16 amino acids
            (B) TYPE: amino acid
            (C) STRANDEDNESS: single
            (D) TOPOLOGY: linear (xi) SEQUENCE DESCRIPTION: SEQ ID NO:41:

Lys Gly Gly Arg Leu Val Tyr Val Arg Arg Phe Ile Val Cys Val
1               5                   10                  15

(2) INFORMATION FOR SEQ ID NO:42:

(i) SEQUENCE CHARACTERISTICS:
            (A) LENGTH: 16 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 4
            (D) OTHER INFORMATION: /product= "homoarginine(Har)"

(xi) SEQUENCE DESCRIPTION: SEQ ID NO:42:

Arg Gly Gly Xaa Leu Cys Tyr Cys Arg Arg Arg Phe Cys Val Gly Val
1               5                   10                  15

(2) INFORMATION FOR SEQ ID NO:43:

(i) SEQUENCE CHARACTERISTICS:
            (A) LENGTH: 18 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: group(4, 9)
            (D) OTHER INFORMATION: /product= "homoarginine(Har)"

(xi) SEQUENCE DESCRIPTION: SEQ ID NO:43:

Arg Gly Gly Xaa Leu Cys Tyr Cys Xaa Arg Arg Phe Cys Val Leu Val
1               5                   10                  15

Gly Arg (2) INFORMATION FOR SEQ ID NO:44:

(i) SEQUENCE CHARACTERISTICS:
            (A) LENGTH: 18 amino acids
            (B) TYPE: amino acid
            (C) STRANDEDNESS: single
            (D) TOPOLOGY: linear (ix) FEATURE:
            (A) NAME/KEY: Modified-site
            (B) LOCATION: 10
            (D) OTHER INFORMATION: /product= "homoarginine(Har)"

(xi) SEQUENCE DESCRIPTION: SEQ ID NO:44:

Arg Gly Gly Arg Val Cys Tyr Val Arg Xaa Arg Phe Leu Val Gly Val
1               5                   10                  15

Gly Arg (2) INFORMATION FOR SEQ ID NO:45:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:45:

```
Arg Gly Gly Arg Leu Cys Tyr Ser Arg Lys Lys Trp Cys Val Ser Val
1               5                   10                  15
Gly Arg
```

(2) INFORMATION FOR SEQ ID NO:46:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"

(xi) SEQUENCE DESCRIPTION: SEQ ID NO:46:

```
Arg Gly Gly Arg Leu Cys Tyr Cys Arg Xaa Arg Tyr Ser Val Val Val
1               5                   10                  15
Gly Arg
```

(2) INFORMATION FOR SEQ ID NO:47:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:47:

```
Arg Gly Ser Gly Leu Ser Tyr Cys Arg Arg Lys Trp Gly Val Cys Val
1               5                   10                  15
Gly Arg
```

(2) INFORMATION FOR SEQ ID NO:48:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:48:

```
Arg Ala Thr Arg Ile Ser Phe Ser Arg Arg Arg Phe Ser Val Ser Val
1               5                   10                  15
Gly Arg
```

(2) INFORMATION FOR SEQ ID NO:49:

(i) SEQUENCE CHARACTERISTICS:
        (A) LENGTH: 18 amino acids
        (B) TYPE: amino acid
        (C) STRANDEDNESS: single (D) TOPOLOGY: linear (ix) FEATURE:
        (A) NAME/KEY: Modified-site
        (B) LOCATION: 10
        (D) OTHER INFORMATION: /product= "homoarginine(Har)"

(xi) SEQUENCE DESCRIPTION: SEQ ID NO:49:

Arg Gly Gly Lys Val Cys Tyr Gly Arg Xaa Arg Phe Ser Val Cys Val
1               5                  10                  15

Gly Arg (2) INFORMATION FOR SEQ ID NO:50:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(9, 18)
        (D) OTHER INFORMATION: /note= "D form of amino acids"

(xi) SEQUENCE DESCRIPTION: SEQ ID NO:50:

Arg Ala Thr Arg Ile Val Phe Cys Arg Arg Phe Gly Val Cys Val
1               5                  10                  15

Gly Arg (2) INFORMATION FOR SEQ ID NO:51:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 10
        (D) OTHER INFORMATION: /product= "homoarginine(Har)"
            /note= "D form of amino acid"

(xi) SEQUENCE DESCRIPTION: SEQ ID NO:51:

Arg Gly Gly Lys Val Cys Tyr Leu Arg Xaa Arg Phe Leu Val Cys Val
1               5                  10                  15

Gly Arg (2) INFORMATION FOR SEQ ID NO:52:

(i) SEQUENCE CHARACTERISTICS:
        (A) LENGTH: 18 amino acids
        (B) TYPE: amino acid
        (C) STRANDEDNESS: single
        (D) TOPOLOGY: linear (xi) SEQUENCE DESCRIPTION: SEQ ID NO:52:

Arg Gly Gly Arg Ile Cys Phe Leu Arg Pro Arg Ile Gly Val Cys Val
1               5                  10                  15

Gly Arg (2) INFORMATION FOR SEQ ID NO:53:

(i) SEQUENCE CHARACTERISTICS:
        (A) LENGTH: 18 amino acids
        (B) TYPE: amino acid (C) STRANDEDNESS: single
        (D) TOPOLOGY: linear (ix) FEATURE:
        (A) NAME/KEY: Disulfide-bond
        (B) LOCATION: 8..13

(ix) FEATURE:
        (A) NAME/KEY: Modified-site
        (B) LOCATION: group(6, 15)
        (D) OTHER INFORMATION: /note= "X is a hydrophobic, a
            small, or a large polar amino acid"

(xi) SEQUENCE DESCRIPTION: SEQ ID NO:53:

Arg Gly Gly Arg Leu Xaa Tyr Cys Arg Arg Arg Phe Cys Val Xaa Val
1               5                   10                  15

Gly Arg (2) INFORMATION FOR SEQ ID NO:54:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Disulfide-bond
        (B) LOCATION: 8..13

(ix) FEATURE:
        (A) NAME/KEY: Modified-site
        (B) LOCATION: group(6, 15)
        (D) OTHER INFORMATION: /note= "X is a hydrophobic, a
            small, or a large polar amino acid"

(xi) SEQUENCE DESCRIPTION: SEQ ID NO:54:

Arg Gly Gly Arg Leu Xaa Tyr Cys Arg Arg Arg Phe Cys Ile Xaa Val
1               5                   10                  15

Gly Arg (2) INFORMATION FOR SEQ ID NO:55:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Disulfide-bond
        (B) LOCATION: 8..13

(ix) FEATURE:
        (A) NAME/KEY: Modified-site
        (B) LOCATION: group(6, 15)
        (D) OTHER INFORMATION: /note= "X is a hydrophobic, a
            small, or a large polar amino acid"

(xi) SEQUENCE DESCRIPTION: SEQ ID NO:55:

Arg Gly Gly Gly Leu Xaa Tyr Cys Arg Arg Arg Phe Cys Val Xaa Val
1               5                   10                  15

Gly Arg (2) INFORMATION FOR SEQ ID NO:56:

(i) SEQUENCE CHARACTERISTICS:
        (A) LENGTH: 18 amino acids
        (B) TYPE: amino acid
        (C) STRANDEDNESS: single (D) TOPOLOGY: linear (ix) FEATURE:
                (A) NAME/KEY: Disulfide-bond
                (B) LOCATION: 8..13

(ix) FEATURE:
                (A) NAME/KEY: Modified-site
                (B) LOCATION: group(6, 15)
                (D) OTHER INFORMATION: /note= "X is a hydrophobic, a
                    small, or a large polar amino acid"

(xi) SEQUENCE DESCRIPTION: SEQ ID NO:56:

Arg Gly Gly Arg Leu Xaa Tyr Cys Arg Trp Gly Ile Cys Phe Xaa Val
1               5                   10                  15

Gly Arg (2) INFORMATION FOR SEQ ID NO:57:

(i) SEQUENCE CHARACTERISTICS:
            (A) LENGTH: 18 amino acids
            (B) TYPE: amino acid
            (C) STRANDEDNESS: single
            (D) TOPOLOGY: linear (ix) FEATURE:
            (A) NAME/KEY: Disulfide-bond
            (B) LOCATION: 8..13

(ix) FEATURE:
            (A) NAME/KEY: Modified-site
            (B) LOCATION: group(6, 15)
            (D) OTHER INFORMATION: /note= "X is a hydrophobic, a
                small, or a large polar amino acid"

(xi) SEQUENCE DESCRIPTION: SEQ ID NO:57:

Arg Gly Gly Arg Leu Xaa Tyr Cys Arg Pro Arg Phe Cys Val Xaa Val
1               5                   10                  15

Gly Arg (2) INFORMATION FOR SEQ ID NO:58:

(i) SEQUENCE CHARACTERISTICS:
            (A) LENGTH: 18 amino acids
            (B) TYPE: amino acid
            (C) STRANDEDNESS: single
            (D) TOPOLOGY: linear (ix) FEATURE:
            (A) NAME/KEY: Disulfide-bond
            (B) LOCATION: 6..15

(ix) FEATURE:
            (A) NAME/KEY: Modified-site
            (B) LOCATION: group(8, 13)
            (D) OTHER INFORMATION: /note= "X is a hydrophobic, a
                small, or a large polar amino acid"

(xi) SEQUENCE DESCRIPTION: SEQ ID NO:58:

Arg Gly Gly Arg Leu Cys Tyr Xaa Arg Arg Arg Phe Xaa Val Cys Val
1               5                   10                  15

Gly Arg (2) INFORMATION FOR SEQ ID NO:59:

(i) SEQUENCE CHARACTERISTICS:
            (A) LENGTH: 18 amino acids
            (B) TYPE: amino acid
            (C) STRANDEDNESS: single
            (D) TOPOLOGY: linear

```
    (ix) FEATURE:
         (A) NAME/KEY: Disulfide-bond
         (B) LOCATION: 6..15

(ix) FEATURE:
         (A) NAME/KEY: Modified-site
         (B) LOCATION: group(8, 13)
         (D) OTHER INFORMATION: /note= "X is a hydrophobic, a
             small, or a large polar amino acid"

(xi) SEQUENCE DESCRIPTION: SEQ ID NO:59:

Arg Gly Gly Arg Leu Cys Tyr Xaa Arg Arg Arg Phe Xaa Ile Cys Val
1               5                  10                  15

Gly Arg (2) INFORMATION FOR SEQ ID NO:60:

(i) SEQUENCE CHARACTERISTICS:
         (A) LENGTH: 18 amino acids
         (B) TYPE: amino acid
         (C) STRANDEDNESS: single
         (D) TOPOLOGY: linear (ix) FEATURE:
         (A) NAME/KEY: Disulfide-bond
         (B) LOCATION: 6..15

(ix) FEATURE:
         (A) NAME/KEY: Modified-site
         (B) LOCATION: group(8, 13)
         (D) OTHER INFORMATION: /note= "X is a hydrophobic, a
             small, or a large polar amino acid"

(xi) SEQUENCE DESCRIPTION: SEQ ID NO:60:

Arg Gly Gly Gly Leu Cys Tyr Xaa Arg Arg Arg Phe Xaa Val Cys Val
1               5                  10                  15

Gly Arg (2) INFORMATION FOR SEQ ID NO:61:

(i) SEQUENCE CHARACTERISTICS:
         (A) LENGTH: 18 amino acids
         (B) TYPE: amino acid
         (C) STRANDEDNESS: single
         (D) TOPOLOGY: linear (ix) FEATURE:
         (A) NAME/KEY: Disulfide-bond
         (B) LOCATION: 6..15

(ix) FEATURE:
         (A) NAME/KEY: Modified-site
         (B) LOCATION: group(8, 13)
         (D) OTHER INFORMATION: /note= "X is a hydrophobic, a
             small, or a large polar amino acid"

(xi) SEQUENCE DESCRIPTION: SEQ ID NO:61:

Arg Gly Gly Arg Leu Cys Tyr Xaa Arg Trp Gly Ile Xaa Phe Cys Val
1               5                  10                  15

Gly Arg (2) INFORMATION FOR SEQ ID NO:62:

(i) SEQUENCE CHARACTERISTICS:
         (A) LENGTH: 18 amino acids
         (B) TYPE: amino acid
         (C) STRANDEDNESS: single
         (D) TOPOLOGY: linear
```

```
    (ix) FEATURE:
         (A) NAME/KEY: Disulfide-bond
         (B) LOCATION: 6..15

(ix) FEATURE:
         (A) NAME/KEY: Modified-site
         (B) LOCATION: group(8, 13)
         (D) OTHER INFORMATION: /note= "X is a hydrophobic, a
             small, or a large polar amino acid"

(xi) SEQUENCE DESCRIPTION: SEQ ID NO:62:

Arg Gly Gly Arg Leu Cys Tyr Xaa Arg Pro Arg Phe Xaa Val Cys Val
1               5                   10                  15

Gly Arg (2) INFORMATION FOR SEQ ID NO:63:

(i) SEQUENCE CHARACTERISTICS:
         (A) LENGTH: 18 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: group(6, 8, 13, 15)
         (D) OTHER INFORMATION: /note= "X is a hydrophobic, a
             small, or a large polar amino acid"

(xi) SEQUENCE DESCRIPTION: SEQ ID NO:63:

Arg Gly Gly Arg Leu Xaa Tyr Xaa Arg Arg Arg Phe Xaa Val Xaa Val
1               5                   10                  15

Gly Arg (2) INFORMATION FOR SEQ ID NO:64:

(i) SEQUENCE CHARACTERISTICS:
         (A) LENGTH: 16 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: group(6, 8, 13, 15)
         (D) OTHER INFORMATION: /note= "X is a hydrophobic, a
             small, or a large polar amino acid"

(xi) SEQUENCE DESCRIPTION: SEQ ID NO:64:

Arg Gly Gly Arg Leu Xaa Tyr Xaa Arg Arg Arg Phe Xaa Ile Xaa Val
1               5                   10                  15

(2) INFORMATION FOR SEQ ID NO:65:

(i) SEQUENCE CHARACTERISTICS:
         (A) LENGTH: 18 amino acids
         (B) TYPE: amino acid
         (C) STRANDEDNESS: single
         (D) TOPOLOGY: linear (ix) FEATURE:
         (A) NAME/KEY: Modified-site
         (B) LOCATION: group(6, 8, 13, 15)
         (D) OTHER INFORMATION: /note= "X is a hydrophobic, a
             small, or a large polar amino acid"

(xi) SEQUENCE DESCRIPTION: SEQ ID NO:65:

Arg Gly Gly Gly Leu Xaa Tyr Xaa Arg Arg Arg Phe Xaa Val Xaa Val
1               5                   10                  15
```

Gly Arg (2) INFORMATION FOR SEQ ID NO:66:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(5, 7, 13, 15)
        (D) OTHER INFORMATION: /note= "X is a hydrophobic, a
            small, or a large polar amino acid"

(xi) SEQUENCE DESCRIPTION: SEQ ID NO:66:

Arg Gly Gly Arg Xaa Leu Xaa Tyr Arg Gly Trp Ile Xaa Phe Xaa Val
1               5                   10                  15

Gly Arg (2) INFORMATION FOR SEQ ID NO:67:

(i) SEQUENCE CHARACTERISTICS:
        (A) LENGTH: 18 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: group(6, 8, 13, 15)
        (D) OTHER INFORMATION: /note= "X is a hydrophobic, a
            small, or a large polar amino acid"

(xi) SEQUENCE DESCRIPTION: SEQ ID NO:67:

Arg Gly Gly Arg Leu Xaa Tyr Xaa Arg Arg Phe Xaa Val Xaa Val
1               5                   10                  15

Gly Arg (2) INFORMATION FOR SEQ ID NO:68:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:68:

GTCGGAATTC ATGGAGACCC AGAGRGCCAG                                30

(2) INFORMATION FOR SEQ ID NO:69:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:69:

GTCGTCTAGA SGTTTCACAA GAATTTATTT                                30

(2) INFORMATION FOR SEQ ID NO:70:

(i) SEQUENCE CHARACTERISTICS:
        (A) LENGTH: 19 amino acids
        (B) TYPE: amino acid
        (C) STRANDEDNESS: single (D) TOPOLOGY: linear (xi) SEQUENCE DESCRIPTION: SEQ ID NO:70:

Arg Gly Gly Arg Leu Cys Tyr Cys Arg Gly Trp Ile Cys Phe Cys Val
1               5                   10                  15

Gly Arg Gly (2) INFORMATION FOR SEQ ID NO:71:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:71:

AAGGCCGTGA GTCG                                                        14

(2) INFORMATION FOR SEQ ID NO:72:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:72:

AACGGGGTGA GGCT                                                        14

(2) INFORMATION FOR SEQ ID NO:73:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:73:

AATGAGGTGA GTGG                                                        14

(2) INFORMATION FOR SEQ ID NO:74:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:74:

TTGACCAGGA CGAG                                                        14

(2) INFORMATION FOR SEQ ID NO:75:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:75:

CCTTCCAGCG GGTG                                                        14

(2) INFORMATION FOR SEQ ID NO:76:

(i) SEQUENCE CHARACTERISTICS:
        (A) LENGTH: 14 base pairs

```
    (B) TYPE: nucleic acid
    (C) STRANDEDNESS: single
    (D) TOPOLOGY: linear (xi) SEQUENCE DESCRIPTION: SEQ ID NO:76:

GGTCACAGGT TCAA                                                            14
```

COMPOSITIONS AND METHODS FOR TREATING AND PREVENTING MICROBIAL AND VIRAL INFECTIONS

This application is a continuation of application Ser. No. 08/499,523, filed Jul. 7, 1995, and issued as U.S. Pat. No. 5,804,558 on Sep. 8, 1998, which is a continuation-in-part of U.S. Ser. No. 08/451,832, filed May, 26, 1995, and now abandoned, which is a continuation-in-part of U.S. Ser. No. 08/243,879 filed May 17, 1994, and issued as U.S. Pat. No. 5,708,145 on Jan. 13, 1998, which is a continuation-in-part of U.S. Ser. No. 08/182,483 filed Jan. 13, 1994, and issued as U.S. Pat. No. 5,693,486 on Dec. 2, 1997, which is a continuation-in-part of U.S. Ser. No. 08/095,769 filed Jul. 26, 1993, and issued as U.S. Pat. No. 5,464,823 on Nov. 7, 1995, which is a continuation-in-part of U.S. Ser. No. 08/093,926 filed Jul. 20, 1993, and now abandoned. The contents of these applications are incorporated herein by reference.

This invention was made with funding from NIH Grant No. A122839. The U.S. Government has certain rights in this invention.

TECHNICAL FIELD

The invention relates to the field of antibiotic peptides. In particular, the invention concerns short peptides, some of which are isolated from porcine leukocytes, that have a wide range of antimicrobial activities.

BACKGROUND ART

One of the defense mechanisms against infection by both animals and plants is the production of peptides that have antimicrobial and antiviral activity. Various classes of these peptides have been isolated from tissues both of plants and animals. One well known class of such peptides is the tachyplesins which were first isolated from the hemocytes of the horseshoe crab as described by Nakamura, T. et al. *J Biol Chem* (1988) 263:16709–16713. This article described the initial tachyplesin isolated, Tachyplesin I, from the Japanese species. Tachyplesin I is a 17-amino acid amidated peptide containing four cysteine residues providing two intramolecular cystine bonds. A later article by this group, Miyata, T. et al. *J Biochem* (1989) 106:663–668, reports the isolation of a second tachyplesin, Tachyplesin II, consisting of 17 residues amidated at the C-terminus, also containing four cysteine residues and two intramolecular disulfide bonds. Two additional 18-mers, called polyphemusins, highly homologous to Tachyplesin II and containing the same positions for the four cysteine residues, were also isolated from the American horseshoe crab. Polyphemusin I and Polyphemusin II differ from each other only in the replacement of one arginine residue by a lysine. All of the peptides were described as having antifungal and antibacterial activity. A later article by Murakami, T. et al. *Chemotherapy* (1991) 37:327–334, describes the antiviral activity of the tachyplesins with respect to vesicular stomatitis virus; Herpes Simplex Virus I & II, Adenovirus I, Reovirus II and Poliovirus I were resistant to inactivation by Tachyplesin I. Morimoto, M. et al. *Chemotherapy* (1991) 37:206–211, found that Tachyplesin I was inhibitory to Human Immunodeficiency Virus. This anti-HIV activity was found also to be possessed by a synthetic analog of Polyphemusin II as described by Nakashima, H. et al. *Antimicrobial Agents and Chemotherapy* (1992) 1249–1255. Antiviral peptides have also been found in rabbit leukocytes as reported by Lehrer, R. I. et al. *J Virol* (1985) 54:467–472.

Other important classes of cysteine-containing antimicrobial peptides include the defensins, β-defensins and insect defensins. The defensins are somewhat longer peptides characterized by six invariant cysteines and three intramolecular cystine disulfide bonds. Defensins were described by Lehrer, R. I. et al. *Cell* (1991) 64:229–230; Lehrer, R. I. et al. *Ann Rev Immunol* (1993) 11:105–128. A review of mammalian-derived defensins by Lehrer, R. I. et al. is found in *Annual Review Immunol* (1993) 11:105–128; three patents have issued on the defensins: U.S. Pat. No. 4,705,777; U.S. Pat. No. 4,659,692; and U.S. Pat. No. 4,543,252. Defensins have been found in the polymorphonucleated neutrophils (PMN) of humans and of several other animals, as well as in rabbit pulmonary alveolar macrophages, and in murine small intestinal epithelial (Paneth) cells and in corresponding cells in humans.

β-Defensins are found in bovine respiratory epithelial cells, bovine granulocytes and avian leukocytes. See Selsted, M. E. et al. *J Biol Chem* (1993) 288:6641–6648 and Diamond, G. et al. *Proc Natl Acad Sci* (USA) (1991) 88:3952–3958. Insect defensins have been reported by Lambert, J. et al. *Proc Natl Acad Sci* (USA) (1989) 88:262–265.

Antifungal and antibacterial peptides and proteins have also been found in plants (Broekaert, W. F. et al. *Biochemistry* (1992) 31:4308–4314) as reviewed by Cornelissen, B. J. C. et al. *Plant Physiol* (1993) 101:709–712. Expression systems for the production of such peptides have been used to transform plants to protect the plants against such infection as described, for example, by Haln, R. et al. *Nature* (1993) 361:153–156.

The present invention provides a new class of antimicrobial and antiviral peptides, designated "protegrins" herein, representative members of which have been isolated from porcine leukocytes. These peptides are useful as antibacterial antiviral and antifungal agents in both plants and animals.

The isolation of the protegrin peptides of the invention was reported by the present applicants in a paper by Kokryakov, V. N. et al. *FEBS* (1993) 337:231–236 (July issue). A later publication of this group described the presence of a new protegrin, whose sequence, and that of its precursor, was deduced from its isolated cDNA clone. Zhao, C et al, *FEBS Letters* (1994) 346:285–288. An additional paper disclosing cationic peptides from porcine neutrophils was published by Mirgorodskaya, O. A. et al. *FEBS* (1993) 330:339–342 (September issue). Storici, P. et al. *Biochem Biophys Res Comm* (1993) 196:1363–1367, report the recovery of a DNA sequence which encodes a pig leukocyte antimicrobial peptide with a cathelin-like prosequence. The peptide is reported to be one of the protegrins disclosed hereinbelow. Additional publications related to protegrins are Harwig, S. S. L., et al. *J. Peptide Sci*. (1995) in press; and Zhao, C., et al. FEBS-MS MB-283 (1995) in press.

The protegrins of the invention have also been found to bind to endotoxins—i.e., the lipopolysaccharide (LPS) compositions derived from gram-negative bacteria which are believed responsible for gram-negative sepsis. This type of sepsis is an extremely common condition and is often fatal. Others have attempted to design and study proteins which bind LPS/endotoxin, and illustrative reports of these attempts appear in Rustici, A. et al. *Science* (1993) 259:361–364; Matsuzaki, K. et al. *Biochemistry* (1993) 32:11704–11710; Hoess, A. et al. *EMBO J* (1993) 12:3351–3356; and Elsbach, P. et al. *Current Opinion in Immunology* (1993) 5:103–107. The protegrins of the present invention provide additional compounds which are capable of inactivating of LPS and ameliorating its effects.

In addition to the foregoing, the protegrins of the invention are effective in inhibiting the growth of organisms that are associated with sexually transmitted diseases. It is estimated that 14 million people world-wide are infected with HIV and that millions of women sustain pelvic inflammatory disease each year. Chlamydia trachomatis and Neisseria gonorrhoeae cause over half of this inflammatory disease although E. coli, Mycoplasma hominis and other infectious microorganisms can also be responsible. Pathogens include viral, bacterial, fungal and protozoan pathogens. It is especially important that the antibiotics used to combat these infections be effective under physiological conditions. The protegrins of the present invention offer these properties.

Disclosure of the Invention

In one embodiment, the invention is directed to peptides of 16–18 amino acid residues characterized by four invariant cysteines and either by a characteristic pattern of basic and hydrophobic amino acids and/or being isolatable from animal leukocytes using the method of the invention. In a second embodiment, the invention is directed to the above peptides wherein 1–4 of these cysteines is replaced by a hydrophobic or small amino acid. All of these peptides can be produced synthetically and some can be produced recombinantly or can be isolated from their native sources and purified for use as preservatives or in pharmaceutical compositions in treating or preventing infection in animals. Alternatively, the peptides can be formulated into compositions which can be applied to plants to protect them against viral or microbial infection. In still another approach, the DNA encoding the peptides can be expressed in situ, in animals or preferably in plants, to combat infections. The peptides are also useful as standards in antimicrobial assays and in binding endotoxins.

Accordingly, in one aspect, the invention is directed to a purified and isolated or recombinantly produced compound of the formula

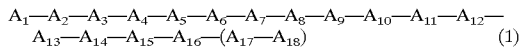

$$A_1-A_2-A_3-A_4-A_5-A_6-A_7-A_8-A_9-A_{10}-A_{11}-A_{12}-A_{13}-A_{14}-A_{15}-A_{16}-(A_{17}-A_{18}) \quad (1)$$

and the N-terminal acylated and/or C-terminal amidated or esterified forms thereof, which is either in the optionally -SH stabilized linear or in a cystine-bridged form wherein each of $A_1$ and $A_9$ is independently a basic amino acid;

each of $A_2$ and $A_3$ is independently a small amino acid;

each of $A_5$, $A_7$, $A_{12}$, $A_{14}$ and $A_{16}$ is independently a hydrophobic amino acid;

$A_4$ is a basic or a small amino acid;

$A_{10}$ is a basic or a small amino acid or is proline;

$A_{11}$ is a basic or a hydrophobic amino acid;

$A_{17}$ is not present or, if present, is a small amino acid;

$A_{18}$ is not present or, if present, is a basic amino acid, or a modified form of formula (1) and the N-terminal acylated and/or C-terminal amidated or esterified forms thereof wherein at least one of the 4 cysteines is independently replaced by a hydrophobic amino acid or a small amino acid.

In still other aspects, the invention is directed to recombinant materials useful for the production of the peptides of the invention as well as plants or animals modified to contain expression systems for the production of these peptides. The invention is also directed to pharmaceutical compositions and compositions for application to plants containing the peptides of the invention as active ingredients or compositions which contain expression systems for production of the peptides or for in situ expression of the nucleotide sequence encoding these peptides. The invention is also directed to methods to prepare the invention peptides synthetically, to antibodies specific for these peptides, and to the use of the peptides as preservatives.

In other aspects, the invention is directed to the use of the compounds of the invention as standards in antimicrobial assays. The compounds may also be used as antimicrobials in solutions useful in eye care, such as contact lens solutions, and in topical or other pharmaceutical compositions for treatment of sexually transmitted diseases (STDs). The invention is also directed to use of the invention compounds as preservatives for foods or other perishables. As the invention peptides can inactivate endotoxin, the invention is also directed to a method to inactivate endotoxins using the compounds of the invention and to treat gram-negative sepsis by taking advantage of this property.

BRIEF DESCRIPTION OF THE DRAWINGS

FIG. 4 shows the antimicrobial activity of the purified porcine protegrins of the invention:

FIG. 5 shows the effect of various test conditions on antimicrobial activity:

FIG. 5a shows activity against Candida albicans in 100 μM NaCl;

FIG. 5b shows activity against E. Coli in 100 μM NaCl;

FIG. 5c shows activity against Candida albicans in 90% fetal calf serum.

FIG. 6 shows the antimicrobial activity of the linear forms of the protegrins under various test conditions:

FIG. 7 shows a composite of cDNA encoding the precursors of PG-1(SEQ ID NOS: 1 and 2), PG-2(SEQ ID NOS: 3 and 4), PG-3 (SEQ ID NOS: 5 and 6) and PG-4(SEQ ID NOS: 7 and 8).

FIG. 8 shows the nucleotide sequence (SEQ ID NOS: 9) and the deduced amino acid sequence (SEQ ID NOS: 10) of the genomic DNA encoding the precursor protein for the antimicrobial compounds of the invention PG-1, PG-3, and PG-5.

FIGS. 11a–11c show the antimicrobial activity of synthetically prepared PG-5 as compared to that of synthetically prepared PG-1.

FIG. 13 shows a graphical representation of the effects of the kite and bullet forms of PG-1 against gram positive bacteria.

FIG. 16 is a graphical representation of the antimicrobial activity of the snake form of PG-1 against gram negative bacteria.

MODES OF CARRYING OUT THE INVENTION

Figure 1:
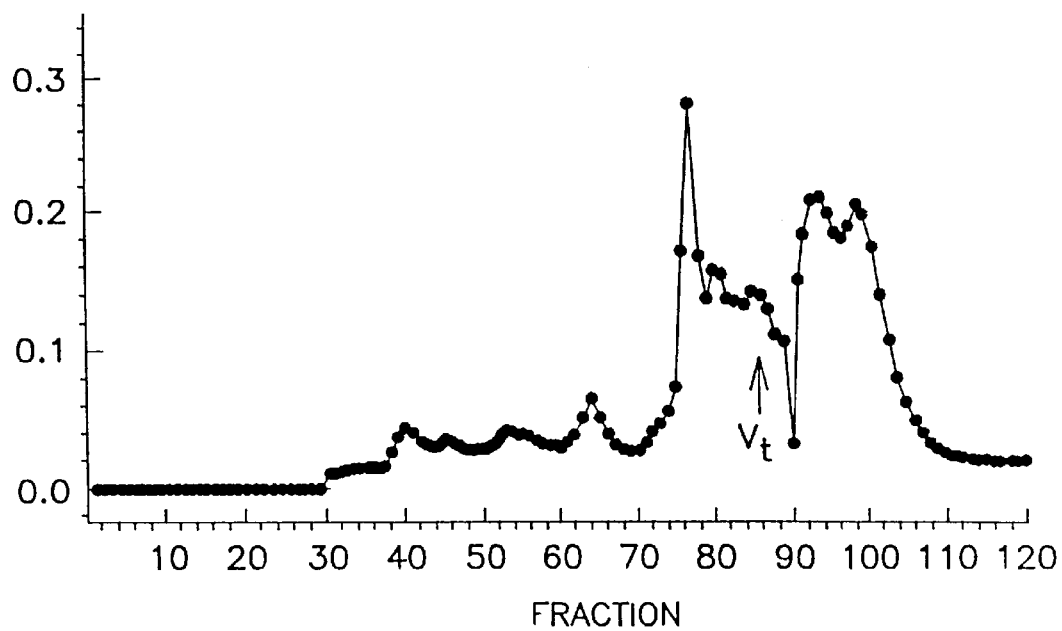
FIG. 1 shows the elution pattern of a concentrate of the ultrafiltrate of porcine leukocytes applied to a Biogel P10 column.

The peptides of the invention are described by the formula:

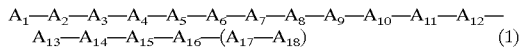

$$A_1—A_2—A_3—A_4—A_5—A_6—A_7—A_8—A_9—A_{10}—A_{11}—A_{12}—A_{13}—A_{14}—A_{15}—A_{16}—(A_{17}—A_{18}) \quad (1)$$

and its defined modified forms. Those peptides which occur in nature must be in purified and isolated form or prepared recombinantly.

The designation $A_n$ in each case represents an amino acid at the specified position in the peptide. As $A_{17}$ and $A_{18}$ may or may not be present, the peptides of the invention contain either 16, 17 or 18 amino acids. The positions of the cysteine residues, shown as C in Formula (1), are invariant in the peptides of the invention; however, in the modified forms of the peptides of Formula (1), also included within the scope of the invention, at least one of 1–4 of these cysteines may be replaced by a hydrophobic or small amino acid.

The amino terminus of the peptide may be in the free amino form or may be acylated by a group of the formula RCO—, wherein R represents a hydrocarbyl group of 1–6C. The hydrocarbyl group is saturated or unsaturated and is typically, for example, methyl, ethyl, i-propyl, t-butyl, n-pentyl, cyclohexyl, cyclohexene-2-yl, hexene-3-yl, hexyne-4-yl, and the like.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6C as defined above. Amidated forms of the peptides wherein the C-terminus has the formula $CONH_2$ are preferred.

As the peptides of the invention contain substantial numbers of basic amino acids, the peptides of the invention may be supplied in the form of the acid addition salts. Typical acid addition salts include those of inorganic ions such as chloride, bromide, iodide, fluoride or the like, sulfate, nitrate, or phosphate, or may be salts of organic anions such as acetate, formate, benzoate and the like. The acceptability of each of such salts is dependent on the intended use, as is commonly understood.

The peptides of the invention that contain at least two cysteines may be in straight-chain or cyclic form. The straight-chain forms are convertible to the cyclic forms, and vice versa. Methods for forming disulfide bonds to create the cyclic peptides are well known in the art, as are methods to reduce disulfides to form the linear compounds. The linear compounds can be stabilized by addition of a suitable alkylating agent such as iodoacetamide.

The cyclic forms are the result of the formation of cystine linkages among all or some of the four invariant cysteine residues. Cyclic forms of the invention include all possible permutations of cystine bond formation; if the cysteines are numbered in order of their occurrence starting at the N-terminus as $C_6$, $C_8$, $C_{13}$ and $C_{15}$, these permutations include:

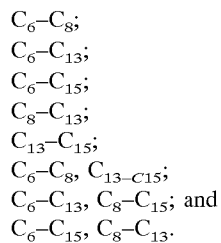

$C_6–C_8$;
$C_6–C_{13}$;
$C_6–C_{15}$;
$C_8–C_{13}$;
$C_{13}–C_{15}$;
$C_6–C_8$, $C_{13–C15}$;
$C_6–C_{13}$, $C_8–C_{15}$; and
$C_6–C_{15}$, $C_8–C_{13}$.

In the modified forms of the peptides, where 1–4 cysteines are replaced, similar permutations are available when 2–3 cysteines are present.

The native forms of the protegrins contain two cystine bonds: one between the cysteine at position 6 and the cysteine at position 15 and the other between the cysteine at position 8 and the cysteine at position 13. Accordingly, in those embodiments having two cystine linkages, the $C_6–C_{15}$, $C_8–C_{13}$ form is preferred. However, it has been found by the present applicants that forms of the protegrins containing only one cystine linkage are active and easily prepared. Preferred among embodiments having only one cystine linkage are those represented by $C_6–C_{15}$ alone and by $C_8–C_{13}$ alone.

Forms containing a $C_6–C_{15}$ cystine as the only cystine linkage are generally designated "bullet" forms of the protegrins; those wherein the sole cystine is $C_8–C_{13}$ are designated the "kite" forms. The bullet and kite forms can most conveniently be made by replacing the cystines at the positions not to be linked by cystine with a neutral amino acid, preferably a small amino acid such as glycine, serine, alanine or threonine and less preferably a neutral polar amino acid such as asparagine or glutamine or by a hydrophobic amino acid. Thus, in some embodiments of the bullet form, each of $C_8$ and $C_{13}$ is independently alanine, serine, threonine or glycine, preferably both are alanine. Conversely, in the kite form $C_6$ and $C_{15}$ are thus replaced.

As the linearalized forms of the native cyclic peptides have valuable activities, even when chemically stabilized to preserve the sulfhydryl form of cysteine for example, by reaction with iodoacetamide, the compounds of the invention also include linearalized forms which are stabilized with suitable reagents. As defined herein, "SH-stabilized" forms of the peptides of the invention contain sulfhydryl groups reacted with standard reagents to prevent reformation into disulfide linkages.

An alternative approach to providing linear forms of the protegrins of the invention comprises use of the modified form of the peptides where cysteine residues are replaced by amino acids which do not form cystine linkages. In this instance, too, all 4 (or at least 3) of the cystines at positions 6, 8, 13, and 15 are replaced by polar neutral or small amino acids as listed above. It is preferred that all 4 cysteine residues be replaced in order to minimize the likelihood of intermolecular bonding.

The amino acids denoted by $A_n$ may be those encoded by the gene or analogs thereof, and may also be the D-isomers thereof. One preferred embodiment of the peptides of the invention is that form wherein all of the residues are in the D-configuration thus conferring resistance to protease activity while retaining antimicrobial or antiviral properties. The resulting protegrins are themselves enantiomers of the native L-amino acid-containing forms.

The amino acid notations used herein are conventional and are as follows:

| Amino Acid | One-Letter Symbol | Three-Letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Hydrophobic: The residues are not charged at physiological pH and the residue is repelled by aqueous solution so as to seek the inner positions in the conformation of a peptide in which it is contained when the peptide is in aqueous medium.

Neutral/polar: The residues are not charged at physiological pH, but the residue is not sufficiently repelled by aqueous solutions so that it would seek inner positions in the conformation of a peptide in which it is contained when the peptide is in aqueous medium.

This description also characterizes certain amino acids as "small" since their side chains are not sufficiently large, even if polar groups are lacking, to confer hydrophobicity. "Small" amino acids are those with four carbons or less when at least one polar group is on the side chain and three carbons or less when not.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always nonaromatic.

For the naturally occurring protein amino acids, subclassification according to the foregoing scheme is as follows.

Acidic: Aspartic acid and Glutamic acid;

Basic: Noncyclic: Arginine, Lysine; Cyclic: Histidine;

Small: Glycine, Serine, Alanine, Threonine;

Polar/large: Asparagine, Glutamine;

Hydrophobic: Tyrosine, Valine, Isoleucine, Leucine, Methionine, Phenylalanine, Tryptophan.

The gene-encoded secondary amino acid proline is a special case due to its known effects on the secondary conformation of peptide chains, and is not, therefore, included in a group. Cysteine residues are also not included in these classifications since their capacity to form disulfide bonds to provide secondary structure is critical in the compounds of the present invention.

Certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har). These also fall conveniently into particular categories.

Based on the above definitions,

Sar, beta-Ala, 2,3-diaP and Aib are small;

t-BuA, t-BuG, N-MeIle, Nle, Mvl, Cha, Phg, Nal, Thi and Tic are hydrophobic;

Orn and Har are basic;

Cit, Acetyl Lys, and MSO are neutral/polar.

The various omega-amino acids are classified according to size as small (beta-Ala and 3-aminopropionic) or as large and hydrophobic (all others).

Other amino acid substitutions of those encoded in the gene can also be included in peptide compounds within the scope of the invention and can be classified within this general scheme according to their structure.

In all of the peptides of the invention, one or more amide linkages (—CO—NH—) may optionally be replaced with another linkage which is an isostere such as —CH$_2$NH—, —CH$_2$S—, —CH$_2$CH$_2$, —CH=CH— (cis and trans), —COCH$_2$—, —CH(OH)CH$_2$— and —CH$_2$SO—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Hann, M. M., *J Chem Soc Perkin Trans I* (1982) 307–314 (—CH—CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—)

The compounds of Formula (1) are generally defined as

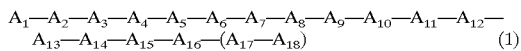
$$A_{13}-A_{14}-A_{15}-A_{16}-(A_{17}-A_{18}) \tag{1}$$

and the N-terminal acylated and/or C-terminal amidated or esterified forms thereof, which is either in the optionally -SH stabilized linear or in a cystine-bridged form wherein each of A$_1$ and A$_9$ is independently a basic amino acid;

each of A$_2$ and A$_3$ is independently a small amino acid;

each of A$_5$, A$_7$, A$_{12}$, A$_{14}$ and A$_{16}$ is independently a hydrophobic amino acid;

A$_4$ is a basic or a small amino acid;

A$_{10}$ is a basic or a small amino acid or is proline;

A$_{11}$ is a basic or a hydrophobic amino acid;

A$_{17}$ is not present or, if present, is a small amino acid;

A$_{18}$ is not present or, if present, is a basic amino acid, or a modified form of formula (1) and the N-terminal acylated and/or C-terminal amidated or esterified forms thereof wherein at least one of the 4 and up to all 4 cysteines is each independently replaced by a hydrophobic amino acid or a small amino acid.

In preferred embodiments of the compounds of the invention, each of A$_1$ and A$_9$ is independently selected from the group consisting of R, K and Har; more preferably, both A$_1$ and A$_9$ are R.

In another class of preferred embodiments, each of A$_2$ and A$_3$ is independently selected from the group consisting of G, A, S and T; more preferably, A$_2$ and A$_3$ are G.

In another set of preferred embodiments, A$_4$ is selected from the group consisting of R, K, Har, G, A, S and T; more preferably, A$_4$ is R or G.

In another set of preferred embodiments, each of A$_5$, A$_{14}$ and A$_{16}$ is selected independently from the group consisting of I, V, L, Nle and F; preferably I, V, L and F.

In another set of preferred embodiments, each of A$_7$ and A$_{12}$ is independently selected from the group consisting of I, V, L, W, Y and F; preferably A$_7$ is Y and A$_{12}$ is I or F.

In another set of preferred embodiments, A$_{10}$ is R, G or P.

In another set of preferred embodiments, A$_{11}$ is R or W.

A$_{17}$, when present, is preferably G, A, S or T, most preferably G;

A$_{18}$, when present, is preferably R, K or Har, most preferably R.

As described above, the compounds of Formula (1) are either in cyclic or noncyclic (linearalized) form or may be modified wherein 1–4 of the cysteines is replaced by a small amino acid residue or a hydrophobic residue or a polar large amino acid residue. If the linearalized forms of the compound of Formula (1) are prepared, or if linearalized forms of those modified peptides which contain at least two cysteines are prepared, it is preferred that the sulfhydryl groups be stabilized by addition of a suitable reagent. Preferred embodiments for the hydrophobic amino acid to replace cysteine residues are I, V, L and NLe, preferably I, V or L. Preferred small amino acids to replace the cysteine residues include G, A, S and T, most preferably G. Preferred large polar amino acids are N and Q.

In an alternative embodiment, the peptides of the invention are defined as described by Formula (1), but wherein the definitions of A$_n$ in each case are determined by the isolatability of the peptide from animal leukocytes by the invention method. The invention method comprises the steps of providing an ultrafiltrate of a lysate of animal leukocytes and isolating peptides of 16–18 amino acids. These peptides can further be defined by the ability of DNA encoding them to hybridize under stringent conditions to DNA encoding the peptides exemplified as PG-1, PG-2, PG-3, PG-4 and PG-5 herein.

Particularly preferred compounds of the invention are:
Unmodified Forms
PG-1: R-G-G-R-L-C-Y-C-R-R-R-F-C-V-C-V-G-R (SEQ ID NO: 16)
PG-2: R-G-G-R-L-C-Y-C-R-R-R-F-C-I-C-V (SEQ ID NO: 17)
PG-3: R-G-G-L-C-Y-C-R-R-R-F-C-V-C-V-G-R (SEQ ID NO: 18)
PG-4: R-G-G-R-L-C-Y-C-R-G-W-I-C-F-C-V-G-R (SEQ ID NO: 19)
PG-5: R-G-G-R-L-C-Y-C-R-P-R-F-C-V-C-V-G-R (SEQ ID NO: 20)
R-G-G-R-L-C-Y-C-R-R-R-F-C-V-C-V (SEQ ID NO: 21)
K-G-G-R-L-C-Y-C-R-R-R-F-C-V-C-V (SEQ ID NO: 22)
R-G-G-Har-L-C-Y-C-R-R-R-F-C-V-C-V (SEQ ID NO: 23)
R-G-G-Har-L-C-Y-C-Har-R-R-F-C-V-C-V-G-R (SEQ ID NO: 24)
R-G-G-R-V-C-Y-C-R-Har-R-F-C-V-C-V-G-R (SEQ ID NO: 25)
R-G-G-R-L-C-Y-C-R-K-K-W-C-V-C-V-G-R (SEQ ID NO: 26)
R-G-G-R-L-C-Y-C-R-Har-R-Y-C-V-C-V-G-R (SEQ ID NO: 27)
R-G-S-G-L-C-Y-C-R-R-K-W-C-V-C-V-G-R (SEQ ID NO: 28)

R-A-T-R-I-C-F-C-R-R-R-F-C-V-C-V-G-R (SEQ ID NO: 29)

R-G-G-K-V-C-Y-C-R-Har-R-F-C-V-C-V-G-R (SEQ ID NO: 30)

R-A-T-R-I-C-F-C-R†-R-R-F-C-V-C-V-G-Rt (SEQ ID NO: 31)

R-G-G-K-V-C-Y-C-R-Har†-R-F-C-V-C-V-G-R (SEQ ID NO: 32)

PG-1: R-G-G-R-L-C-Y-C-R-R-R-F-C-V-C-V-G-R (all †) (SEQ ID NO: 33)

PG-2: R-G-G-R-L-C-Y-C-R-R-R-F-C-I-C-V (all †) (SEQ ID NO: 34)

PG-3: R-G-G-G-L-C-Y-C-R-R-R-F-C-V-C-V-G-R (all †) (SEQ ID NO: 35)

PG-4: R-G-G-R-L-C-Y-C-R-G-W-I-C-F-C-V-G-R (all †) (SEQ ID NO: 36)

PG-5: R-G-G-R-L-C-Y-C-R-P-R-F-C-V-C-V-G-R (SEQ ID NO: 20)

both the linear and mono- and bicyclic forms thereof, and including the N-terminal acylated and C-terminal amidated forms;

Modified Forms

R-G-G-R-L-V-Y-C-R-R-R-F-C-V-C-V-G-R (SEQ ID NO: 37)

R-G-G-R-L-G-Y-C-R-R-R-F-C-I-C-V (SEQ ID NO: 38)

R-G-G-G-L-C-Y-G-R-R-R-F-C-V-C-V-G-R (SEQ ID NO: 39)

R-G-G-R-L-G-Y-G-R-R-R-F-G-V-C-V (SEQ ID NO: 40)

K-G-G-R-L-V-Y-V-R-R-R-F-I-V-C-V (SEQ ID NO: 41)

R-G-G-Har-L-C-Y-C-R-R-R-F-C-V-G-V (SEQ ID NO: 42)

R-G-G-Har-L-C-Y-C-Har-R-R-F-C-V-L-V-G-R (SEQ ID NO: 43)

R-G-G-R-V-C-Y-V-R-Har-R-F-L-V-G-V-G-R (SEQ ID NO: 44)

R-G-G-R-L-C-Y-S-R-K-K-W-C-V-S-V-G-R (SEQ ID NO: 45)

R-G-G-R-L-C-Y-C-R-Har-R-Y-S-V-V-V-G-R (SEQ ID NO: 46)

R-G-S-G-L-S-Y-C-R-R-K-W-G-V-C-V-G-R (SEQ ID NO: 47)

R-A-T-R-I-S-F-S-R-R-R-F-S-V-S-V-G-R (SEQ ID NO: 48)

R-G-G-K-V-C-Y-G-R-Har-R-F-S-V-C-V-G-R (SEQ ID NO: 49)

R-A-T-R-I-V-F-C-R†-R-R-F-G-V-C-V-G-R† (SEQ ID NO: 50)

R-G-G-K-V-C-Y-L-R-Har†-R-F-L-V-C-V-G-R (SEQ ID NO: 51)

R-G-G-R-I-C-F-L-R-P-R-I-G-V-C-V-G-R (SEQ ID NO: 52)

both the linear and cyclic (where possible) forms thereof, and including the N-terminal acylated and C-terminal amidated forms.

Particularly preferred are compounds wherein a single cystine bond is formed between C6 and C15 or between C8 and C13 wherein four compounds having a cystine bond between C8 and C13 each of C6 and C15 is independently replaced by "X" wherein X is a hydrophobic, a small, or a large polar amino acid. Similarly, where the single cystine bond is between C8 and C13, each of C6 and C15 is independently replaced by X as defined above. Also preferred are the "snake" forms of the compounds of the invention where all 4 cysteines are replaced by X as defined above. Particularly preferred embodiments of these compounds of the invention include:

(SEQ ID NO:53)

Kite form-1

```
R-G-G-R-L-X-Y-C-R
                  \
                   R
                   |
                   R
                  /
R-G-V-X-V-C-F
```

(SEQ ID NO:54)

Kite form-2

```
R-G-G-R-L-X-Y-C-R
                  \
                   R
                   |
                   R
                  /
R-G-V-X-I-C-F
```

(SEQ ID NO:55)

Kite form-3

```
R-G-G-G-L-X-Y-C-R
                  \
                   R
                   |
                   R
                  /
R-G-V-X-V-C-F
```

(SEQ ID NO:56)

Kite form-4

```
R-G-G-R-L-X-Y-C-R
                  \
                   W
                   |
                   G
                  /
R-G-V-X-F-C-I
```

(SEQ ID NO:57)

Kite form-5

```
R-G-G-R-L-X-Y-C-R
                  \
                   P
                   |
                   R
                  /
R-G-V-X-V-C-F
```

(SEQ ID NO:58)

Bullet form-1

```
R-G-G-R-L-C-Y-X-R
                  \
                   R
                   |
                   R
                  /
R-G-V-C-V-X-F
```

(SEQ ID NO:59)

Bullet form-2

```
R-G-G-R-L-C-Y-X-R
                  \
                   R
                   |
                   R
                  /
R-G-V-C-I-X-F
```

(SEQ ID NO:60)

Bullet form-3

```
R-G-G-G-L-C-Y-X-R
                  \
                   R
                   |
                   R
                  /
R-G-V-C-V-X-F
```

(SEQ ID NO:61)

Bullet form-4

```
R-G-G-R-L-C-Y-X-R
                  \
                   W
                   |
                   G
                  /
R-G-V-C-F-X-I
```

-continued

Bullet form-5 (SEQ ID NO:62)

```
R-G-G-R-L-C-Y-X-R
              \
               P
               R
              /
R-G-V-C-V-X-F
```

Snake form-1  R-G-G-R-L-X-Y-X-R-R-R-F-X-V-X-V-G-R (SEQ ID NO: 63)

Snake form-2  R-G-G-R-L-X-Y-X-R-R-R-F-X-I-X-V (SEQ ID NO: 64)

Snake form-3  R-G-G-G-L-X-Y-X-R-R-R-F-X-V-X-V-G-R (SEQ ID NO: 65)

Snake form-4  R-G-G-R-X-L-X-Y-R-G-W-I-X-F-X-V-G-R (SEQ ID NO: 66)

Snake form-5  R-G-G-R-L-X-Y-X-R-R-R-F-X-V-X-V-G-R (SEQ ID NO: 67)

wherein X is as defined above.

Particularly preferred embodiments of X are those wherein X is a small amino acid, especially S and A, especially A.

Preparation of the Invention Compounds

The invention compounds, often designated herein "protegrins" are essentially peptide backbones which may be modified at the N- or C-terminus and also may contain one or two cystine disulfide linkages. The peptides may first be synthesized in noncyclized form. These peptides may then be converted to the cyclic peptides if desired by standard methods of cystine bond formation. As applied to the protegrins herein, "cyclic forms" refers to those forms which contain cyclic portions by virtue of the formation of disulfide linkages between cysteine residues in the peptide. If the straight-chain forms are preferred, it is preferable to stabilize the sulfhydryl groups for any peptides of the invention which contain two or more cysteine residues.

Standard methods of synthesis of peptides the size of protegrins are known. Most commonly used currently are solid phase synthesis techniques; indeed, automated equipment for systematically constructing peptide chains can be purchased. Solution phase synthesis can also be used but is considerably less convenient. When synthesized using these standard techniques, amino acids not encoded by the gene and D-enantiomers can be employed in the synthesis. Thus, one very practical way to obtain the compounds of the invention is to employ these standard chemical synthesis techniques.

In addition to providing the peptide backbone, the N- and/or C-terminus can be derivatized, again using conventional chemical techniques. The compounds of the invention may optionally contain an acyl group, preferably an acetyl group at the amino terminus. Methods for acetylating or, more generally, acylating, the free amino group at the N-terminus are generally known in the art; in addition, the N-terminal amino acid may be supplied in the synthesis in acylated form.

At the carboxy terminus, the carboxyl group may, of course, be present in the form of a salt; in the case of pharmaceutical compositions this will be a pharmaceutically acceptable salt. Suitable salts include those formed with inorganic ions such as $NH_4^+$, $Na^+$, $K^+$, $Mg^{++}$, $Ca^{++}$, and the like as well as salts formed with organic cations such as those of caffeine and other highly substituted amines. The carboxy terminus may also be esterified using alcohols of the formula ROH wherein R is hydrocarbyl (1–6C) as defined above. Similarly, the carboxy terminus may be amidated so as to have the formula —$CONH_2$, —CONHR, or —$CONR_2$, wherein each R is independently hydrocarbyl (1–6C) as herein defined. Techniques for esterification and amidation as well as neutralizing in the presence of base to form salts are all standard organic chemical techniques.

If the peptides of the invention are prepared under physiological conditions, the side-chain amino groups of the basic amino acids will be in the form of the relevant acid addition salts.

Formation of disulfide linkages, if desired, is conducted in the presence of mild oxidizing agents. Chemical oxidizing agents may be used, or the compounds may simply be exposed to the oxygen of the air to effect these linkages. Various methods are known in the art. Processes useful for disulfide bond formation have been described by Tam, J. P. et al., *Synthesis* (1979) 955–957; Stewart, J. M. et al, "Solid Phase Peptide Synthesis" 2d Ed. Pierce Chemical Company Rockford, Ill. (1984); Ahmed A. K. et al., *J Biol Chem* (1975) 250:8477–8482 and Pennington M. W. et al., *Peptides* 1990, E. Giralt et al., ESCOM Leiden, The Netherlands (1991) 164–166. An additional alternative is described by Kamber, B. et al., *Helv Chim Acta* (1980) 63:899–915. A method conducted on solid supports is described by Albericio *Int J Pept Protein Res* (1985) 26:92–97.

A particularly preferred method is solution oxidation using molecular oxygen. This method has been used by the inventors herein to refold synthetic PG-1, PG-3 in its amide or acid forms, enantioPG-1 and the two unisulfide PG-1 compounds ($C_6$–$C_{15}$ and $C_8$–$C_{13}$). Recoveries are as high as 30%.

If the peptide backbone is comprised entirely of gene-encoded amino acids, or if some portion of it is so composed, the peptide or the relevant portion may also be synthesized using recombinant DNA techniques. The DNA encoding the peptides of the invention may itself be synthesized using commercially available equipment; codon choice can be integrated into the synthesis depending on the nature of the host. Alternatively, although less convenient, the DNA can be obtained, at least initially, by screening a cDNA library prepared from porcine leukocytes using probes or PCR primers based on the sequences of the protegrins described herein. This results in recovery of the naturally occurring sequence encoding the protegrins of the invention. Obtention of this native sequence is significant for purposes other than the synthesis of the protegrins per se; the availability of the naturally occurring sequences provides a useful probe to obtain corresponding DNA encoding protegrins of other species. Thus, cDNA libraries, for example, of leukocytes derived from other animals can be screened using the native DNA, preferably under conditions of high stringency. High stringency is as defined by Maniatis, et al. *Molecular Cloning: a Laboratory Manual* 2nd Ed, Cold Spring Harbor Laboratory Press (1989), the relevant portions of which are incorporated herein by reference. This procedure also permits recovery of allelic variants of these peptides from the same species.

Alternatively, the protegrins can be prepared by isolation from leukocytes of a desired species using techniques similar to those disclosed herein for the isolation of porcine protegrins. In general, these techniques involve preparing a lysate of a leukocyte preparation, ultrafiltering the supernatant of the clarified lysate and recovering the ultrafiltrate. The ultrafiltrate is then subjected to chromatographic separation. The location of fragments having antimicrobial and antiviral activity corresponding to protegrins can be assessed using criteria of molecular weight and assaying the fractions for the desired activities as described herein. The native forms of these peptides are believed to be the cyclic forms; if desired, the linearalized forms can be prepared by treating the peptides with reducing agents and stabilizing the sulfhydryl groups that result.

Isolated and recombinantly produced forms of the protegrins may require subsequent derivatization to modify the N- and/or C-terminus and, depending on the isolation procedure, to effect the formation of cystine bonds as described hereinabove. Depending on the host organism used for recombinant production and the animal source from which the protein is isolated, some or all of these conversions may already have been effected.

For recombinant production, the DNA encoding the protegrins of the invention is included in an expression system which places these coding sequences under control of a suitable promoter and other control sequences compatible with an intended host cell. Types of host cells available span almost the entire range of the plant and animal kingdoms. Thus, the protegrins of the invention could be produced in bacteria or yeast (to the extent that they can be produced in a nontoxic or refractile form or utilize resistant strains) as well as in animal cells, insect cells and plant cells. Indeed, modified plant cells can be used to regenerate plants containing the relevant expression systems so that the resulting transgenic plant is capable of self protection vis-à-vis these infective agents.

The protegrins of the invention can be produced in a form that will result in their secretion from the host cell by fusing to the DNA encoding the protegrin, a DNA encoding a suitable signal peptide, or may be produced intracellularly. They may also be produced as fusion proteins with additional amino acid sequence which may or may not need to be subsequently removed prior to the use of these compounds as antimicrobials or antivirals.

Thus, the protegrins of the invention can be produced in a variety of modalities including chemical synthesis, recombinant production, isolation from natural sources, or some combination of these techniques.

Those members of the protegrin class which occur naturally are supplied in purified and isolated form. By "purified and isolated" is meant free from the environment in which the peptide normally occurs (in the case of such naturally occurring peptides) and in a form where it can be used practically. Thus, "purified and isolated" form means that the peptide is substantially pure, i.e., more than 90% pure, preferably more than 95% pure and more preferably more than 99% pure or is in a completely different context such as that of a pharmaceutical preparation.

Antibodies

Antibodies to the protegrins of the invention may also be produced using standard immunological techniques for production of polyclonal antisera and, if desired, immortalizing the antibody-producing cells of the immunized host for sources of monoclonal antibody production. Techniques for producing antibodies to any substance of interest are well known. It may be necessary to enhance the immunogenicity of the substance, particularly as here, where the material is only a short peptide, by coupling the hapten to a carrier. Suitable carriers for this purpose include substances which do not themselves produce an immune response in the mammal to be administered the hapten-carrier conjugate. Common carriers used include keyhole limpet hemocyanin (KLH), diphtheria toxoid, serum albumin, and the viral coat protein of rotavirus, VP6. Coupling of the hapten to the carrier is effected by standard techniques such as contacting the carrier with the peptide in the presence of a dehydrating agent such as dicyclohexylcarbodiimide or through the use of linkers such as those available through Pierce Chemical Company, Chicago, Ill.

The protegrins of the invention in immunogenic form are then injected into a suitable mammalian host and antibody titers in the serum are monitored. It should be noted, however, that some forms of the protegrins require modification before they are able to raise antibodies, due to their resistance to antigen processing. For example, the native form of PG-1, containing two cystine bridges is nonimmunogenic when administered without coupling to a larger carrier and was a poor immunogen even in the presence of potent adjuvants and when coupled through glutaraldehyde or to KLH. Applicants believe this to be due to its resistance to attack by leukocyte serine proteases (human PMN elastase and cathepsin G) as well as to attack by an aspartic protease (pepsin) that resembles several macrophage cathepsins. The lack of immunogenicity may therefore result from resistance to processing to a linear form that can fit in the antigen-presenting pocket of the presenting cell. Immunogenecity of these forms of the protegrins can be enhanced by cleaving the disulfide bonds.

Polyclonal antisera may be harvested when titers are sufficiently high. Alternatively, antibody-producing cells of the host such as spleen cells or peripheral blood lymphocytes may be harvested and immortalized. The immortalized cells are then cloned as individual colonies and screened for the production of the desired monoclonal antibodies.

The antibodies of the invention are, of course, useful in immunoassays for determining the amount or presence of the protegrins. Such assays are essential in quality controlled production of compositions containing the protegrins of the invention. In addition, the antibodies can be used to assess the efficacy of recombinant production of the protegrins, as well as screening expression libraries for the presence of protegrin encoding genes.

Compositions Containing the Protegrins and Methods of Use

The protegrins of the invention are effective in inactivating a wide range of microbial and viral targets, including gram-positive and gram-negative bacteria, yeast, protozoa and certain strains of virus. Accordingly, they can be used in disinfectant compositions and as preservatives for materials such as foodstuffs, cosmetics, medicaments, or other materials containing nutrients for organisms. For use in such contexts, the protegrins are supplied either as a single protegrin, in admixture with several other protegrins, or in admixture with additional antimicrobial agents. In general, as these are preservatives in this context, they are usually present in relatively low amounts, of less than 5%, by weight of the total composition, more preferably less than 1%, still more preferably less than 0.1%.

The peptides of the invention are also useful as standards in antimicrobial assays and in assays for determination of capability of test compounds to bind to endotoxins such as lipopolysaccharides.

For use as antimicrobials or antivirals for treatment of animal subjects, the protegrins of the invention can be formulated as pharmaceutical or veterinary compositions. Depending on the subject to be treated, the mode of administration, and the type of treatment desired—e.g., prevention, prophylaxis, therapy; the protegrins are formulated in ways consonant with these parameters. A summary of such techniques is found in Remington's *Pharmaceutical Sciences*, latest edition, Mack Publishing Co., Easton, Pa.

The protegrins are particularly attractive as an active ingredients pharmaceutical compositions useful in treatment of sexually transmitted diseases, including those caused by *Chlamydia trachomatis, Treponema pallidum, Neisseria gonorrhoeae, Trichomonas vaginalis,* Herpes simplex type 2 and HIV. Topical formulations are preferred and include creams, salves, oils, powders, gels and the like. Suitable topical excipient are well known in the art and can be adapted for particular uses by those of ordinary skill.

In general, for use in treatment or prophylaxis of STDs, the protegrins of the invention may be used alone or in combination with other antibiotics such as erythromycin, tetracycline, macrolides, for example azithromycin and the cephalosporins. Depending on the mode of administration, the protegrins will be formulated into suitable compositions to permit facile delivery to the affected areas. The protegrins may be used in forms containing one or two disulfide bridges or may be in linear form. In addition, use of the enantiomeric forms containing all D-amino acids may confer advantages such as resistance to those proteases, such as trypsin and chymotrypsin, to which the protegrins containing L-amino acids are less resistant.

The protegrins of the invention can be administered singly or as mixtures of several protegrins or in combination with other pharmaceutically active components. The formulations may be prepared in a manner suitable for systemic administration or topical or local administration. Systemic formulations include those designed for injection (e.g., intramuscular, intravenous or subcutaneous injection) or may be prepared for transdermal, transmucosal, or oral administration. The formulation will generally include a diluent as well as, in some cases, adjuvants, buffers, preservatives and the like. The protegrins can be administered also in liposomal compositions or as microemulsions.

If administration is to be oral, the protegrins of the invention must be protected from degradation in the stomach using a suitable enteric coating. This may be avoided to some extent by utilizing amino acids in the D-configuration, thus providing resistance to protease. However, the peptide is still susceptible to hydrolysis due to the acidic conditions of the stomach; thus, some degree of enteric coating may still be required.

As described in the examples below, the peptides of the invention retain their activity against microbes in the context of borate solutions that are commonly used in eye care products. It has also been shown that when tested for antimicrobial activity against *E. coli* in the presence and absence of lysozyme in borate buffered saline, that the presence of lysozyme enhanced the effectiveness of PG-3. This effect was more pronounced when the PG-3 was autoclaved and similar patterns were obtained for both the free-acid form and the amide. Accordingly, the protegrins may be used as preservatives in such compositions or as antimicrobials for treatment of eye infections.

It is particularly important that the protegrins retain their activity under physiological conditions including relatively high saline and in the presence of serum. In addition, the protegrins are not cytotoxic with respect to the cells of higher organisms. These properties, described herein below in the Examples, make them particularly suitable for in vivo and therapeutic use.

The protegrins of the invention may also be applied to plants or to their environment to prevent viral- and microbial-induced diseases in these plants. Suitable compositions for this use will typically contain a diluent as well as a spreading agent or other ancillary agreements beneficial to the plant or to the environment.

Thus, the protegrins of the invention may be used in any context wherein an antimicrobial and/or antiviral action is required. This use may be an entirely in vitro use, or the peptides may be administered to organisms.

In addition, the antimicrobial or antiviral activity may be generated in situ by administering an expression system suitable for the production of the protegrins of the invention. Such expression systems can be supplied to plant and animal subjects using known techniques. For example, in animals, pox-based expression vectors can be used to generate the peptides in situ. Similarly, plant cells can be transformed with expression vectors and then regenerated into whole plants which are capable of their own production of the peptides.

A particularly useful property of the protegrins is their activity in the presence of serum. Unlike defensins, protegrins are capable of exerting their antimicrobial effects in the presence of serum.

As shown hereinbelow, the protegrins are capable of inactivating endotoxins derived from gram-negative bacteria—i.e., lipopolysaccharides (LPS)—in standard assays. Accordingly, the protegrins may be used under any circumstances where inactivation of LPS is desired. One such situation is in the treatment or amelioration of gram-negative sepsis.

The protegrins of the invention, therefore, represent a peculiarly useful class of compounds because of the following properties:

1) they have an antimicrobial effect with respect to a broad spectrum of target microbial systems, including viruses, including retroviruses, bacteria, fungi, yeast and protozoa.

2) Their antimicrobial activity is effective under physiological conditions—i.e., physiological saline and in the presence of serum.

3) They are not toxic to the cells of higher organisms.

4) They can be prepared in nonimmunogenic form thus extending the number of species to which they can be administered.

5) They can be prepared in forms which are resistant to certain proteases suggesting they are antimicrobial even in lysosomes.

6) They can be prepared in forms that resist degradation when autoclaved, thus simplifying their preparation as components of pharmaceuticals.

The following examples are intended to illustrate but not to limit the invention.

EXAMPLE 1

Isolation of PG-1, PG-2 and PG-3

Fresh porcine blood was collected into 15-liter vessels containing 5% EDTA in normal saline, pH 7.4 as an anticoagulant (33 ml/liter blood). The blood cells were allowed to sediment for 90 minutes at room temperature and the leukocyte-rich supernatant was removed and centrifuged at 200× g for 5.7 minutes. The pellets were pooled and suspended in 0.84% ammonium chloride to lyse erythrocytes and the resulting leukocytes (70–75% PMN, 5–10% eosinophils, 15–25% lymphocytes and monocytes) were washed in normal saline, resuspended in ice-cold 10% acetic acid at $10^8$/ml, homogenized and stirred overnight at 4° C.

The preparation was centrifuged at 25,000× g for 3 hours at 4° C. and the supernatant was lyophilized and weighed.

950 mg (dry weight) of lyophilized extract, which contained 520 mg protein by BCA analysis, was stirred overnight at 4° C. in 100 ml of 10% acetic acid and then centrifuged at 25,000× g for 2 hours. The supernate was removed and passed by pressure through a 50 ml stirred ultracentrifugation cell (Amicon, Danvers Mass.) that contained a YM-5 filter. The ultrafiltrate (24.5 mg protein by BCA) was concentrated to 3 ml by vacuum centrifugation (Speedvac Concentrator, Savant Instruments, Hicksville, N.Y.), applied to a 2.5×117 cm BioGel P10 column (Bio-Rad, Hercules, Calif.) and eluted at 4° C. with 5% acetic acid.

Fractions containing 6.6 ml were obtained. Fractions were assayed by absorption at 280 nm and the elution pattern is shown in FIG. 1.

Figure 2:
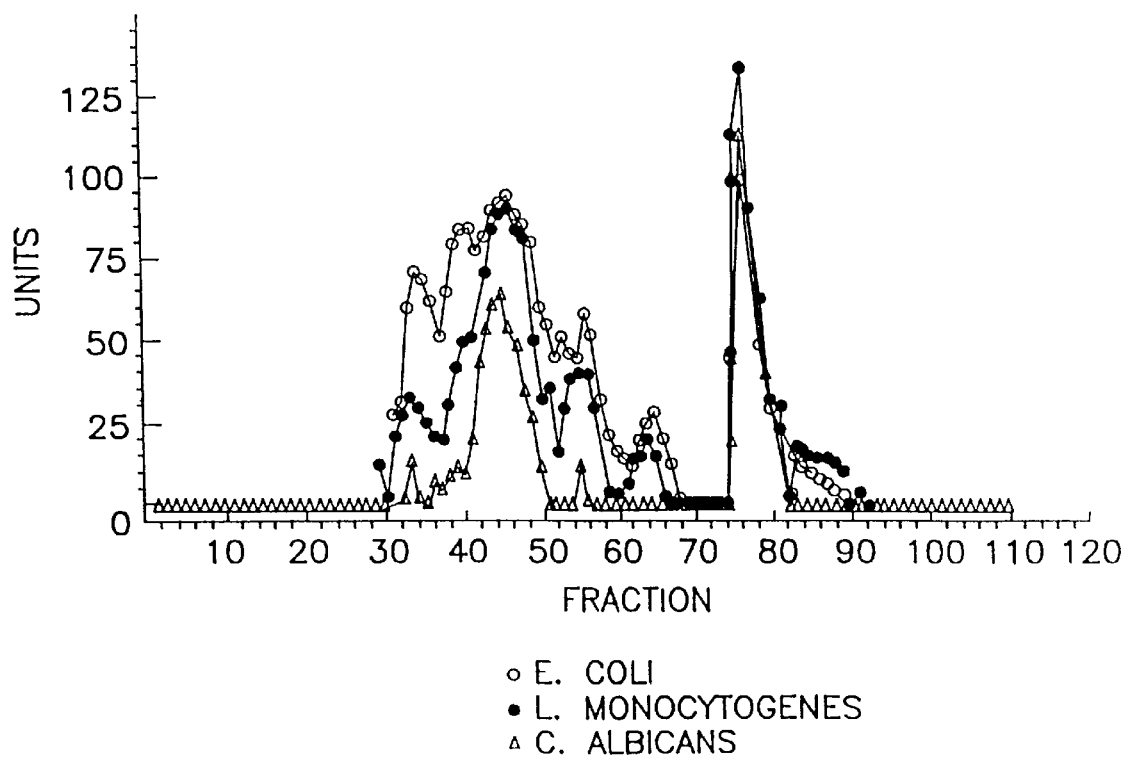
FIG. 2 shows the antibacterial activity of the P10 fractions obtained from elution of the column described in FIG. 1.

Aliquots (66 μl) of each fraction were dried by vacuum centrifugation and resuspended in 6.6 μl of 0.01% acetic acid. Five μl samples of this concentrate were tested for antimicrobial activity against *E. coli* ML-35, *L. monocytogenes*, strain EGD and *C. albicans*, strain 820, using radiodiffusion and gel overlay techniques as described by Lehrer, R. I. et al. *J Immunol Meth* (1991) 137:167–173. Briefly, the underlay agars used for all organisms had a final pH of 6.5 and contained 9 mM sodium phosphate/1 mM sodium citrate buffer, 1% w/v agarose and 0.30 μg/ml tryptocase soy broth powder (BBL Cockeysville, Md.). The units of activity in the radial diffusion assay were measured as described; 10 units correspond to a 1 mm diameter clear zone around the sample well. Activities obtained for the various fractions are shown in FIG. 2. Activity was found in a large number of fractions.

The active fractions were further examined by acid-urea PAGE (AU-PAGE) and SDS PAGE. Results of these analyses showed that active antimicrobial peptides of the appropriate molecular weight were present and concentrated in fractions 76–78.

Figure 3:
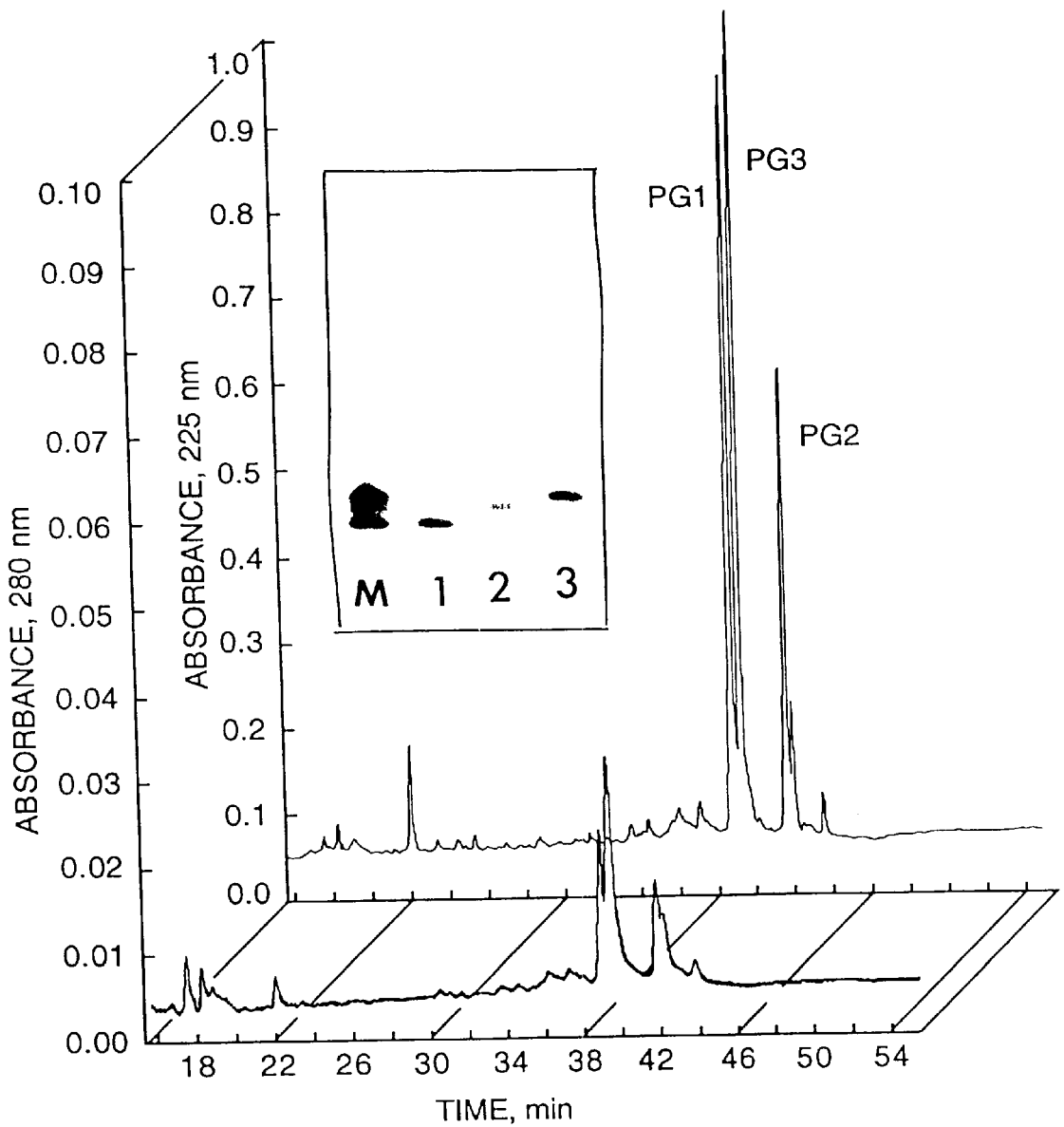
FIG. 3 shows an elution pattern obtained when fractions 76–78 from the Biogel P10 column of FIG. 1 is applied to HPLC.

Fractions 76–78 from the Biogel P10 column were then pooled and chromatographed on a 1×25 cm Vydac 218 TP1010 column with a gradient (buffer A is 0.1% TFA; buffer B is 0.1% TFA in acetonitrile) the increase in acetonitrile concentration was 1% per minute. The results, assessed in terms of absorbance at 280 nm and at 225 nm are shown in FIG. 3. The peaks corresponding to the three peptides illustrated herein are labeled in the figure. The figure also contains an inset which shows the results of an acid-urea PAGE gel stained with Comassie Blue that contains a starting mixture composed of the pooled fractions and the individual PG species. These are labeled M, 1, 2 and 3 on the inset. The results clearly show the presence of three distinct proteins.

The isolated proteins were subjected to amino acid analysis using three independent methods, and to Edman degradation, chymotrypsin digestion, and fast atom bombardment mass spectrometric analysis. The peptides, named "protegrins", are shown to have the amino acid sequences as follows:

PG-1: RGGRLCYCRRRFCVCVGR (SEQ ID NO: 16)
PG-2: RGGRLCYCRRRFCICV (SEQ ID NO: 17)
PG-3: RGGGLCYCRRRFCVCVGR, (SEQ ID NO: 18)
and are amidated at the C-terminus.

The amidation status of the isolated peptides was established by synthesis of PG-3 both in the free carboxyl and carboxyamidated forms. These synthetic peptides were then compared to isolated PG-3 using AU-PAGE and also using reverse-phase HPLC. In both cases, the native product comigrated with the synthetic amidated form.

The location of the disulfide linkages in the isolated protegrins was also studied using PG-2 as a model. The determination was performed using sequential enzyme digestion (chymotrypsin followed by thermolysin) with direct analysis using LC-ESI-MS on the fragments obtained. The results of these analyses showed that the two intramolecular disulfide bonds were $C_6$–$C_{15}$ and $C_8$–$C_{13}$. With the location of the disulfides in these positions, the protegrin molecules are likely to exist as anti-parallel βsheets similar to the tachyplesins in overall conformation.

The antimicrobial proteins above are present in much lower concentrations in initial extracts than are the rabbit defensins in corresponding crude extracts where the defensins constitute more than 15% of the total protein in rabbit granulocytes. Using the AU-PAGE analytical method on the various stages of purification, the peptides are only faintly visible in the crude extracts, whereas corresponding crude extracts of rabbit granulocytes clearly show the presence of the defensins. The peptides of the invention become clearly evident only after the ultrafiltration step.

Because the protegrins whose structures are set forth above show sequence homology to the decapeptide region corresponding to residues 1–10 of rabbit defensin NP-3a in the decapeptide region at positions 4–13 of PG-3, the protegrins, and in particular PG-3, may share the property of defensin NP-3a in being capable of competitively antagonizing ACTH-mediated steroid synthesis by adrenocytes. This property, called "corticostasis", may influence the effectiveness of the protegrins as antiinfectious agents when employed in vivo.

EXAMPLE 2

Antimicrobial Activity

Figure 4A:
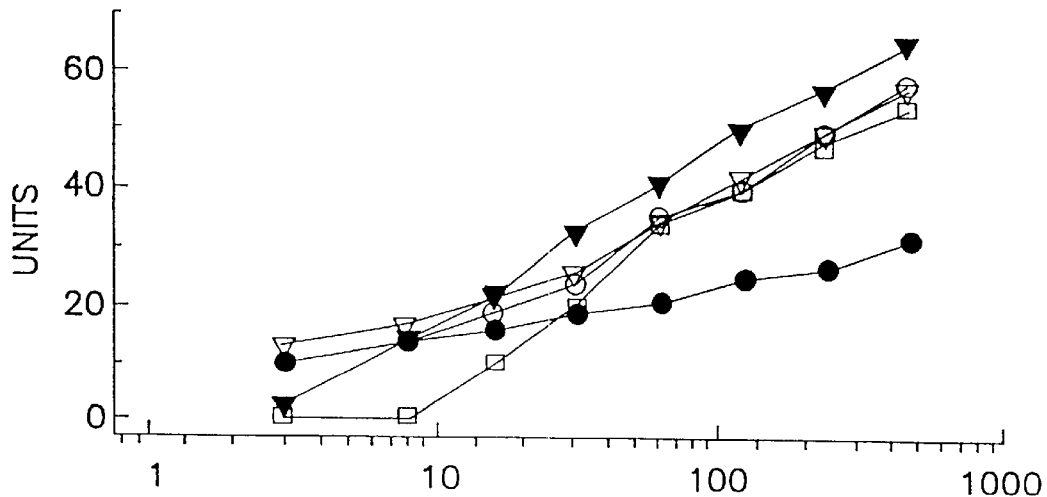
FIG. 4a shows antibacterial activity against E. Coli.
Figure 4B:
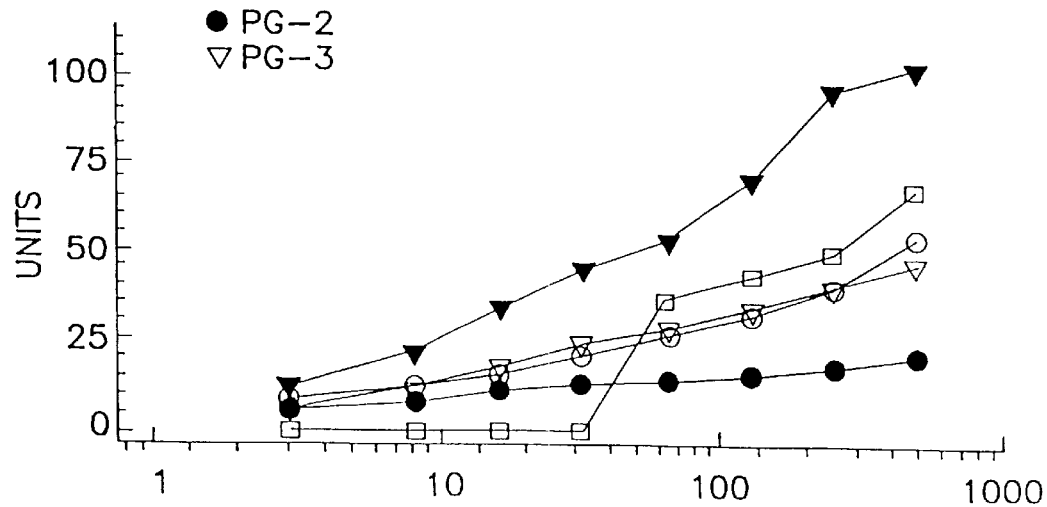
FIG. 4b shows antibacterial activity against Listeria monocytogenes.
Figure 4C:
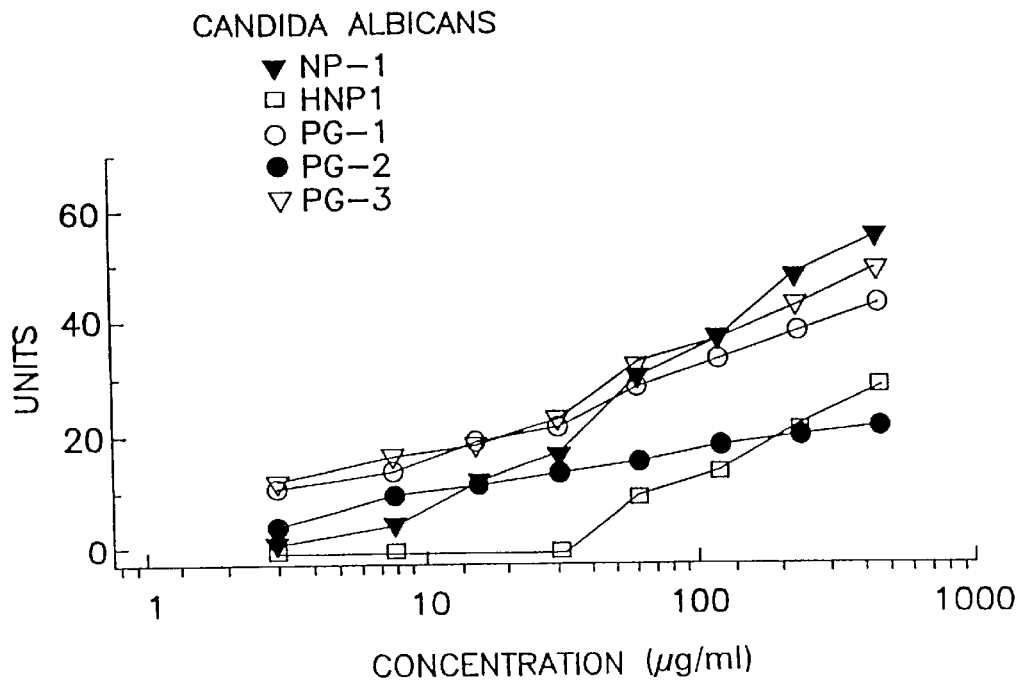
FIG. 4c shows antifungal activity against Candida albicans.
Figure 4D:
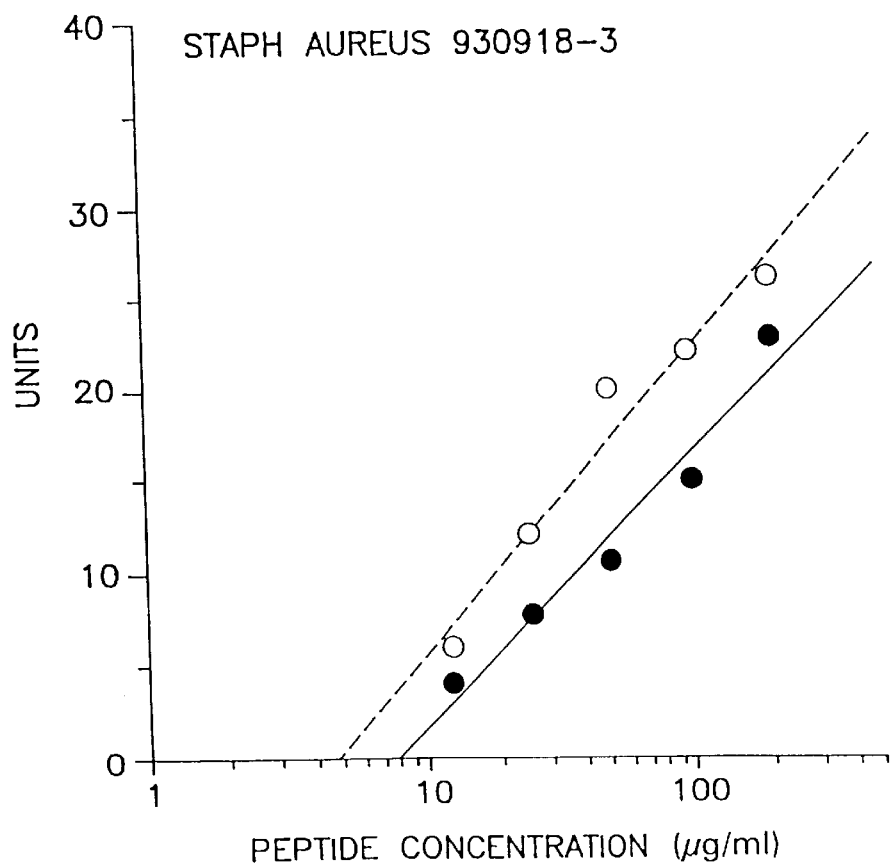
FIG. 4d shows antibacterial activity against S. aureus.
Figure 4E:
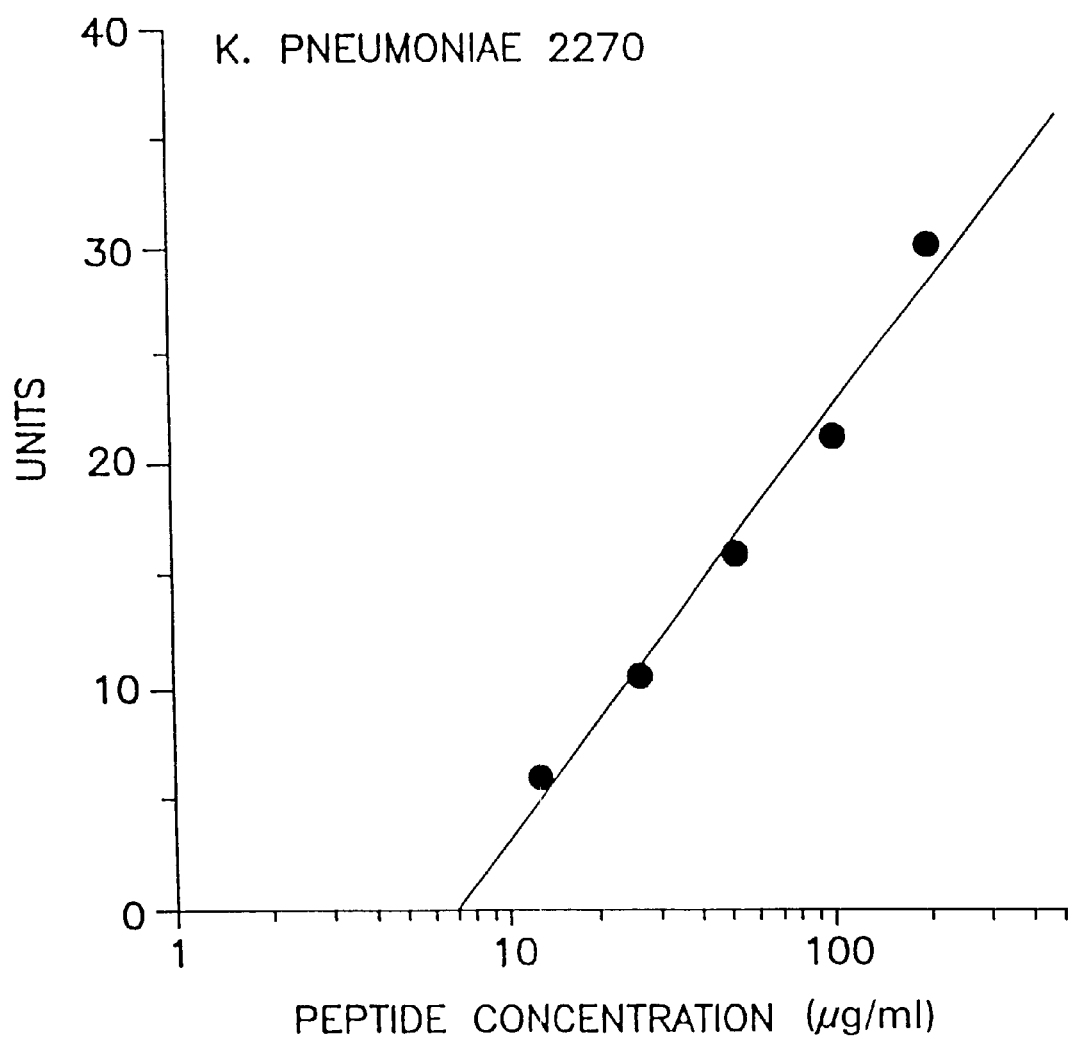
FIG. 4e shows antibacterial activity against K. pneumoneae.

The radial diffusion assay in agarose gels described in Example 1 was also used to test the activity of the purified protegrins. FIGS. 4a, 4b and 4c show the results against three test organisms in units described as above. The rabbit defensin (NP-1) and the human defensin (HNP-1) were used as controls.

FIG. 4a shows that PG-1 and PG-3 are more effective against *E. coli* ML-35P than HNP-1 and only slightly less effective than NP-1. PG-1 and PH-3 were also effective against Listeria monocytogenes, strain EGD as shown in FIG. 4b. In FIG. 4c, PG-1 and PG-3 were also shown effective against *Candida albicans*. In general, these peptides are approximately as effective as rabbit defensin NP-1 on a weight basis and are more effective than HNP-1. In all cases, PG-2 was also effective against the three organisms tested but was not as active as the other two peptides.

In addition to its activity in inhibiting the growth of the above-mentioned organisms, the PG-1 of the invention has been shown directly to inhibit the growth of *Staphylococcus aureus* (see Figure) and *K. pneumoneae* 270 (Figure). HNP-1 used as a control was less effective against *S. aureus* and almost entirely ineffective against *K. pneumoneae*.

The protegrins of the invention have also been tested against various other organisms and show broad spectrum activity. In addition to their effectiveness in inhibiting the growth of or infection by microorganisms associated with STDs as described in Example 9 hereinbelow, the protegrins show strong activity against the following microorganisms in addition to those tested hereinabove: *Pseudomonas aeruginosa, Klebsiella pneumoniae, Salmonella* typhimurium, *Staphylococcus aureus, Histoplasma capsulatum, Myobacterium avium-intracellulare*, and *Mycobacterium tuberculosis*. The protegrins showed only fair activity against *Vibrio vulnificus* and were inactive against *Vibrio cholerae* and *Borrelia burgdorferi*.

EXAMPLE 3

Retention of Activity Under Certain Conditions

The antimicrobial activity of the invention compounds was tested as set forth above, but under conditions of 100 μM NaCl and in the presence of 90% fetal calf serum. FIGS. 5a and 5b show that PG-1 and PG-3 retain their activity with respect to *C. albicans* and *E. coli* respectively, even in the presence of 100 mM NaCl. Neither NP-1 nor HNP-1 have this property. FIG. 5c shows that although NP-1 and NHP-2 lose their ability to inactivate *C. albicans* in 90% fetal calf serum, inactivation by PG-3 is retained.

Accordingly, the protegrins of the invention retain their antimicrobial properties under useful physiological conditions, including isotonic and borate solutions appropriate for use in eye care products.

In addition, synthetic PG-1 was tested with respect to its activity against *E. coli* ML-35 (serum sensitive) in underlayered gels containing only 10 mM sodium phosphate buffer, pH 7.4 and a 1:100 dilution of trypticase soy broth, both in the presence and absence of 2.5% normal human serum, which is below the lytic concentration for this strain of *E. coli*. In the presence of serum, the minimal bactericidal concentration was reduced from approximately 1.0 μg/ml to about 0.1 μg/ml. This type of effect was not observed either for a linear fragment of cathepsin G or for the defensin HNP-1.

Similarly, using *C. albicans* as a target organism, underlayers were prepared with 10 mM sodium phosphate with and without 10% normal human serum. The minimal fungicidal concentration fell from about 1.3 μg/ml in the absence of serum to 0.14 μg/ml in its presence. The serum itself at this concentration did not effect *C. albicans*.

Thus, not only is the action of the protegrins not inhibited by the presence of serum, it is enhanced thereby. Similar results were obtained using *L. monocytogenes* as the target organism.

The protegrins PG-1 and PG-3 were incubated for 4 hours at pH 2.0 with 0.5 μg/ml pepsin and then neutralized. The residual antimicrobial activity against *C. albicans, E. coli* and *L. monocytogenes* was assessed and found to be fully retained. Similar experiments show that these compounds are not degraded by human leukocyte elastase or by human leukocyte cathepsin G even when exposed to high concentrations of these enzymes and at a pH of 7.0–8.0 favorable for proteolytic activity. In addition, synthetic PG-3 amide and synthetic PG-3 acid were autoclaved and tested for antimicrobial activity against *E. coli, L. monocytogenes* and *C. albicans*; retaining full antimicrobial activity in all cases. It is possible that the stability of these compounds to protease degradation and to autoclaving is enhanced by the presence of disulfide bonds.

EXAMPLE 4

Ability to Bind Endotoxin

The protegrins of the invention were tested for their ability to bind the lipid polysaccharide (LPS) of the gram-negative bacterium *E. coli* strain 0.55B5. The assay was the Limulus amebocyte lysate (LAL) test for endotoxins conducted in the presence and absence of the test compounds. The test was conducted using the procedure described in Sigma Technical Bulletin No. 210 as revised in December 1992 and published by Sigma Chemical Company, St. Louis, Mo.

The LAL test is based on the ability of LPS to effect gelation in the commercial reagent E-Toxate™ which is prepared from the lysate of circulating amebocytes of the Horseshoe Crab *Limulus polyphemus*. As described in the technical bulletin, when exposed to minute quantities of LPS, the lysate increases in opacity as well as viscosity and may gel depending on the concentration of endotoxin. The technical bulletin goes on to speculate that the mechanism appears analogous to the clotting of mammalian blood and involves the steps of activation of a trypsin-like preclotting enzymes by the LPS in the presence of calcium ion, followed by enzymic modifications of a "coagulogen" by proteolysis to produce a clottable protein. These steps are believed tied to the biologically active or "pyrogenic" portion of the molecule. It has been shown previously that detoxified LPS (or endotoxin) gives a negative LAL test.

The test compounds were used at various concentrations from 0.25 μg–10 μg in a final volume of 0.2 ml and the test mixtures contained LPS at a final concentration of 0.05 endotoxin unit/ml and E-Toxatem at the same concentration. The test compounds were incubated together with the LPS for 15 minutes before the E-Toxate was added to a final volume after E-Toxate™ addition of 0.2 ml. The tubes were then incubated for 30 minutes at 37° C. and examined for the formation of a gel.

Both isolated native protegrins (nPGs) and synthetically prepared protegrins (sPGs) were tested. The sPGs were prepared with a carboxyl group at the C-terminus or with an amidated C-terminus. The nPGs are amidated at the C-terminus. Also tested were six different rabbit defensins (NPs) and four native human defensins (HNPs). The results are shown in Table 1.

TABLE 1

| Peptide | 10 μg | 5 μg | 2.5 μg | 1.0 μg | 0.5 μg | 0.25 μg |
| --- | --- | --- | --- | --- | --- | --- |
| nPG-1 | no gel | no gel | no gel | no gel | + | ++ |
| nPG-2 | no gel | no gel | no gel | no gel | + | ++ |
| nPG-3 | no gel | no gel | trace | ++ | ++ | ++ |
| sPG-3 acid | no gel | no gel | trace | ++ | ++ | ++ |
| sPG-3 amide | no gel | no gel | no gel | + | ++ | ++ |
| NP-1 | not tested | not tested | ++ | ++ | ++ | ++ |
| NP-2 | trace | + | + | ++ | ++ | ++ |
| NP-3a | no gel | no gel | no gel | ++ | ++ | ++ |
| NP-3b | no gel | no gel | + | ++ | ++ | ++ |
| NP-4 | not tested | not tested | + | ++ | ++ | ++ |
| NP-5 | no gel | trace | + | + | ++ | ++ |
| HNP-1 | no gel | + | + | ++ | ++ | ++ |
| HNP-2 | trace | trace | trace | + | + | ++ |
| HNP-3 | no gel | + | + | ++ | ++ | ++ |
| HNP-4 | no gel | trace | trace | ++ | + | ++ |

As seen from the results, all of the protegrins, both synthetic and native, and both in the amidated and nonamidated forms are able to bind sufficiently to LPS to prevent any substantial gel formation at concentrations as low as 2.5 μg/0.2 ml. nPG-1 and nPG-2 are effective at somewhat lower concentrations. The protegrins were substantially more effective than the NP or HNP test compounds; the most effective among these controls was NP-3a, a peptide whose primary sequence most closely resembles that of the protegrins.

In a follow-up experiment, the concentration of LPS was varied from 0.05–0.25 endotoxni units (E.U.) and synthetic PG-3 amide was used as the test compound. The results are shown in Table 2.

TABLE 2

| Endotoxin Units | 0.25 E. U. | 0.10 E. U. | 0.05 E. U. |
|---|---|---|---|
| sPG-3 amide (2.5 Tg) | no gel | no gel | no gel |
| sPG-3 amide (1.0 Tg) | no gel | no gel | no gel |
| sPG-3 amide (0.5 Tg) | ++ | ++ | no gel |
| no added protein | ++ | ++ | ++ |

These results show that since inhibition of gelation can be overcome by increasing the concentration of LPS, interaction with LPS is responsible for the lack of gelation, rather than interfering with the gelation enzyme cascade.

EXAMPLE 5

Activity of Linearalized Forms nPG-1 and nPG-3 were converted to linear form using a reducing agent to convert the disulfide linkages to sulfhydryl groups, which were then stabilized by alkylating with iodoacetamide.

The ability of both cyclic and linearalized PG-1 and PG-3 to inhibit gelation in the standard LAL assay was assessed then as described in Example 4 and the results are shown in Table 3.

TABLE 3

| Peptide | 5 µg | 2.5 µg | 1.0 µg | 0.25 µg | |
|---|---|---|---|---|---|
| nPG-1 | no gel | no gel | ++ | ++ | ++ |
| cam-nPG-1 | no gel | no gel | ++ | ++ | ++ |
| nPG-3 | no gel | no gel | ++ | ++ | ++ |
| cam-nPG-3 | no gel | no gel | ++ | ++ | ++ |

These results show that the linearalized and cyclic forms of the protegrins are equally capable of inhibiting gelation and binding to endotoxin.

The antimicrobial activity of the linearalized forms was also compared with that of the native protegrins. Both linearalized and cyclic forms of the protegrins tested continue to show antimicrobial activity, although the effectiveness of these peptides as antimicrobials depends on the nature of the target organism and on the test conditions. The antimicrobial activity of native PG-1 and its linearalized form (cam-PG-l) and PG-3 and its linearalized form (cam-PG-3) were tested according to the procedure set forth in Example 1 as described by Lehrer, R. I. et al. *J Immunol Meth* (1991) 137:167–173. The results are set forth in FIGS. 6a–6f.

Figure 6A:
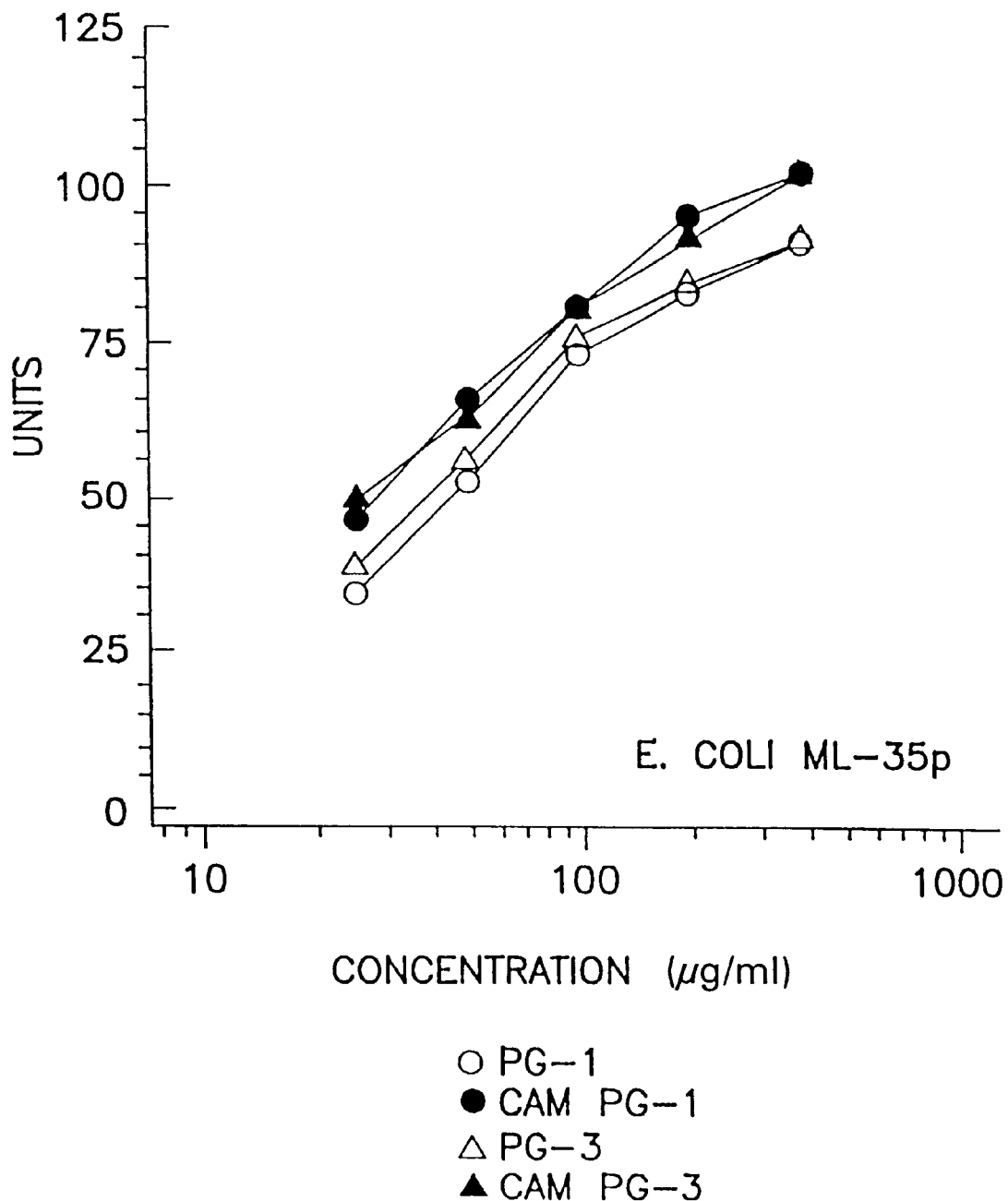
FIG. 6a shows the activity against E. coli in 10 mM phosphate-citrate buffer, pH 6.5.
Figure 6B:
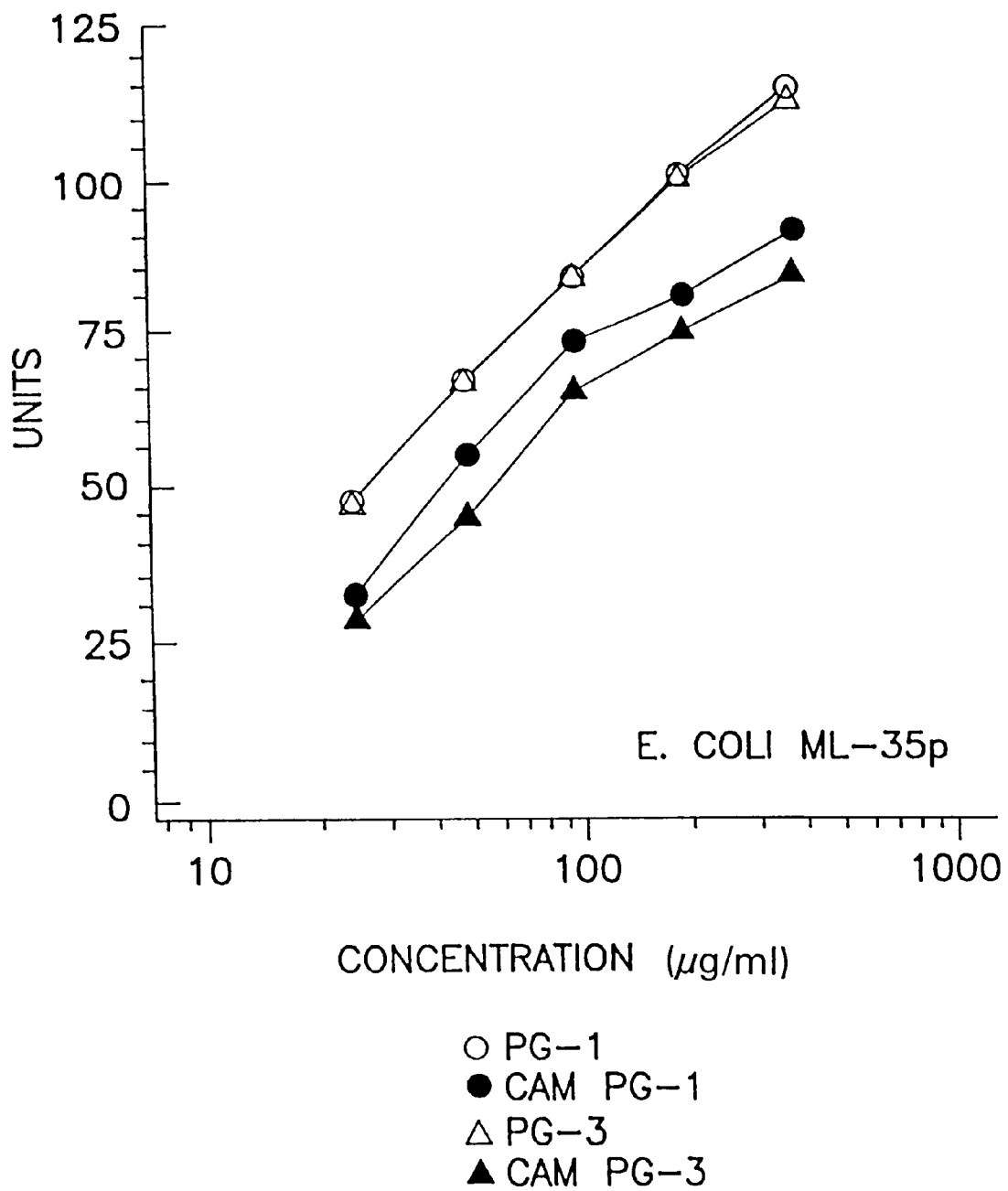
FIG. 6b shows the activity against E. coli in the same buffer with 100 mM NaCl.

FIGS. 6a and 6b show the antimicrobial activity of these peptides in the concentration range 20 µg/ml–125 µg/ml with respect to *E. coli*ML-35P either in 10 mM phosphate-citrate buffer, pH 6.5 (FIG. 6a) or in the presence of this buffer plus 100 mM NaCl (FIG. 6b). Both protegrins showed strong antimicrobial activity with respect to this organism; the linear form was slightly more potent in the presence of buffer alone than was the cyclic form; on the other hand, the cyclic form was more potent than the linear form under isotonic conditions.

Figure 6C:
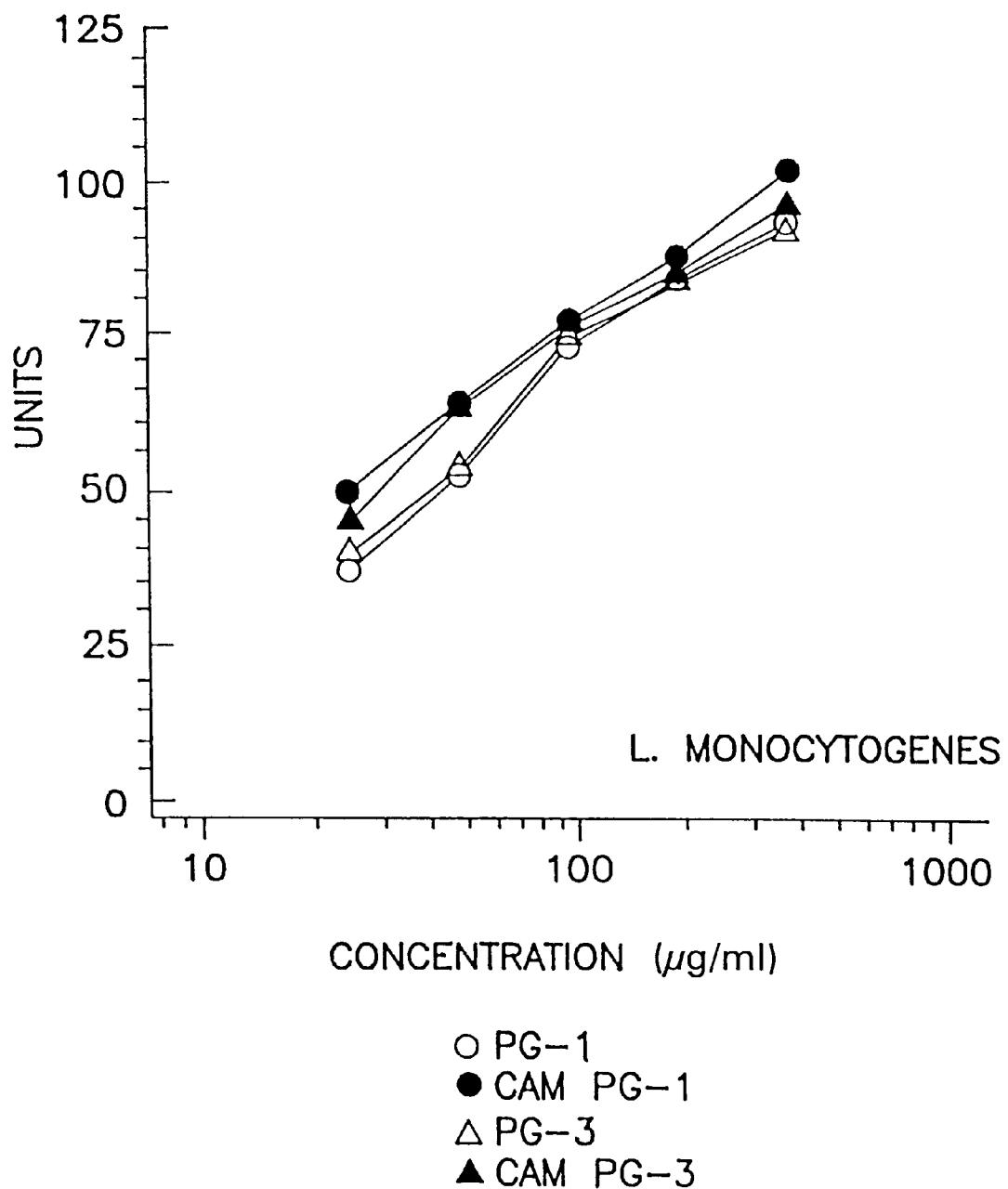
FIG. 6c shows the activity against L. monocytogenes in the buffer of FIGS. 6a–6b.
Figure 6D:
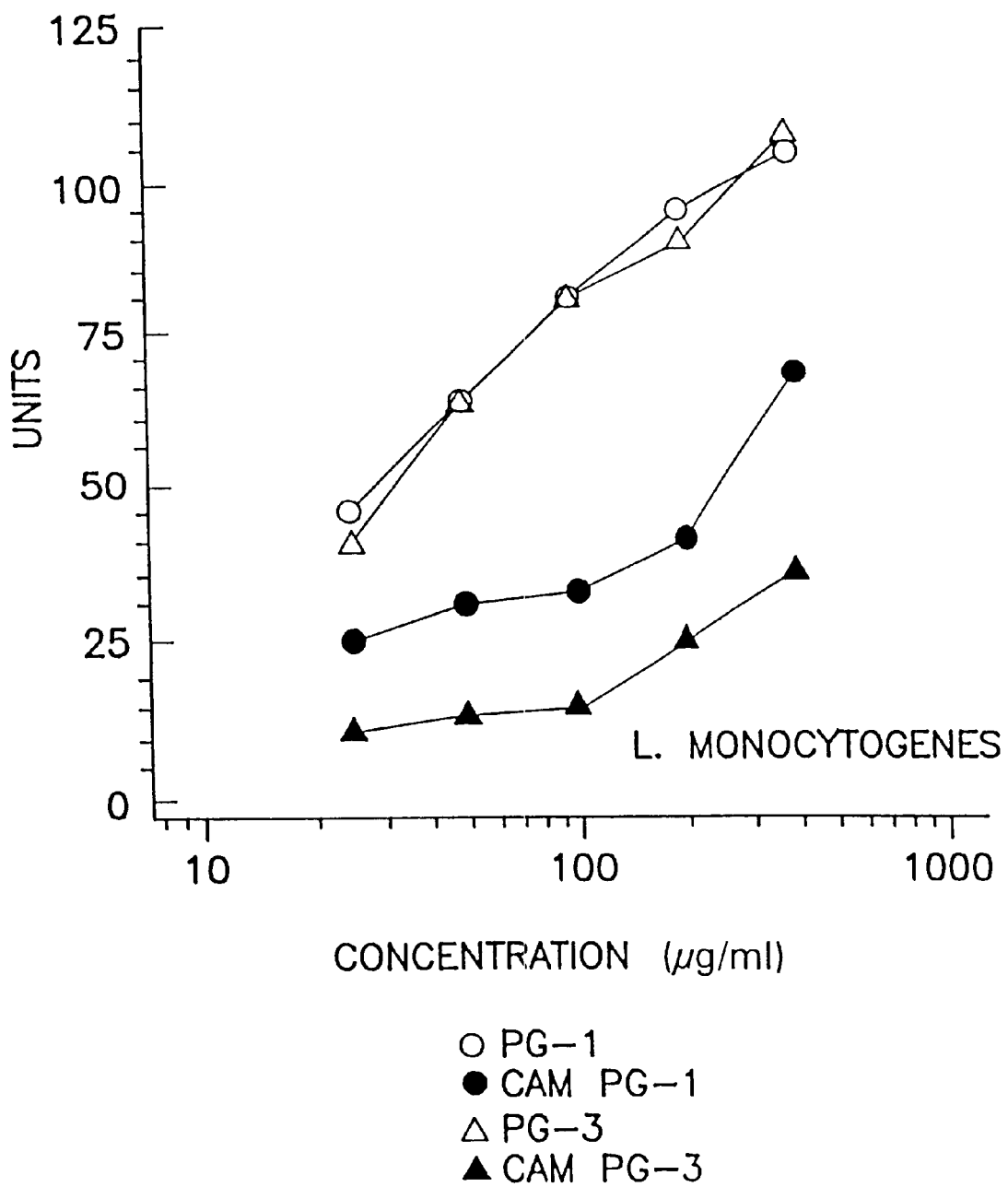
FIG. 6d shows the activity against L. monocytogenes in the same buffer with the addition of 100 mM NaCl.

FIGS. 6c and 6d show the antimicrobial effect with respect to *L. monocytogenes*. In FIG. 6c where the above-mentioned buffer alone was used, both cyclic and linearalized forms of the protegrins showed strong antimicrobial activity and both were approximately equally effective over the concentration range tested (20 µg/ml–125 µg/ml).

FIG. 6d shows the effect with respect to *L. monocytogenes* in the presence of this buffer plus 100 mM NaCl over the same concentration range. The cyclic form retained strong antimicrobial activity with a slightly greater concentration dependence. Linearalization appeared to lower the activity appreciably although high concentrations were still able to show an antimicrobial effect.

Figure 6E:
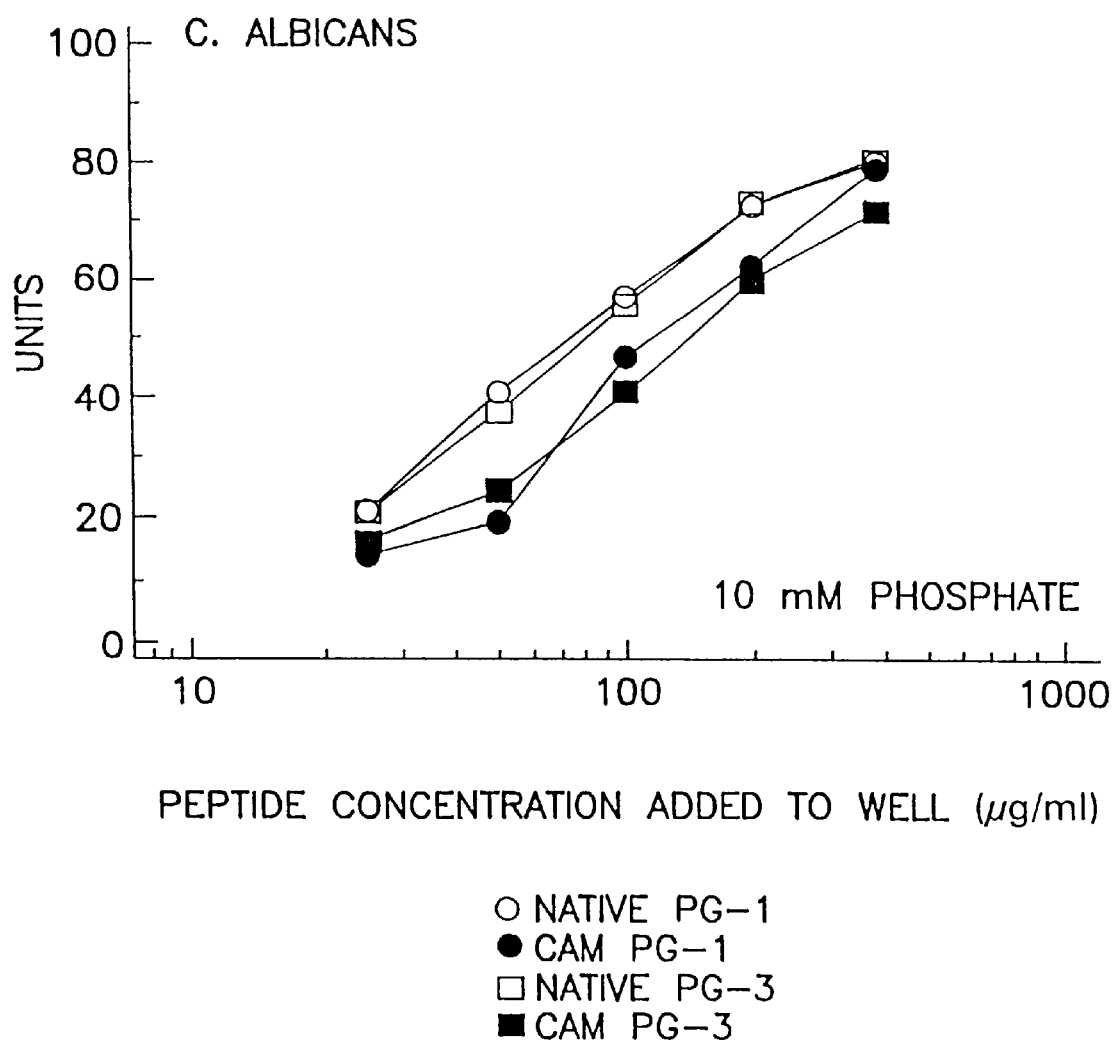
FIG. 6e shows the activity against C. albicans in the presence of 10 mM phosphate.
Figure 6F:
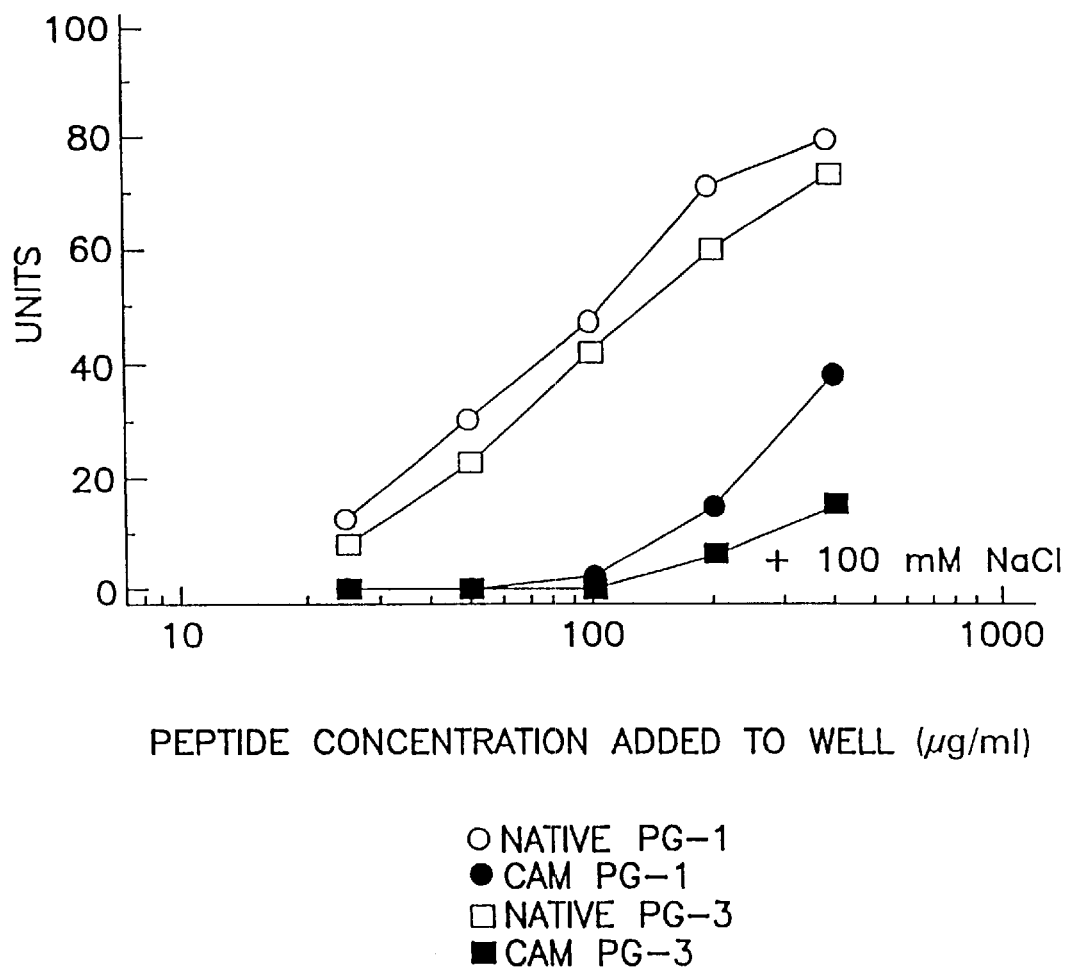
FIG. 6f shows the activity against C. albicans in the presence of 10 mM phosphate plus 100 mM NaCl.

The yeast *C. albicans* was tested with the results shown in FIGS. 6e and 6f. FIG. 6e shows that all forms of these protegrins were antimicrobial in a dose-dependent manner over the above concentration range when tested in the presence of 10 mM phosphate buffer alone, although the linearalized peptides were very slightly less effective. FIG. 6f shows the results of the same assay run in the presence of buffer plus 100 mM NaCl. While the cyclized forms retained approximately the same level of antimicrobial effect, the activity of the linearalized forms was greatly diminished so that at concentrations below 100 µg/ml of the protegrin, virtually no antimicrobial effect was seen. However, at higher concentrations of 130 µg/ml, a moderate antimicrobial effect was observed.

Thus, depending on the target microorganism and the conditions used, both the cyclized and linearalized forms of the protegrins have antimicrobial activity.

EXAMPLE 6

Antimicrobial Activity Under Conditions Suitable for Treatment of the Eye

Contact lens solutions are typically formulated with borate buffered physiological saline and may or may not contain EDTA in addition. Protegrins in the form of the synthetic PG-3 amide and synthetic PG acid were tested generally in the assay described in Example 1 wherein all underlay gels contain 25 mM borate buffer, pH 7.4, 1% (v/v) tryptocase soy broth (0.3 µg/ml TSB powder) and 1% agarose. Additions included either 100 mM NaCl, 1 mM EDTA or a combination thereof. Other test compounds used as controls were the defensin NP-1 and lysozyme. Dose response curves were determined.

Table 4 shows the estimated minimal bacteriocidal concentrations in µg/ml of the various test compounds.

TABLE 4

| ESTIMATED MINIMAL FUNGICIDAL CONCENTRATIONS (µg/ml) | | | | |
|---|---|---|---|---|
| Peptide | buffer | + EDTA | + NaCl | + EDTA & NaCl |
| sPG-3 amide | 13.0 | 9.5 | 4.1 | 3.1 |
| sPG-3 acid | 15.0 | 9.5 | 4.6 | 3.7 |
| NP-1 | 35.0 | 45.0 | >200 | >200 |
| lysozyme | 75.0 | 45.0 | >200 | >200 |

Although protegrins are somewhat less active in 25 mM borate buffered saline than in 25 mM phosphate buffer, the antimicrobial activity is enhanced by adding physiological saline and modestly enhanced by 1 mM EDTA, as shown in the table.

A similar test was run with *Candida albicans* as the target organism with the results shown in Table 5, which also shows estimates of minimal fungicidal concentrations.

TABLE 5

ESTIMATED MINIMAL FUNGICIDAL CONCENTRATIONS
(μg/ml)

| Peptide | 25 mM borate buffer | borate buffer + 120 mM NaCl | borate buffer + EDTA & NaCl |
|---|---|---|---|
| nPG-3 | 32.0 | 9.0 | 8.0 |
| sPG-3 amide | 19.0 | 7.7 | 7.0 |
| sPG-3 acid | 19.0 | 9.2 | 9.3 |
| NP-1 | 23.0 | 60.0 | 65.0 |
| HNP-1 | 25.0 | >200 | >200 |

Table 6 shows results of similar experiments conducted with *L. monocytogenes* as the target.

TABLE 6

ESTIMATED MINIMAL BACTERICIDAL CONCENTRATIONS
(μg/ml)

| Peptide | 25 mM borate buffer | borate buffer + 120 mM NaCl | borate buffer + EDTA & NaCl |
|---|---|---|---|
| nPG-3 | 25.0 | 7.0 | 5.7 |
| sPG-3 amide | 21.0 | 5.7 | 5.2 |
| sPG-3 acid | 30.0 | 7.0 | 7.0 |
| NP-1 | 20.0 | 11.0 | 3.8 |
| HNP-1 | 11.0 | >200 | >200 |

The results shown indicate that these compounds are capable of exerting their antimicrobial effects under conditions typically associated with conditions suitable for eye care products.

EXAMPLE 7

Recovery of cDNA Clones and of a New Protegrin-Encoding cDNA cDNA Generation and PCR Amplification.

Total RNA was extracted from the bone marrow cells of a young red Duroc pig with guanidinium thiocyanate. One μg of total RNA was used to synthesize the first strand cDNA, with 20 pmol Oligo(dT) primer and 200 U Moloney-murine leukemia virus (M-MLV) reverse transcriptase (Clontech Laboratory, Palo Alto, Calif.) in a total reaction volume of 20 μl. Two PCR primers were prepared. The sense primer (5'-GTCGGAATTCATGGAGACCCAGAG (A or G) GCCAG-3' (SEQ ID NO: 68)) corresponded to the 5' regions of PG-2 and PR-39 cDNA and contained an EcoRI restriction site. The antisense primer (5'-GTCGTCTAGA(C or G) GTTTCACAAGAATTTATTT-3' (SEQ ID NO: 69)) was complementary to 3' ends of PG-2 and PR-39 cDNA immediately preceding their poly A tails and contained an XbaI restriction site. PCR was carried out in a 50 μl volume using 1/10 volume of the above pig cDNA as template, 25 pmol primers and 2.5 units of AmpliTaq DNA polymerase (Perkin Elmer-Cetus). The reaction was run for 30 cycles, with 1 min denaturation (94° C.) and annealing (60° C.) steps and a 2 min extension step (72° C.) per cycle.

cDNA Cloning and Sequencing. The amplified cDNA was fractionated by preparative agarose electrophoresis and stained with ethidium bromide. The main fragment was cut out, digested with EcoR I and Xba I endonucleases (New England Biolabs, Beverly, Mass.), subcloned into a M13mp18 bacteriophage vector, and transformed into *E. coli* XL1-Blue MRF' competent cells (Stratagene, La Jolla, Calif.). DNA sequencing was performed with a kit (U.S. Biochemical Corp., Cleveland, Ohio). Nucleotide and protein sequences were analyzed with PC-GENE (Intelligenetics, Palo Alto, Calif.).

Northern blots. Ten μg of total RNA was denatured in 50% formamide, separated by electrophoresis through 1% agarose gels in 0.62 M formaldehyde, and blotted onto GeneScreen Plus membranes (DuPont, Boston, Mass.) by capillary transfer. The membrane was baked at 80° C. for 2 h, and hybridized with $^{32}$P-labeled probe in rapid hybridization buffer (Amersham, Arlington Height, Ill.).

The results of sequencing the various clones encoding the various protegrins is summarized in FIG. 7. The cDNA sequences of protegrins PG-1, PG-3 and PG-4 contain 691 bases as had previously been shown for PG-2 by Storici, P. et al. *Biochem Biophys Res Comm* (1993) 196:1363–1368. The cDNAs show an upstream sequence encoding 110 amino acids which appears identical for all protegrins. Additional differences, which are quite slight in nature, are shown in FIG. 7.

The analysis showed the presence of the protegrin PG-4 having an amino acid sequence of Formula (1) wherein $A_{10}$ is a small amino acid and $A_{11}$ is a hydrophobic amino acid as distinguished from the previously known protegrins where these residues are basic. The amino acid sequence of PG-4 is therefore RGGRLCYCRGWICFCVGRG, (SEQ ID NO: 70) wherein 1, 2, or 3 amino acids at the N-terminus may be deleted.

Additional clones were obtained by amplifying reverse transcribed porcine bone cell RNA using an upstream primer that corresponds to the 5' end of PG-2 and another cathelin-associated peptide, PR39, (Agerbeth B et al., *Eur J Biochem* (1991) 202:849–854; Storici, P et al., *Biochem Biophys Res Com* (1993) 186:1058–1065) and downstream primer that matches the region immediately preceding the poly A region. The resulting approximately 0.7 kb PCR product was subcloned into M13mp18 and recombinant plaques were chosen for purification and sequencing. In this manner, the sequences for the precursors of PG-1, PG-3 and PG-4 were recovered. All of these peptides are encoded by a nucleotide sequence which encodes a precursor containing additional amino acid sequence upstream of $A_1$ of the compound of formula 1 (as shown for PG-4 in FIG. 7).

EXAMPLE 8

Recovery of Genomic DNA Encoding PG-1, PG-3, and PG-5

High molecular genomic DNA was purified from pig white blood cells with the QIAGEN blood DNA kit (QIAGEN, Chatsworth, Calif.). To amplify protegrin (PG) genes, PCR was performed using genomic DNA as a template.

The sense primer (5'-GTCGGAATTCATGGAGACCCAGAG(A or G)GCCAG-3' (SEQ ID NO: 68)) corresponded to the 5' regions of PG cDNAs, of Example 7 and provided an EcoRI restriction site. The antisense primer (5'-GTCGTCTAGA(C or G)GTTTCACAAGAATTTATTT-3' (SEQ ID NO: 69)) was complementary to 3' ends of PG cDNAs immediately preceding their poly(A) tails and provided an XbaI restriction site. The reaction was carried out in a total volume of 50 μl, which contained 200 ng of purified pig genomic DNA, 25 pmoles of each primer, 1 μl of 10 mM dNTP, 5 μl of 10× PCR buffer (200 mM Tris-HCl, 100 mM(NH$_4$)$_2$, 20 mM MgSO$_4$, 1% Triton X-100, 0.1% BSA), and 2.5 units of cloned Pfu DNA polymerase (Stratagene, La Jolla, Calif.).

Thirty cycles were performed, each with 1 min of denaturation at 94° C., 1 min of primer annealing at 55° C., 2 min of primer extension at 72° C., and a final extension step at 72° C. for 10 min.

The amplified PCR product was digested with EcoRI and XbaI, excised from the agarose gel, purified, and ligated into pBluescript KS+ vector (Stratagene, La Jolla, Calif.) that had been digested with EcoRI and XbaI and purified. Both strands of DNA were sequenced by the dideoxy method using the Sequenase version 2.0 kit (United States Biochemical, Cleveland, Ohio), pBluescript universal primers and specific oligomer primers based on PG genomic and cDNA sequences. Computer analysis of the DNA sequences was performed using the PC-Gene Program (Intelligenetics, Palo Alto, Calif.).

A PCR product of about 1.85 kb was confirmed as protegrin-related by hybridization with a protegrin-specific oligonucleotide probe complementary to nt 403–429 of the protegrin cDNA sequences. The PCR product was then subcloned into pBluescript vector, and recombinant plasmids were subjected to DNA purification and sequencing. Gene sequences for three different protegrins were identified PG-1, PG-3 and PG-5. The nucleotide sequences and deduced amino acid sequences are shown in FIG. 8.

Figure 9:
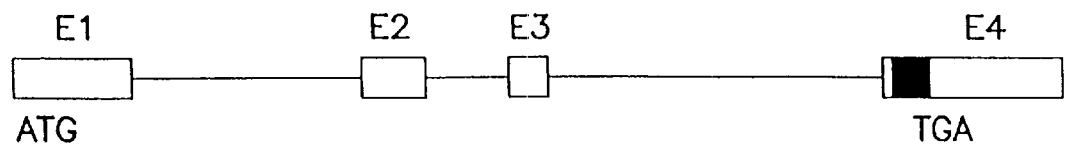
FIG. 9 shows the organization of the protegrin genomic DNA.

Comparison of protegrin cDNAs and genes revealed that the coding regions of protegrin genes consisted of four exons, interrupted by three introns (FIGS. 8 and 9). The first exon contained the 5' noncoding region and codons for the first 66 amino acids of the protegrin prepropeptide, including a 29 residue signal peptide and the first 37 cathelin residues. Exons II and III were relatively small, only 108 and 72 bp respectively, and together contained the next 60 cathelin residues. The final two cathelin residues were on Exon IV, and were followed by the protegrin sequences. The exon-intron splice site sequences are shown in Table 7, and conform to the consensus rule: all introns end on an AG doublet, preceded by a T/C rich stretch of 8–12 bases, while all introns start with GT, followed predominantly by A/G A/G G sequence.

TABLE 7

Exon-Intron Structure of the PG-1 Gene

| Exon | Size | 5' splice donor | Intron | Size | 3' splice acceptor |
|---|---|---|---|---|---|
| 1 | ? + 198 | AAGGCCgtgagtcg (SEQ ID NO: 71) | 1 | 405 | ttgaccagGACGAG (SEQ ID NO: 74) |
| 2 | 108 | AACGGGgtgaggct (SEQ ID NO: 72) | 2 | 152 | ccttccagCGGGTG (SEQ ID NO: 75) |
| 3 | 72 | AATGAGgtgagtgg (SEQ ID NO: 73) | 3 | 596 | ggtcacagGTTCAA (SEQ ID NO: 76) |
| 4 | 313 | | | | |

The highly conserved cathelin region spans exons I-IV and Exon IV contains the full sequence of the mature protegrin peptide followed by an amidation consensus sequence, a 3' untranslated region, and the putative polyadenylation site. The three introns range in size from 152 to 596 bp. If the protegrin genes are representative of other cathelin-like genes, the third intron of cathelin-associated peptides will be found to separate all but the last two residues of the highly conserved cathelin region from the variable antimicrobial peptides encoded in Exon IV. Such a layout would favor recombination mechanisms involving association of diverse Exon IVs with the first three exons specifying cathelin containing prepro-regions.

Figure 10:
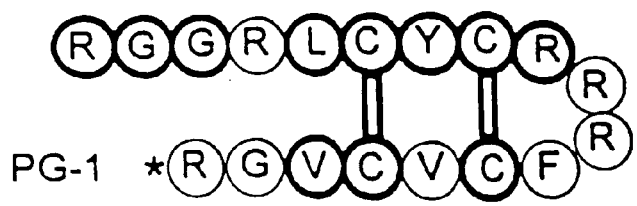
FIG. 10 shows the amino acid sequences of the protegrins PG-1 to PG-5(SEQ ID NOS: 11 through 15).

The family of naturally occurring protegrins thus contains at least 5 members. FIG. 10 shows a comparison of the amino acid sequences of the five protegrins found so far in porcine leukocytes. There is complete homology in positions 1–3, 5–9, 13 and 15–16.

Homology search of protegrin genes against the EMBL/GenBank identified no significantly homologous genes. More specifically, the gene structures and nucleotide sequences of protegrins were very different from those of defensins, which contain three exons in myeloid defensin genes, and two exons in enteric defensin genes. As expected, the search yielded the large family of cDNAs corresponding to cathelin-associated bovine, porcine and rabbit leukocyte peptides.

To assess protegrin-related genes further, we screened a porcine genomic library of approximately $2.3 \times 10^5$ clones in EMBL-3 SP6/T7 with the $^{32}$P-labeled protegrin cDNA, and identified 45 hybridizing clones.

A porcine liver genomic library in EMBL3 SP6/T7 phages was purchased from Clontech (Palo Alto, Calif.). *E. coli* strain K803 was used as a host, and DNA from phage plaques was transferred onto nylon membranes (DuPont, Boston, Mass.). The filters were hybridized with $^{32}$P-labeled porcine 691 PG-3 cDNA. The filters were washed several times, finally at 60° C. in 0.1×SSC and 0.1% SDS, and exposed to x-ray film with an intensifying screen at –70° C. Positive clones were subjected to two additional rounds of plaque purification at low density.

DNA purified from hybridizing clones was digested with various restriction endonucleases (New England Biolabs, Beverly, Mass.), fractionated on 0.8% agarose gels, and transferred onto GeneScreen Plus membrane (DuPont, Boston, Mass.). The hybridization probes were labeled with $^{32}$P and included porcine PG-3 cDNA, and 5'-labeled protegrin-specific oligonucleotide complementary to nt 403–429 of PG-1, 2 and 3 cDNAs. For the cDNA probe, the hybridization and washing conditions were carried out as for the library screening. For the oligonucleotide probe, the membranes were washed at 42° C. in 0.1×SSC, 0.1% SDS.

Southern blot analysis was carried out with purified DNA from positive clones by hybridization with protegrin cDNA and a protegrin specific oligonucleotide complementary to nt 403–429 of protegrin cDNA sequences. Although all of the clones hybridized with the complete cDNA probe, only about half of them hybridized with the protegrin-specific probe. A specific oligonucleotide probe for porcine prophenin, another cathelin-associated porcine leukocyte-derived antimicrobial peptide, hybridized to several of the nonprotegrin clones. These results confirm a) that the conserved proregion homologous to cathelin is present within the same gene as the mature antimicrobial peptides and is not added on by posttranscriptional events, and b) that the protegrins account for about half of the cathelin-related genes in the pig.

A synthetic peptide corresponding to the amino acid sequence of PG-5 was prepared and tested with respect to antimicrobial activity against *E. coli*, *L. monocytogenes* and *C. albicans*. The results were compared to those obtained with a synthetically prepared PG-1. The results are shown in FIGS. 11a–11c. As shown in these graphical representations of the results, PG-5 has comparable antimicrobial activity to PG-1 against all three organisms tested.

EXAMPLE 9

Preparation of EnantioPG-1

Using standard solid phase techniques, a protegrin having the amino acid sequence of PG-1, but wherein every amino acid is in the D form was prepared. This form of protegrin was tested against *E. coli, L. monocytogenes, C. albicans* and other microbes in the absence and presence of protease and otherwise as described for the radiodiffusion assay in agarose gels set forth in Example 1. The results are shown in FIGS. 12a–12g.

Figure 12B:
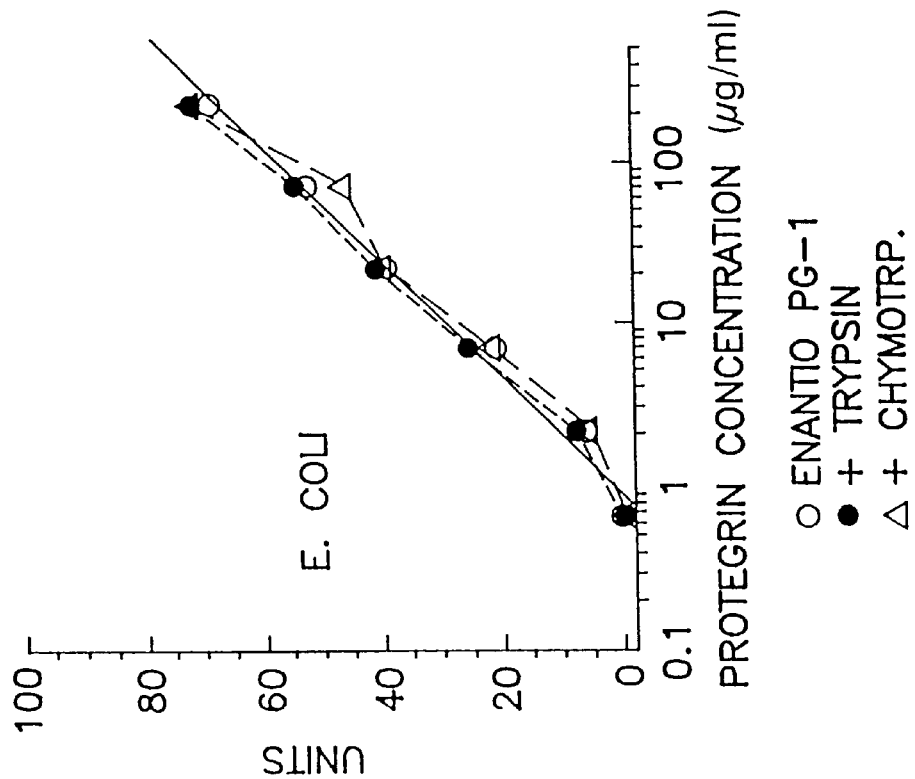
FIGS. 12a–12d show the effects of various protegrins against various target microbes.
Figure 12A:
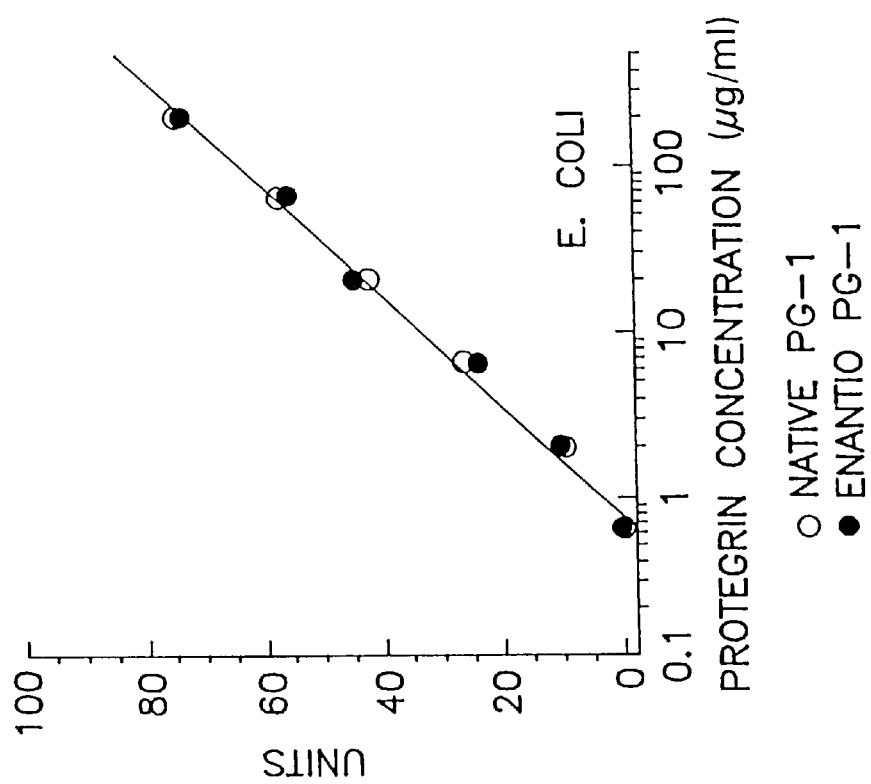
Figure 12D:
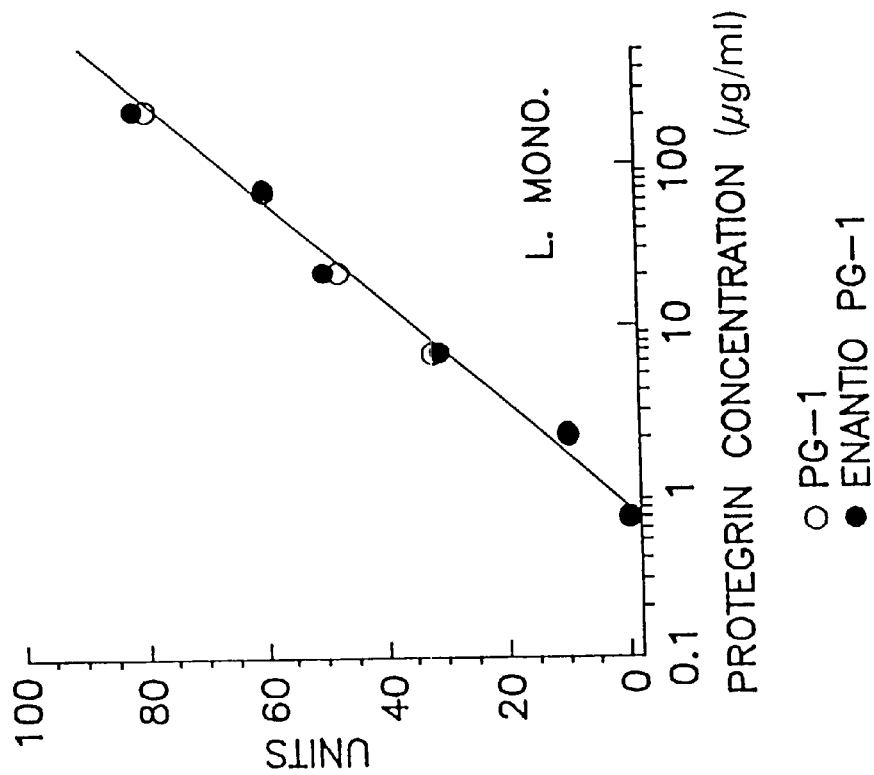
Figure 12C:
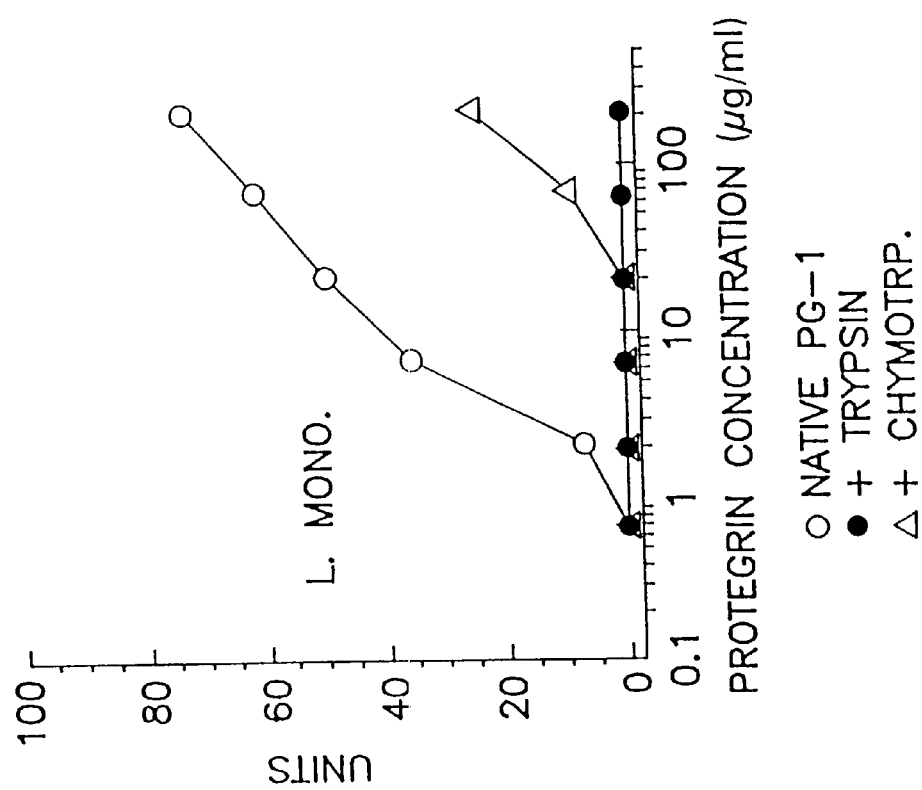

FIG. 12a shows that both native PG-1 and enantioPG-1 in the absence of protease are equally effective in inhibiting the growth of *E. coli*. FIG. 12b shows that neither trypsin nor chymotrypsin inhibits the antibacterial effect of enantioPG-1. FIG. 12c shows that in the presence of these proteolytic enzymes, the ability of native PG-1 to inhibit the growth of *L. monocytogenes* is adversely affected, although, as shown in FIG. 12d, in the absence of these proteases PG-1 is comparably active to an enantioPG-1.

EXAMPLE 10

Activity of the Protegrins Against STD Pathogens

Table 8 summarizes the activity of the protegrin PG-1 as compared to the defensin HNP-1 against growth of STD pathogens. In these results, "active" means that the peptide was effective at less than 10 µg/ml; moderately active indicates that it was active at 10–25 µg/ml; and slightly active means activity at 25–50 µg/ml. If no effect was obtained at 50–200 µg/ml the compound was considered inactive.

TABLE 8

| Activity against human STD pathogens | Protegrin PG-1 | Defensin HNP-1 |
| --- | --- | --- |
| HIV-1 | Active | Slightly active |
| Chlamydia trachomatis | Active | Slightly active |
| Treponema pallidum | Active | Inactive |
| Neisseria gonorrhoeae | Active | Inactive |
| Trichomonas vaginalis | Moderately active | Inactive |
| Herpes simplex type 2 | Moderately active | Slightly active |
| Herpes simplex type 1 | Inactive | Slightly active |
| Hemophilus ducreyi | Not tested | Not tested |
| Human papilloma virus | Not tested | Not tested |

*Chlamydia trachomatis*

Unlike other bacteria associated with STDs, Chlamydia requires an intracellular habitat for metabolic activity and binary fission. The life cycle is as follows: there is an extracellular form which is a metabolically inactive particle somewhat sporelike in its behavior, referred to as an elementary body (EB). The EB attaches to the host cell and is ingested to form an internal vacuolar space often called an "inclusion". The bacterium reorganizes to the delicate reticulate body (RB) which is noninfective but metabolically active and which over a 48–72 hour period undergoes reformation to the EB state. The EBs are then released from the cell. Rather than a peptidoglycan layer, Chlamiydia contains multiple disulfide linkages in cysteine-rich proteins for protection in the EB stage.

The protegrins of the invention were tested for their antimicrobial activity against Chlamydia using the "gold standard" chlamydial culture system for clinical specimens described by Clarke, L. M. in *Clinical Microbiology Procedures Handbook II* (1992), Isenberg, H. T. Ed. Am. Soc. Microbiol. Washington, D.C.; pp. 8.0.1 to 8.24.3.9. Briefly, McCoy cells (a mouse cell line) in cycloheximide EMEM with 10% fetal bovine serum (FBS) are used as hosts. Prior to chlamydial inoculation, the maintenance medium is aspirated without disruption of the cell layer and the cell layer is maintained on a cover slip in a standard vial. Each vial is then inoculated with 100–300 µL inoculum and centrifuged at 3500× g for one hour at 20° C. The fluid is then aspirated and 1 ml of EMEM is added. The vials are capped and incubated at 37° C. for 48 hours. After 48 hours the medium is again aspirated, coverslips are rinsed twice with PBS and fixed with 300 µL EtOH for 10 minutes. The EtOH is aspirated and the vials are allowed to dry; then one drop PBS plus 30 µL Syva Microtrak monoclonal antibody to the major outer membrane protein of Chlamydia is added for staining. After 37° C. incubation for 30 minutes, the cells are washed with distilled water and examined for inclusions which are easily recognizable as bright, apple-green-staining cytoplasmic vacuoles. They represent the equivalent of a colony of free-living bacteria on standard bacterial culture media.

In the assays conducted below, C. trachomatis serovar L2 (L2/434 Bu) described by Kuo, C. C. et al. in *Nongynococcal Urethritis and Related Infections* (1977), Taylor-Robinson, D. et al. Ed. Am. Soc. Microbiol. Washington, D.C., pp. 322–326 was used. The seed is prepared from a sonicated culture in L929 mouse fibroblast cells, and partially purified by centrifugation. Since host protein is still present in the seed aliquots, each seed batch is titered at the time of preparation with serial ten-fold dilutions to $2\times10^{-9}$. The seed containing $9.2\times10^6$ IFU/ml is thawed quickly at 37° C. and diluted to 10–2 with sucrose/phosphate salts/glycine to produce IFU of about 200 after room temperature preincubation and to dilute background eukaryotic protein. In the initial assays, the peptides to be tested were prepared as stock solutions in 0.01% glacial acetic acid. 100 µL of the diluted chlamydial seed was aliquoted into 1.5 ml eppendorf tubes and 200 µL of the antibiotic peptide was added per tube. Aliquots of the peptide stock (and controls) were incubated with the seed at room temperature for one hour, two hours and four hours. About 10 minutes before the end of each incubation period, maintenance media were aspirated from the McCoy vials in preparation for standard inoculation and culture. Culture was then performed in the presence and absence of the peptides; in some cases, the peptides were added to final concentration in the culture media in addition to the preculture incubation. The test was evaluated microscopically.

The results using 50 µg of protegrin per addition were dramatic. In control cultures, where no peptides were added, 222–460 inclusions were counted. In all protocols where protegrin was added either before the Chlamydia seed was added to the cells or both before and after, no inclusions were found. Similar results were obtained with 20 µg additions of tachyplesin. The defensins NP-1 and HNP-1 had lesser protective effects. In summary, the protegrins tested show antimicrobial against Chlamydia.

In the next series of experiments, various concentrations of protegrin (1 µg, 12.5 µg, 25 µg and 50 µg) were used in the two-hour preincubation. Concentrations as low as 12.5 µg lowered the number of inclusions to zero. Even at a concentration of 1 µg/ml, the number of inclusions was lowered dramatically from about 110 to about 30.

In the next set of experiments, the effect of the presence of serum was tested. The Chlamydia seed was preincubated for two hours with and without 10% FBS and also with or without protegrin at 25 µg. Protegrin was highly effective both with and without serum, whereas human defensin HNP-2, used as a control, was reasonably effective in the absence of serum but only marginally effective in its presence.

The experiments were repeated but adding 25 μg of protegrin one after the start of the chlamydial culture, i.e., after centrifugation and final medium mix and one hour into the beginning of the 48-hour culture period. Protegrin reduced the number of inclusions by approximately 57% from untreated controls although HNP-2 was completely ineffective. Finally, the protegrin (at 25 μg) was added to the chlamydial seed and the mix then immediately cultured. In this case, without preincubation and without the one-hour post-infection gap, protegrin was minimally effective without or without serum.

The effect of serum is particularly important since for a topical agent to be effective in combatting Chlamydia infection, it must act in the presence of serum.

In addition, there are several mouse-based models for Chlamydia infection which can be used to assess the efficacy of the protegrins. These include those described by Patton, D. L. et al. in *Chlamydial Infections* (1990) Bowie, W. R. et al. Eds. Cambridge University Press N.Y. pp. 223–231; Swenson, C. E. et al. *J. Infect. Dis.* (1983) pp. 1101–1107, and Barron, A. L. et al. *J. Infect. Dis.* (1981) 143:63–66.

*Neisseria gonorrhoeae*

In more detail, the ability of the protegrins to inhibit N. gonorrhoeae was tested by a modification of the method of Miyasaki et al., *Antimicrob Agent Chemother* (1993) 37:2710–2715. Nonpiliated transparent variants of strains FA 19 and F 62 were propagated on GCB agar plates containing glucose and iron supplements overnight at 37° C. under 3.8% V/V CO2. These strains were chosen for their adaptability to the assay.

The overnight growth is removed from the agar plate and suspended in GCB broth containing supplements and sodium bicarbonate and grown with shaking at 37° C. to mid log phase. The culture is diluted 1:100 in GCB broth to give about $10^6$ CFU/ml and serial dilutions were plated onto GCB agar.

The peptides are dissolved in 0.01% v/v acetic acid to give a 1 mg/ml stock solution and serially diluted. Ten μl of each dilution is added to a sterile polystyrene tube containing 90 μl of diluted bacteria and the tubes are shaken at 37° C. for 45 minutes. The contents are serially diluted 1:10 and plated on to GCB agar plates which are incubated in a $C_2$ incubator. CFU are counted after 24 hours and the log bactericidal activity calculated.

Native PG-1, synthetic PG-1, synthetic PG-3 amide and synthetic PG-3 without amidation all gave over a 5 log reduction in CFU per ml in this assay. Native PG-2 (containing 16 amino acids) gave a 2.6 fold reduction.

In addition enantioPG-1, the unidisulfide PG-1 ($C_6$–$C_{15}$), and unisulfide PG-1 ($C_8$–$C_{13}$) gave over a 5-fold log reduction in CFU/ml in this assay.

*Treponema pallidum*

Bacteriocidal activity against this organism, which is the etiologic agent of syphilis, was also tested. Peptides were evaluated at a series of concentrations of 1.758 μg to 56.25 μg in 90 μl of unheated normal rabbit serum. The serum served as a nutrient for the spirochetes to allow their survival during incubation as well as providing a source of complement. Ten μl of a suspension of T. pallidum containing about $5\times10^7$/μl organisms was added to each tube and the mixtures with the appropriate peptides were incubated at 34° C. under 95% $N_2$ and 5% $CO_2$. At time zero, just prior to incubation, 4 hours and 16 hours, 25 randomly selected organisms were examined for the presence or absence of motility. The 50% immobilizing end point ($IE_{50}$) was calculated to indicate the concentration needed to immobilize 50% of the spirochetes. In the presence of PG-1, the $IE_{50}$ at 0 and 4 hours was 2.717 μg and <1.758 μg, respectively. Tachyplesin $IE_{50}$'s were 5.231 μg and 2.539 μg for 0 and 4 hours. This was in contrast to HNP and NP preparations which showed little immobilizing ability.

Herpes Simplex Virus

Using viral stocks prepared in VERO cells, grown in minimal essential medium (MEM) with 2% fetal calf serum, the effect of various peptides on HSV 1 MacIntyre strain, a pool of ten clinical HSV 1 isolates, HSV-2G, and a pool of ten clinical HSV 2 isolates, all sensitive to 3 μM acyclovir were tested. Two fibroblast cell lines, human W138 and equine CCL57, were used as targets and tests were done by direct viral neutralization and delayed peptide addition.

In the direct neutralization format, the virus was preincubated with the peptides for 90 min before it was added to the tissue culture monolayers. In the delayed peptide addition format, the virus was added and allowed 50 min to adsorb to the target cells, then the monolayers were washed and peptides were added for 90 min. Finally, the monolayer was washed to remove the peptide and the cells were fed with peptide-free MEM and cultured until the untreated infected monolayers exhibited 4+ cytopathic effect (CPE) (about 60 hours).

Antiviral activity was seen in both formats, but was more pronounced with the delayed peptide addition mode. In experiments performed with W138 and CCL57 cells in the direct neutralization format, PG-1 completely prevented HSV-2G from causing CPE at concentrations of 50 μg/ml and 25 μg/ml, but these concentrations afforded no protection against HSV-1, which produced 4+ CPE.

In the delayed peptide addition format, PG-1 completely prevented CPE by HSV-2G at 35 μg/ml and 50 μg/ml and it also fully protected against the clinical HSV-2 pool at both concentrations.

Thus, PG-1 protected human and animal cells from infection by laboratory and clinical strains of HSV-2, even when the peptides were added as late as 60 min after the virus had been introduced into the cell culture.

*Trichomonas vaginallis*

*Trichomonas vaginallis* strain C1 (ATCC 30001) was grown as described by Gorrell, T. E. et al, *Carlsberg Res Comm* (1984) 49:259–268. In experiments performed in RPMI+1% heat-activated fetal calf serum, within a few minutes after exposure to 50 μg/ml PG-1, *T. vaginallis* (heretofore vigorously motile) became stationary. Soon thereafter, the organisms became permeable to trypan blue, and, over the ensuing 15–30 minutes, lysed. As expected, such organisms failed to grow when introduced into their customary growth medium (Diamond's medium). Organisms exposed to 25 μg/ml of PG-3 retained their motility.

Initial studies with two highly metronidazole-resistant clinical isolates of *T. vaginallis*, strains MR and TV showed both were susceptible to PG-1, including the $C_8$–$C_{13}$ and $C_6$–$C_{15}$ uni-disulfides and enantioPG-1 at concentrations of 100 and 50 μg/ml.

EXAMPLE 11

Antiretroviral Activity

Both synthetic and native PG-1 and native PG-2 were tested for antiviral activity against strains of HIV using the method described in Miles, S. A. et al., *Blood* (1991) 78:3200–3208. Briefly, the mononuclear cell fraction is recovered from normal donor leukopacs from the American Red Cross using a Ficoll-hypaque density gradient. The mononuclear cells are resuspended at $1\times10^6$ cells per ml in RPMI 1640 medium with 20% fetal bovine serum, 1% penn/strep with fungizone and 0.5% PHA and incubated 24 hours at 37° C. in 5% $CO_2$. The cells are centrifuged, washed and then expanded for 24 hours in growth medium.

Non-laboratory adapted, cloned $HIV_{JR-CSF}$ and $HIV_{JR-FL}$ were electroporated into the human peripheral blood mononuclear cells prepared as described above. Titers were determined and in general, multiplicities of infection (MOI) of about 4,000 infectuous units per cell are used (which corresponds to 25–40 picograms per ml HIV p24 antigen in the supernatant).

In the assay, the HIV stocks prepared as above were diluted to the correct MOI and the PBM are added to 24 well plates at a concentration of $2\times10^6$ per ml. One $\mu$l total volume is added to each well. The peptide to be tested is added in growth medium to achieve the final desired concentration. Then the appropriate number of MOI are added. To assay viral growth, 200 $\mu$l of supernatant is removed on days 3 and 7 and the concentration of p24 antigen is determined using a commercial assay (Coulter Immunology, Hialeah, Florida). Controls include duplicate wells containing cells alone, cells plus peptide at 5 $\mu$g/ml cells with virus but not peptide and cells with virus in the presence of AZT at $10^5$ M–$10^{-8}$ M.

Using this assay, it was demonstrated that both natural and synthetic PG-1 completely inhibit HIV infection at concentrations between 1–5 $\mu$g/ml; $IC_{90}$ was<5 $\mu$g/ml. The time of addition of peptide was then varied. Cells pretreated for 2 hours prior to addition of virus, at the time of addition of virus, or 2 hours after infection showed antiviral activity for the peptide. However, if PG-1 was added 24 hours after infection, there was no antiviral activity.

Further, PG-2 shows similar activity but at a level approximately 5-fold less. Alternative antibiotics such as human defensins and rabbit defensins lacked potent activity in this assay. The results were similar for both $HIV_{JR-CSF}$ and $HIV_{JR-FL}$ which are non-laboratory adapted isolates (Koyanagi, Y. S. et al, *Science* (1987) 236:819–822).

The protegrins show similar activity with respect to other retroviruses.

EXAMPLE 12

Preparation of Modified Protegrins: Kite and Bullet Forms

The kite and bullet forms of PG-1 wherein all X are alanine were synthesized using conventional Fmoc chemistry. The crude synthetic peptide was reduced by adding dithiothreitol (DTT) equal in weight to the synthetic peptide which had been dissolved at 10 mg peptide/ml in a solution containing 6 molar guanidine HCl, 0.5 molar tris buffer, and 2 mM EDTA, pH 8.05 and incubated for two hours at 52° C. under nitrogen. The mixture was passed through a 0.45 micron filter, acidified with 1/20 (v/v) glacial acidic acid and subjected to conventional RP-HPLC purification with a C-18 column. HPLC-purified, reduced synthetic bullet and kite PG-1 were partially concentrated by vacuum centrifugation in a speed vac and allowed to fold for 24 hours at room temperature in ambient air in 0.1 M Tris pH 7.7 at low concentration (0.1 mg peptide/ml) to minimize formation of interchain cystine disulfides. The mixture was then concentrated and acidified with HOAC to a final concentration of 5% and subjected to RP-HPLC purification.

The purity of the final products bullet and kite PG-1 was verified by AU-PAGE, analytical HPLC, and FAB-mass spec. AU-PAGE showed a single band for the final product in each case. The observed MH+ mass values were 2093 in both cases.

EXAMPLE 13

Antimicrobial Activity of the Kite and Bullet Forms

The kite and bullet PG-1 compounds prepared in Example 12 were tested for antimicrobial activity using the radial diffusion assay described in Example 1 as published by Lehrer, R. I. et al., *J Immunol Meth* (1991) 137:167–173, except that the underlay agars contained 10 mm sodium phosphate buffer with a final pH of 7.4. As described in Example 1, 0.3 mg/ml tripticase soy broth powder and 1% agarose were used as well in the underlay agar. In some cases 100 mM NaCl or RPMI plus 2.5% normal human serum (NHS) was added to the agar.

In a first set of determinations, the bullet and kite forms of PG-1 were tested for antimicrobial activity against *L. monocytogenes, E. faecium* (VR) or *S. aureus* under these three sets of conditions. FIG. 13 shows the result.

As shown, the bullet and kite forms were roughly equally effective against these three bacteria using standard assay conditions. When 100 mM NaCl was added to the agar, however, the kite forms appeared slightly less active than the bullet forms which appear to have slightly enhanced antimicrobial activity against all three stains except *S. aureus* under these conditions. Similarly, when RPMI plus 2.5% NHS were added, the bullet forms were again more effective than the kite forms. The activity of the kite form versus *E. faecium* was significantly less under these conditions.

Figures 14A, 14B, 14C:
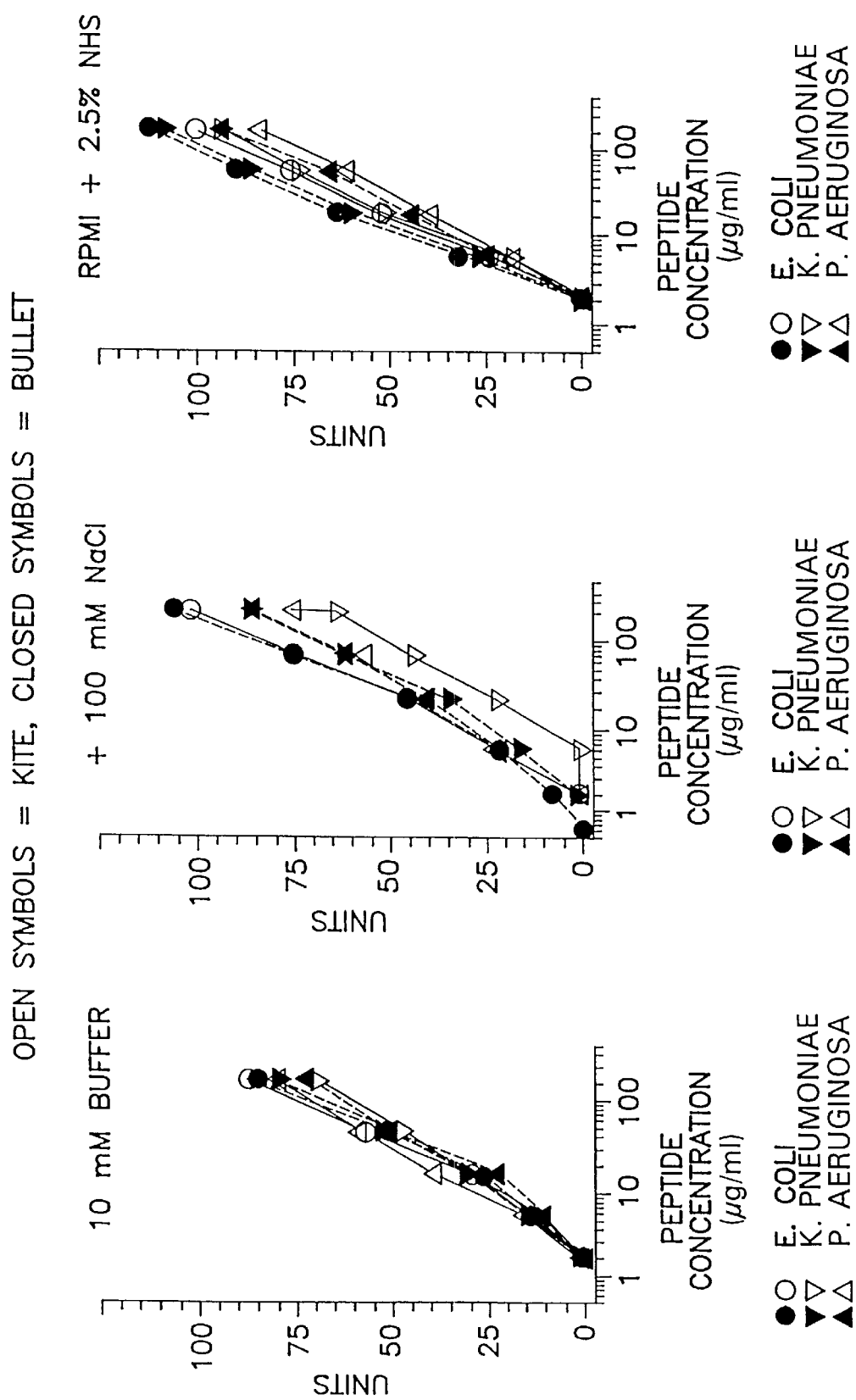
FIG. 14 shows a graphical representation of the effects of the kite and bullet forms of PG-1 against gram negative bacteria.

As shown in FIG. 14, these forms of PG-1 were also tested against *E. coli, K. pneumoniae* and *P. aeruginosa*. All three microorganisms were inhibited by both kite and bullet forms under standard conditions. This antimicrobial activity was maintained also at 100 mM NaCl and RPMI plus NHS.

EXAMPLE 14

Synthesis of the Snake Form of PG-1

The snake form of PG-1 wherein all X are alanine was performed using standard methods by Synpep Inc., Dublin, Calif. and the MH+ value in FAB-mass spec was 2031.3 as expected. The snake form was purified to homogeneity by RP-HPLC.

EXAMPLE 15

Antimicrobial Activity of Snake PG-1

Figures 15A, 15B, 15C:
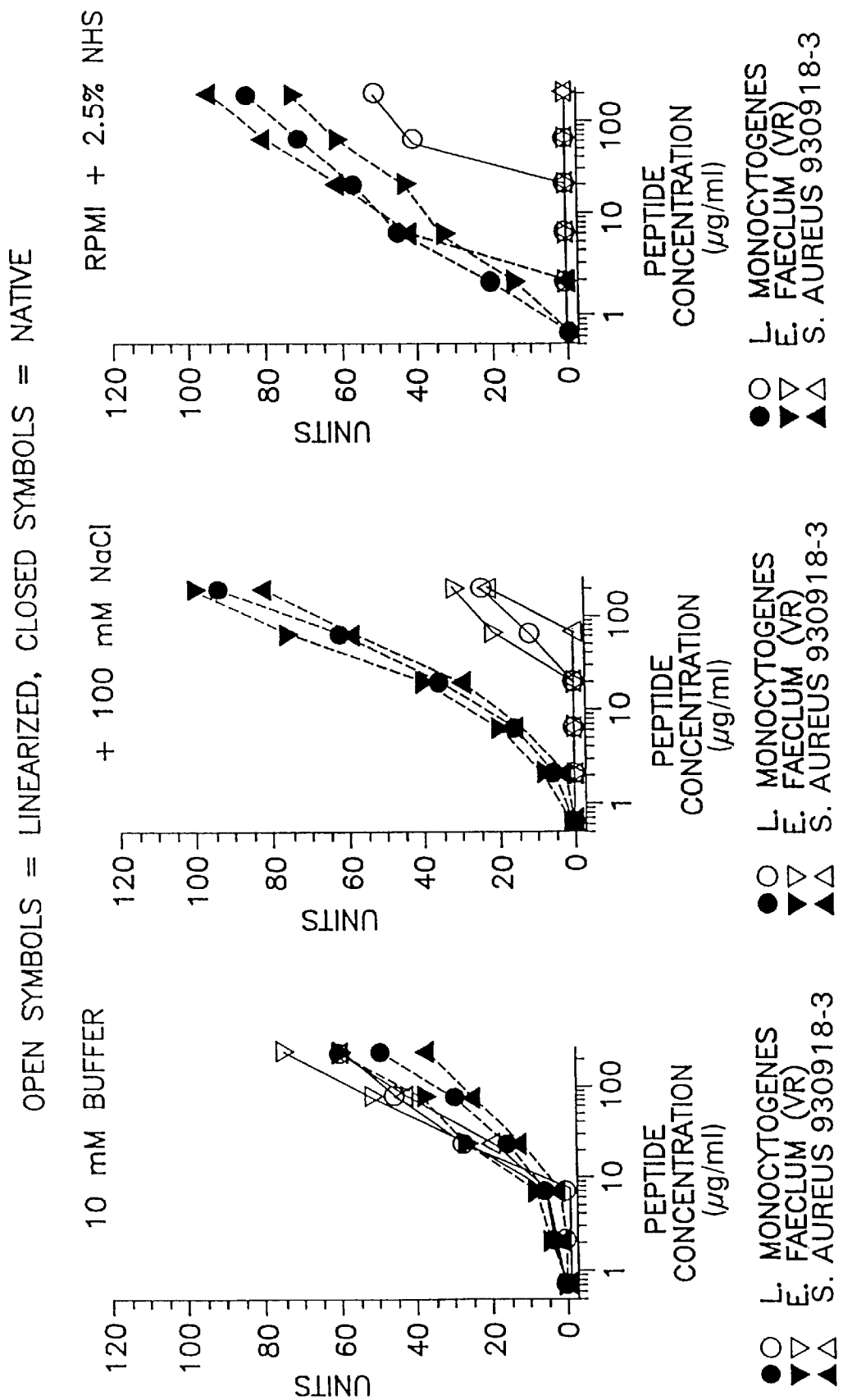
FIG. 15 is a graphical representation of the antimicrobial activity of the snake form of PG-1 against gram positive bacteria.

Snake PG-1 was tested with respect to the same six organisms and using the same conditions as set forth in Example 13 with respect to the bullet and kite forms of PG-1. The results are shown in FIGS. 15 and 16. In this case, the native two-cystine form of PG-1 (native) was used as a control. While the snake form shows somewhat superior activity with respect to *L. monocytogenes, E. faecium*, and *S. aureus* under standard conditions, it is notably less effective than the native form in the presence of either 100 mM NaCl or RPMI plus NHS. The same pattern is followed, as shown in FIG. 9 when the test organisms are *E. coli, K. pneumoniae*, and *P. aeruginosa*.

What is claimed is:

1. A purified and isolated or recombinantly produced compound which has antimicrobial or antiviral activity and which has the formula

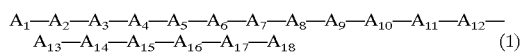

$$A_1\text{—}A_2\text{—}A_3\text{—}A_4\text{—}A_5\text{—}A_6\text{—}A_7\text{—}A_8\text{—}A_9\text{—}A_{10}\text{—}A_{11}\text{—}A_{12}\text{—}A_{13}\text{—}A_{14}\text{—}A_{15}\text{—}A_{16}\text{—}A_{17}\text{—}A_{18} \quad (1)$$

or a pharmaceutically acceptable salt or an N-terminal acylated or a C-terminal amidated or esterified form thereof, which is either in a linear form or in a cystine-bridged form, wherein:

each of $A_1$ and $A_9$ is independently a basic amino acid;
each of $A_2$ and $A_3$ is independently a small amino acid;
each of $A_5$, $A_7$, $A_{12}$, $A_{14}$ and $A_{16}$ is independently a hydrophobic amino acid;
$A_4$ is a basic or a small amino acid;
$A_{10}$ is a basic or a small amino acid or is proline;
$A_{11}$ is a basic or a hydrophobic amino acid;
$A_{17}$ is not present or, if present, is a small amino acid;
$A_{18}$ is not present or, if present, is a basic amino acid; and
each of $C_6$, $C_8$, $C_{13}$ and $C_{15}$ is independently selected from the group consisting of cysteine, a hydrophobic amino acid, a large polar amino acid and a small amino acid.

2. The compound of claim 1 which has one or more characteristics selected from the group consisting of:

the C-terminal carboxyl is of the formula selected from the group consisting of COOH or salts thereof, COOR, $CONH_2$, CONHR and $CONR_2$ wherein each R is independently a hydrocarbyl (1–6C);

the amino group at the N-terminus is of the formula $NH_2$ or NHCOR wherein R is a hydrocarbyl (1–6C);

each of $A_1$ and $A_9$ is independently selected from the group consisting of R, K and Har;

each of $A_2$ and $A_3$ is independently selected from the group consisting of G, A, S and T;

$A_4$ is R or G;

each of $A_5$, $A_{14}$, and $A_{16}$ is independently selected from the group consisting of I, V, NLe, L and F;

each of $A_7$ and $A_{12}$ is independently selected from the group consisting of I, V, L, W, Y and F;

$A_{10}$ is R, G or P; and $A_{11}$ is R or W.

3. The compound of claim 1 which has antimicrobial or antiviral activity against a pathogen associated with a sexually transmitted disease.

4. The compound of claim 1 which has antimicrobial or antiviral activity against Escherichia coli, Listeria monocytogenes, Candida albicans, Pseudomonas aeruginosa, Klebsiella pneumoniae, Salmonella typhimurium, Staphylococcus aureus, Histoplasma capsulatum, Myobacterium avium-intracellulare, Mycobacterium tuberculosis, Vibrio vulnificus, Chlamydia trachomatis, Treponema pallidum, Neisseria gonorrhoeae, Trichomonas vaginalis, Herpes simplex virus type 1, Herpes simplex virus type 2, human immunodeficiency virus, Hemophilus ducreyi, or human papilloma virus.

5. A method of inhibiting the growth of a sexually-transmittable microbe or the replication of a sexually-transmittable virus which comprises the step of contacting said sexually-transmittable virus or said sexually-transmittable microbe with an amount of a compound according to claim 1 effective to inhibit said growth or said replication.

6. The method of claim 5 in which the sexually-transmittable microbe is a sexually-transmittable bacterium.

7. The method of claim 5 in which the sexually-transmittable microbe or virus is selected from the group consisting of human immunodeficiency virus type 1, Chlamydia trachomatis, Treponema pallidum, Neisseria gonorrhoeae, Trichonomis vaginalis, Herpes simplex virus type 1, Herpes simplex virus type 2, Hemophilus ducreyi and human papilloma virus.

8. The method of claim 5 in which the sexually-transmittable microbe or virus is human immunodeficiency virus.

9. A method to treat or prevent a sexually-transmitted microbial or viral infection in a subject, which method comprises administering to a subject in need of such treatment an amount of a compound according to claim 1 effective to treat or prevent said infection in the subject.

10. The method of claim 9 in which the infection is a bacterial infection.

11. The method of claim 9, in which the compound is administered therapeutically.

12. The method of claim 9 10 or 11 in which the infection is a bacterial infection.

13. The method of claim 9, 10 or 11 in which the sexually-transmitted infection is caused by a microbe or virus selected from the group consisting of human immunodeficiency virus type 1, Chlamydia trachomatis, Treponema pallidum, Neisseria gonorrhoeae, Trichonomis vaginalis, Herpes simplex virus type 1, Herpes simplex virus type 2, Hemophilus ducreyi and human papilloma virus.

14. The method of claim 9, 10 or 11 in which the infection is a human immunodeficiency virus infection.

15. The method of claim 9, 10 or 11 in which the compound is administered topically.

* * * * *